United States Patent [19]

Mollet et al.

[11] Patent Number: 5,733,765
[45] Date of Patent: Mar. 31, 1998

[54] LACTIC BACTERIA PRODUCING EXOPOLYSACCHARIDES

[75] Inventors: Beat Mollet, Mollie-Margot; Francesca Stingele, Lausanne, both of Switzerland

[73] Assignee: Nestec S.A., Vevey, Switzerland

[21] Appl. No.: 597,236

[22] Filed: Feb. 6, 1996

[30] Foreign Application Priority Data

Jun. 20, 1995 [EP] European Pat. Off. ............. 95201669

[51] Int. Cl.⁶ .................................. C12N 9/00; C12N 9/10
[52] U.S. Cl. ...................... 435/183; 435/193; 436/23.1; 436/23.2; 436/23.7
[58] Field of Search ..................... 435/101, 193, 435/200, 69.1, 70.1, 170, 252.3, 183

[56] References Cited

FOREIGN PATENT DOCUMENTS

WO 88/00948  2/1988  WIPO.
WO 92/02142  2/1992  WIPO.

OTHER PUBLICATIONS

Angelo Guidolin et al., "Nucleotide Sequence Analysis of Genes Essential for Capsular Polysaccharide Biosynthesis in Streptococcus Pneumoniae Type 19F", Infection and Immunity, vol. 62, No. 12, Dec. 1994, pp. 5384–5396.

Ernesto Garcia et al., "Cloning and Sequencing of a Gene involved in the Synthesis of the Capsular Polysaccharide of Streptococcus Pheumoniae Type 3", Molecular and General Genetics, vol. 239, No. 1–2, May 1993 Berlin de, pp. 188–195.

Marisa Vescovo et al., "Plasmid–Encoded Ropiness Production in Lactobacillus Casei SSP. Casei" Biotechnology Letter, vol. 11, No. 10, Oct. 1989, pp. 709–712.

Thierry Doco et al., "Structure of an Exocellular Polysaccharide Produced by Streptococucu Thermophilus", Carbohydrate Research, vol. 198, No. 2, May 1, 1990 Amsterdam NL, pp. 313–321.

Creighton, T. E. "Proteins: Structure and Molecular Properties" Second Edition, 1993, W. H. Freeman and Company New York, pp. 108–109 and 132–133.

Rubens et al. "Identification of cpsD, a gene essential for type III capsule expression in group B streptococci" Mol. Microbiol. 8, 843–855, 1993.

*Primary Examiner*—Robert A. Wax
*Assistant Examiner*—Nashaat T. Nashed
*Attorney, Agent, or Firm*—Pennie & Edmonds LLP

[57] ABSTRACT

DNA fragment of genomic origin coding for at least one enzyme involved in the biosynthesis of an EPS, and capable, following the transformation of a lactic bacteria, of restoring the production of an EPS in the said bacterium not initially producing any EPS, or of modifying the structure of the EPS initially produced by the said bacterium. Proteins of the *Streptococcus thermophilus* strain CNCM I-1590 encoded by the chromosome and which are involved in the biosynthesis of the EPS having the composition Glc:Gal:GalNac= 1:2:1. Method for the manufacture of a new EPS, in which a DNA fragment coding partially or totally for at least one enzyme involved in the biosynthesis of an EPS is cloned into a vector, lactic bacteria producing another EPS are transformed with the recombinant vector, and a lactic bacterium producing a new EPS is then selected.

3 Claims, 2 Drawing Sheets

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:

-continued

```
           ( A ) LENGTH: 14602 base pairs
           ( B ) TYPE: nucleic acid
           ( C ) STRANDEDNESS: double
           ( D ) TOPOLOGY: linear ( i i ) MOLECULE TYPE: DNA (genomic)

( i x ) FEATURE:
           ( A ) NAME/KEY: CDS
           ( B ) LOCATION: 352..1803
           ( D ) OTHER INFORMATION: /product="epsA"

( i x ) FEATURE:
           ( A ) NAME/KEY: CDS
           ( B ) LOCATION: 1807..2535
           ( D ) OTHER INFORMATION: /product="epsB"

( i x ) FEATURE:
           ( A ) NAME/KEY: CDS
           ( B ) LOCATION: 2547..3239
           ( D ) OTHER INFORMATION: /product="epsC"

( i x ) FEATURE:
           ( A ) NAME/KEY: CDS
           ( B ) LOCATION: 3249..3995
           ( D ) OTHER INFORMATION: /product="epsD"

( i x ) FEATURE:
           ( A ) NAME/KEY: CDS
           ( B ) LOCATION: 4051..4731
           ( D ) OTHER INFORMATION: /product="epsE"

( i x ) FEATURE:
           ( A ) NAME/KEY: CDS
           ( B ) LOCATION: 4898..5854
           ( D ) OTHER INFORMATION: /product="epsF"

( i x ) FEATURE:
           ( A ) NAME/KEY: CDS
           ( B ) LOCATION: 6425..7540
           ( D ) OTHER INFORMATION: /product="epsG"

( i x ) FEATURE:
           ( A ) NAME/KEY: CDS
           ( B ) LOCATION: 7736..8212
           ( D ) OTHER INFORMATION: /product="epsH"

( i x ) FEATURE:
           ( A ) NAME/KEY: CDS
           ( B ) LOCATION: 8221..9192
           ( D ) OTHER INFORMATION: /product="epsI"

( i x ) FEATURE:
           ( A ) NAME/KEY: CDS
           ( B ) LOCATION: 9285..10364
           ( D ) OTHER INFORMATION: /product="epsJ"

( i x ) FEATURE:
           ( A ) NAME/KEY: CDS
           ( B ) LOCATION: 10392..11339
           ( D ) OTHER INFORMATION: /product="epsK"

( i x ) FEATURE:
           ( A ) NAME/KEY: misc_feature
           ( B ) LOCATION: 11302..12222
           ( D ) OTHER INFORMATION: /product="CDS (eps L) covering CDS
                   ( e p s   k ) on nucleotides 10392-11339"

( i x ) FEATURE:
           ( A ) NAME/KEY: CDS
           ( B ) LOCATION: 12233..13651
           ( D ) OTHER INFORMATION: /product="epsM"

( i x ) FEATURE:
           ( A ) NAME/KEY: misc_feature
           ( B ) LOCATION: 13732..14305
           ( D ) OTHER INFORMATION: /function="CDS on the
                   complementary strand"
                   / product="orfz"
```

( i x ) FEATURE:
    ( A ) NAME/KEY: terminator
    ( B ) LOCATION: 230..252

( i x ) FEATURE:
    ( A ) NAME/KEY: promoter
    ( B ) LOCATION: 274..302

( i x ) FEATURE:
    ( A ) NAME/KEY: RBS
    ( B ) LOCATION: 340..345

( x i ) SEQUENCE DESCRIPTION: SEQ ID NO:1:

```
TAGTTTGTAA AAGGACGCCA TTTGGTCGTC CTTTTGTGTT GTAGCTAATA TCTGTTCGAA        60

GTGATAATAA GTTAAAATTT TTCAAACTAC TAGAAAAAAT AAAAATATTT GGAAGAAGAA       120

GACTTATAAT AAATAGGTAA ATATCTGACA ATTTAAAGTT TAACTACTAA AAATGTAAAA       180

GATAGTTCAC AATATAATGG AAAATGATAT AAATTAAATG ATTGATATCA TAATGAAAAA       240

CGTTTTCTTA TTTTTTTGAA AAAAGAATGA CAATTGAAAT GAGGTTGTAT TAATGTTATA       300

ATAATAATAA TAATGGGGAA TACCTAATTT TAATTTTTAG GAGCAATTTA T ATG AGT        357
                                                        Met Ser
                                                          1

TCG CGT ACG AAT CGT AAG CAA AAG CAT ACG AGT AAT GGA TCG TGG GGG         405
Ser Arg Thr Asn Arg Lys Gln Lys His Thr Ser Asn Gly Ser Trp Gly
         5                  10                  15

ATG GTC AAC GTT GGG TTG ACC ATC CTG TAT GCT ATT TTA GCA TTG GTC         453
Met Val Asn Val Gly Leu Thr Ile Leu Tyr Ala Ile Leu Ala Leu Val
     20                  25                  30

TTA TTA TTC ACC ATG TTC AAT TAT AAT TTC CTA TCC TTT AGG TTT TTG         501
Leu Leu Phe Thr Met Phe Asn Tyr Asn Phe Leu Ser Phe Arg Phe Leu
 35                  40                  45                  50

AAC ATC ATT ATC ACC ATT GGT TTG TTG GTA GTT CTT GCT ATT AGC ATC         549
Asn Ile Ile Ile Thr Ile Gly Leu Leu Val Val Leu Ala Ile Ser Ile
                 55                  60                  65

TTC CTT CAG AAG ACT AAG AAA TTA CCA CTA GTG ACA ACG GTT GTA CTG         597
Phe Leu Gln Lys Thr Lys Lys Leu Pro Leu Val Thr Thr Val Val Leu
             70                  75                  80

GTT ATC TTC TCG CTA GTT TCT CTG GTT GGT ATT TTT GGT TTT AAA CAA         645
Val Ile Phe Ser Leu Val Ser Leu Val Gly Ile Phe Gly Phe Lys Gln
         85                  90                  95

ATG ATT GAC ATC ACT AAC CGT ATG AAT CAG ACA GCA GCA TTT TCT GAA         693
Met Ile Asp Ile Thr Asn Arg Met Asn Gln Thr Ala Ala Phe Ser Glu
    100                 105                 110

GTA GAA ATG AGC ATC GTG GTT CCT AAG GAA AGT GAC ATC AAA GAT GTG         741
Val Glu Met Ser Ile Val Val Pro Lys Glu Ser Asp Ile Lys Asp Val
115                 120                 125                 130

AGC CAG CTT ACT AGC GTA CAG GCA CCT ACT AAG GTT GAT AAG AAC AAT         789
Ser Gln Leu Thr Ser Val Gln Ala Pro Thr Lys Val Asp Lys Asn Asn
                135                 140                 145

ATC GAG ATC TTG ATG TCA GCT CTC AAA AAA GAT AAA AAA GTT GAT GTT         837
Ile Glu Ile Leu Met Ser Ala Leu Lys Lys Asp Lys Lys Val Asp Val
            150                 155                 160

AAA GTT GAT GAT GTT GCC TCA TAT CAA GAA GCT TAT GAT AAT CTC AAG         885
Lys Val Asp Asp Val Ala Ser Tyr Gln Glu Ala Tyr Asp Asn Leu Lys
        165                 170                 175

TCT GGC AAA TCT AAA GCT ATG GTC TTG AGT GGC TCT TAT GCT AGC CTA         933
Ser Gly Lys Ser Lys Ala Met Val Leu Ser Gly Ser Tyr Ala Ser Leu
    180                 185                 190

TTA GAG TCT GTC GAT AGT AAT TAT GCT TCA AAT CTA AAA ACA ATT TAT         981
Leu Glu Ser Val Asp Ser Asn Tyr Ala Ser Asn Leu Lys Thr Ile Tyr
195                 200                 205                 210
```

| | | | | | | | | | | | | | | | | |
|---|---|---|---|---|---|---|---|---|---|---|---|---|---|---|---|---|
| ACT | TAT | AAA | ATT | AAA | AAG | AAG | AAT | AGC | AAC | TCT | GCA | AAC | CAA | GTA | GAT | 1029 |
| Thr | Tyr | Lys | Ile | Lys<br>215 | Lys | Lys | Asn | Ser<br>220 | Asn | Ser | Ala | Asn | Gln<br>225 | Val | Asp | |
| TCA | AGA | GTC | TTC | AAT | ATT | TAT | ATT | AGT | GGT | ATT | GAT | ACC | TAC | GGT | CCG | 1077 |
| Ser | Arg | Val | Phe<br>230 | Asn | Ile | Tyr | Ile | Ser<br>235 | Gly | Ile | Asp | Thr | Tyr<br>240 | Gly | Pro | |
| ATT | TCA | ACA | GTG | TCA | CGT | TCA | GAT | GTC | AAT | ATC | ATT | ATG | ACA | GTA | AAC | 1125 |
| Ile | Ser | Thr<br>245 | Val | Ser | Arg | Ser | Asp<br>250 | Val | Asn | Ile | Ile | Met<br>255 | Thr | Val | Asn | |
| ATG | AAT | ACA | CAT | AAG | ATT | CTC | TTG | ACG | ACT | ACT | CCA | CGT | GAT | GCA | TAC | 1173 |
| Met | Asn<br>260 | Thr | His | Lys | Ile | Leu<br>265 | Leu | Thr | Thr | Thr | Pro<br>270 | Arg | Asp | Ala | Tyr | |
| GTT | AAG | ATT | CCT | GGT | GGT | GGG | GCA | GAC | CAG | TAT | GAT | AAA | TTA | ACC | CAC | 1221 |
| Val<br>275 | Lys | Ile | Pro | Gly | Gly<br>280 | Gly | Ala | Asp | Gln | Tyr<br>285 | Asp | Lys | Leu | Thr | His<br>290 | |
| GCA | GGT | ATT | TAT | GGC | GTT | GAA | ACA | TCT | GAA | CAA | ACT | CTA | GAA | GAT | CTT | 1269 |
| Ala | Gly | Ile | Tyr | Gly<br>295 | Val | Glu | Thr | Ser | Glu<br>300 | Gln | Thr | Leu | Glu | Asp<br>305 | Leu | |
| TAT | GGT | ATT | AAG | CTT | GAT | TAC | TAT | GCA | CGA | ATT | AAC | TTC | ACA | TCT | TTC | 1317 |
| Tyr | Gly | Ile | Lys<br>310 | Leu | Asp | Tyr | Tyr | Ala<br>315 | Arg | Ile | Asn | Phe | Thr<br>320 | Ser | Phe | |
| CTT | AAG | TTG | ATT | GAC | CAA | CTT | GGT | GGT | GTG | ACA | GTC | CAT | AAT | GAT | CAA | 1365 |
| Leu | Lys | Leu<br>325 | Ile | Asp | Gln | Leu | Gly<br>330 | Gly | Val | Thr | Val | His<br>335 | Asn | Asp | Gln | |
| GCT | TTC | ACA | CAA | GAG | AAG | TTT | GAT | TTC | CCG | GTT | GGA | GAT | ATC | CAA | ATG | 1413 |
| Ala | Phe<br>340 | Thr | Gln | Glu | Lys | Phe<br>345 | Asp | Phe | Pro | Val | Gly<br>350 | Asp | Ile | Gln | Met | |
| AAT | TCA | GAG | CAA | GCA | CTT | GGA | TTT | GTT | CGT | GAA | CGC | TAT | AAT | TTA | GAT | 1461 |
| Asn<br>355 | Ser | Glu | Gln | Ala | Leu<br>360 | Gly | Phe | Val | Arg | Glu<br>365 | Arg | Tyr | Asn | Leu | Asp<br>370 | |
| GGC | GGA | GAT | AAT | GAC | CGT | GGT | AAA | AAC | CAG | GAG | AAA | GTT | ATT | TCT | GCG | 1509 |
| Gly | Gly | Asp | Asn | Asp<br>375 | Arg | Gly | Lys | Asn | Gln<br>380 | Glu | Lys | Val | Ile | Ser<br>385 | Ala | |
| ATT | TTA | AAC | AAG | TTG | GCT | TCT | CTA | AAA | TCT | GTA | TCA | AAC | TTT | ACT | TCA | 1557 |
| Ile | Leu | Asn | Lys<br>390 | Leu | Ala | Ser | Leu | Lys<br>395 | Ser | Val | Ser | Asn | Phe<br>400 | Thr | Ser | |
| ATC | GTT | AAT | AAT | CTC | CAA | GAC | TCT | GTC | CAA | ACG | AAT | ATG | TCT | TTG | AAT | 1605 |
| Ile | Val | Asn<br>405 | Asn | Leu | Gln | Asp | Ser<br>410 | Val | Gln | Thr | Asn | Met<br>415 | Ser | Leu | Asn | |
| ACC | ATT | AAC | GCT | TTG | GCT | AAT | ACA | CAA | CTT | GAA | TCA | GGT | TCT | AAA | TTT | 1653 |
| Thr | Ile<br>420 | Asn | Ala | Leu | Ala | Asn<br>425 | Thr | Gln | Leu | Glu | Ser<br>430 | Gly | Ser | Lys | Phe | |
| ACG | GTG | ACT | TCT | CAA | GCA | GTA | ACA | GGT | ACA | GGT | TCA | ACC | GGA | CAA | TTG | 1701 |
| Thr<br>435 | Val | Thr | Ser | Gln | Ala<br>440 | Val | Thr | Gly | Thr | Gly<br>445 | Ser | Thr | Gly | Gln | Leu<br>450 | |
| ATC | TCT | TAT | GCG | ATG | CCA | AAT | TCT | AGT | CTT | TAC | ATG | ATG | AAA | CTA | GAT | 1749 |
| Ile | Ser | Tyr | Ala | Met<br>455 | Pro | Asn | Ser | Ser | Leu<br>460 | Tyr | Met | Met | Lys | Leu<br>465 | Asp | |
| AAT | TCG | AGT | GTG | GAA | AGT | GCC | TCT | CAA | GCT | ATC | AAA | AAA | TTG | ATG | GAG | 1797 |
| Asn | Ser | Ser | Val<br>470 | Glu | Ser | Ala | Ser | Gln<br>475 | Ala | Ile | Lys | Lys | Leu<br>480 | Met | Glu | |
| GAA | AAA | TAA | GTG | ATT | GAC | GTT | CAC | TCA | CAT | ATT | GTT | TTT | GAT | GTT | GAT | 1845 |
| Glu | Lys | | Val<br>1 | Ile | Asp | Val | His<br>5 | Ser | His | Ile | Val<br>10 | Phe | Asp | Val | Asp | |
| GAT | GGT | CCT | GAA | ACT | TTA | GAA | GAA | AGT | TTA | GAC | CTC | ATT | GGT | GAA | AGT | 1893 |
| Asp | Gly<br>15 | Pro | Glu | Thr | Leu | Glu<br>20 | Glu | Ser | Leu | Asp | Leu<br>25 | Ile | Gly | Glu | Ser | |
| TAC | GCC | CAG | GGG | GTA | CGT | AAG | ATT | GTT | TCA | ACA | TCC | CAT | CGT | CGT | AAG | 1941 |
| Tyr<br>30 | Ala | Gln | Gly | Val | Arg<br>35 | Lys | Ile | Val | Ser | Thr<br>40 | Ser | His | Arg | Arg | Lys<br>45 | |

```
GGG ATG TTT GAG ACT CCA GAG GAT AAA ATT TTT GCC AAC TTT AAA AAA    1989
Gly Met Phe Glu Thr Pro Glu Asp Lys Ile Phe Ala Asn Phe Lys Lys
         50                  55                  60

GTA AAA GCA GAA GCA GAA GCA CTT TAT CCA GAC TTA ACT ATT TAT TAT    2037
Val Lys Ala Glu Ala Glu Ala Leu Tyr Pro Asp Leu Thr Ile Tyr Tyr
         65                  70                  75

GGA GGT GAA CTT TAT TAC ACC TCA GAC ATT GTG GAG AAA CTT GAA AAG    2085
Gly Gly Glu Leu Tyr Tyr Thr Ser Asp Ile Val Glu Lys Leu Glu Lys
         80                  85                  90

AAT CTC ATT CCG CGC ATG CAC AAC ACT CAA TTT GCT TTA ATT GAG TTT    2133
Asn Leu Ile Pro Arg Met His Asn Thr Gln Phe Ala Leu Ile Glu Phe
         95                 100                 105

AGT GCT CGC ACA TCT TGG AAA GAA ATT CAT AGT GGG CTT AGT AAT GTT    2181
Ser Ala Arg Thr Ser Trp Lys Glu Ile His Ser Gly Leu Ser Asn Val
110                 115                 120                 125

TTG AGA GCG GGG GTA ACG CCT ATT GTT GCT CAT ATT GAG CGC TAT GAT    2229
Leu Arg Ala Gly Val Thr Pro Ile Val Ala His Ile Glu Arg Tyr Asp
                130                 135                 140

GCC CTC GAA GAA AAT GCT GAC CGT GTT CGA GAA ATC ATC AAT ATG GGC    2277
Ala Leu Glu Glu Asn Ala Asp Arg Val Arg Glu Ile Ile Asn Met Gly
        145                 150                 155

TGC TAT ACT CAA GTC AAT AGC TCA CAT GTC CTC AAA CCA AAG CTC TTT    2325
Cys Tyr Thr Gln Val Asn Ser Ser His Val Leu Lys Pro Lys Leu Phe
        160                 165                 170

GGA GAT AAA GAT AAA GTA AGA AAG AAA CGT GTT CGC TTT TTC TTG GAG    2373
Gly Asp Lys Asp Lys Val Arg Lys Lys Arg Val Arg Phe Phe Leu Glu
175                 180                 185

AAA AAT TTG GTT CAT ATG GTT GCT AGC GAC ATG CAT AAT CTT GGG CCG    2421
Lys Asn Leu Val His Met Val Ala Ser Asp Met His Asn Leu Gly Pro
190                 195                 200                 205

AGA CCA CCA TTT ATG AAA GAT GCT TAT GAA ATT GTT AAA AAG AAC TAC    2469
Arg Pro Pro Phe Met Lys Asp Ala Tyr Glu Ile Val Lys Lys Asn Tyr
                210                 215                 220

GGC TCC AAA CGT GCT AAG AAT CTT TTT ATT GAA AAT CCC AAA ACA TTA    2517
Gly Ser Lys Arg Ala Lys Asn Leu Phe Ile Glu Asn Pro Lys Thr Leu
        225                 230                 235

CTA GAA AAT CAA TAT TTA TAGGAGATAT T ATG AAT CAA GAT AAC ACT AAA    2567
Leu Glu Asn Gln Tyr Leu             Met Asn Gln Asp Asn Thr Lys
        240                          1                   5

AGT GAT GAA ATC GAC GTA CTA GCA TTG CTA CAT AAA CTT TGG ACG AAG    2615
Ser Asp Glu Ile Asp Val Leu Ala Leu Leu His Lys Leu Trp Thr Lys
         10                  15                  20

AAG CTT TTG ATT CTT TTC ACA GCT TTT TAT TTC GCT GTT TTC AGT TTC    2663
Lys Leu Leu Ile Leu Phe Thr Ala Phe Tyr Phe Ala Val Phe Ser Phe
         25                  30                  35

TTA GGT ACT TAT TTC TTT ATC CAA CCA ACA TAT ACA TCA ACA ACG CGT    2711
Leu Gly Thr Tyr Phe Phe Ile Gln Pro Thr Tyr Thr Ser Thr Thr Arg
40                   45                  50                  55

ATC TAT GTT GTT AAT CAG GCA ACA GAT AAT AAG AAT CTT TCT GCT CAA    2759
Ile Tyr Val Val Asn Gln Ala Thr Asp Asn Lys Asn Leu Ser Ala Gln
                 60                  65                  70

GAT TTG CAA GCT GGT ACC TAT TTG GCA AAT GAC TAT AAA GAG ATT ATT    2807
Asp Leu Gln Ala Gly Thr Tyr Leu Ala Asn Asp Tyr Lys Glu Ile Ile
             75                  80                  85

GCA TCA AAT GAT GTA TTA TCA GAA GTT ATT AAA GAT GAA AAA TTG AAT    2855
Ala Ser Asn Asp Val Leu Ser Glu Val Ile Lys Asp Glu Lys Leu Asn
         90                  95                 100

TTG AGT GAG GCA GAA CTG TCT AAA ATG GTT TCA GTT AAT ATT CCT ACT    2903
Leu Ser Glu Ala Glu Leu Ser Lys Met Val Ser Val Asn Ile Pro Thr
         105                 110                 115
```

-continued

| | | | | | | | | | | | | | | | | |
|---|---|---|---|---|---|---|---|---|---|---|---|---|---|---|---|---|
| GAT | ACT | CGT | CTT | ATT | TCA | ATT | TCT | GTT | AAT | GCT | AAA | ACT | GGT | CAA | GAT | 2951 |
| Asp | Thr | Arg | Leu | Ile | Ser | Ile | Ser | Val | Asn | Ala | Lys | Thr | Gly | Gln | Asp | |
| 120 | | | | | 125 | | | | | 130 | | | | | 135 | |
| GCG | CAA | ACA | CTT | GCC | AAT | AAG | GTT | CGT | GAA | GTT | GCT | TCA | AAA | AAA | ATC | 2999 |
| Ala | Gln | Thr | Leu | Ala | Asn | Lys | Val | Arg | Glu | Val | Ala | Ser | Lys | Lys | Ile | |
| | | | | 140 | | | | | 145 | | | | | 150 | | |
| AAG | AAG | GTG | ACA | AAA | GTT | GAA | GAT | GTC | ACA | ACG | CTC | GAA | GAA | GCT | AAA | 3047 |
| Lys | Lys | Val | Thr | Lys | Val | Glu | Asp | Val | Thr | Thr | Leu | Glu | Glu | Ala | Lys | |
| | | | | 155 | | | | | 160 | | | | | 165 | | |
| TTG | CCA | GAG | TCA | CCA | TCT | TCA | CCA | AAT | ATC | AAA | CTT | AAT | GTG | CTT | CTT | 3095 |
| Leu | Pro | Glu | Ser | Pro | Ser | Ser | Pro | Asn | Ile | Lys | Leu | Asn | Val | Leu | Leu | |
| | | | | 170 | | | | | 175 | | | | | 180 | | |
| GGG | GCA | GTG | CTT | GGA | GGA | TTC | CTT | GCA | GTG | GTT | GGT | GTA | TTG | GTA | CGT | 3143 |
| Gly | Ala | Val | Leu | Gly | Gly | Phe | Leu | Ala | Val | Val | Gly | Val | Leu | Val | Arg | |
| | | | | 185 | | | | | 190 | | | | | 195 | | |
| GAA | ATC | CTA | GAT | GAT | CGT | GTT | CGC | CGT | CCA | GAA | GAT | GTG | GAA | GAT | GCC | 3191 |
| Glu | Ile | Leu | Asp | Asp | Arg | Val | Arg | Arg | Pro | Glu | Asp | Val | Glu | Asp | Ala | |
| 200 | | | | | 205 | | | | | 210 | | | | | 215 | |
| CTT | GGA | ATG | ACA | CTT | CTT | GGA | ATT | GTC | CCT | GAT | ACA | GAT | AAA | ATT | TAA | 3239 |
| Leu | Gly | Met | Thr | Leu | Leu | Gly | Ile | Val | Pro | Asp | Thr | Asp | Lys | Ile | * | |
| | | | | 220 | | | | | 225 | | | | | 230 | | |
| GGAGAAGAA | | ATG | CCT | TTA | TTA | AAG | TTA | GTT | AAA | TCA | AAA | GTA | GAC | TTT | | 3287 |
| | | Met | Pro | Leu | Leu | Lys | Leu | Val | Lys | Ser | Lys | Val | Asp | Phe | | |
| | | 1 | | | 5 | | | | | 10 | | | | | | |
| GCT | AAA | AAG | ACG | GAA | GAG | TAT | TAT | AAC | GCT | ATT | CGC | ACA | AAT | ATT | CAA | 3335 |
| Ala | Lys | Lys | Thr | Glu | Glu | Tyr | Tyr | Asn | Ala | Ile | Arg | Thr | Asn | Ile | Gln | |
| | 15 | | | | | 20 | | | | | 25 | | | | | |
| TTT | TCT | GGT | GCT | CAG | ATG | AAA | GTG | ATT | GCG | ATT | AGC | TCT | GTT | GAA | GCT | 3383 |
| Phe | Ser | Gly | Ala | Gln | Met | Lys | Val | Ile | Ala | Ile | Ser | Ser | Val | Glu | Ala | |
| 30 | | | | | 35 | | | | | 40 | | | | | 45 | |
| GGT | GAA | GGA | AAA | TCA | ATG | ATA | TCT | GTT | AAC | TTG | GCG | ATT | TCA | TTT | GCT | 3431 |
| Gly | Glu | Gly | Lys | Ser | Met | Ile | Ser | Val | Asn | Leu | Ala | Ile | Ser | Phe | Ala | |
| | | | | 50 | | | | | 55 | | | | | 60 | | |
| AGT | GTT | GGG | CTC | CGA | ACA | CTT | CTG | ATT | GAT | GCG | GAA | ACG | CGT | AAT | TCT | 3479 |
| Ser | Val | Gly | Leu | Arg | Thr | Leu | Leu | Ile | Asp | Ala | Glu | Thr | Arg | Asn | Ser | |
| | | | | 65 | | | | | 70 | | | | | 75 | | |
| GTT | TTG | TCA | GGT | ACA | TTT | AAA | TCA | AAT | GAG | CCT | TAT | AAA | GGT | CTT | TCA | 3527 |
| Val | Leu | Ser | Gly | Thr | Phe | Lys | Ser | Asn | Glu | Pro | Tyr | Lys | Gly | Leu | Ser | |
| | | | 80 | | | | | 85 | | | | | 90 | | | |
| AAT | TTC | CTT | TCA | GGA | AAT | GCC | GAT | CTA | AAT | GAA | ACG | ATT | TGC | CAA | ACT | 3575 |
| Asn | Phe | Leu | Ser | Gly | Asn | Ala | Asp | Leu | Asn | Glu | Thr | Ile | Cys | Gln | Thr | |
| | 95 | | | | | 100 | | | | | 105 | | | | | |
| GAT | ATT | TCT | GGT | TTA | GAT | GTT | ATT | GCA | TCT | GGT | CCT | GTT | CCA | CCT | AAT | 3623 |
| Asp | Ile | Ser | Gly | Leu | Asp | Val | Ile | Ala | Ser | Gly | Pro | Val | Pro | Pro | Asn | |
| 110 | | | | | 115 | | | | | 120 | | | | | 125 | |
| CCA | ACA | AGT | CTT | TTG | CAA | AAT | GAT | AAT | TTT | AGA | CAT | TTG | ATG | GAA | GTT | 3671 |
| Pro | Thr | Ser | Leu | Leu | Gln | Asn | Asp | Asn | Phe | Arg | His | Leu | Met | Glu | Val | |
| | | | | 130 | | | | | 135 | | | | | 140 | | |
| GCT | CGT | AGT | TGT | TAT | GAT | TAT | GTC | ATC | ATC | GAT | ACA | CCA | CCA | GTT | GGT | 3719 |
| Ala | Arg | Ser | Cys | Tyr | Asp | Tyr | Val | Ile | Ile | Asp | Thr | Pro | Pro | Val | Gly | |
| | | | 145 | | | | | 150 | | | | | 155 | | | |
| CTG | GTT | ATT | GAT | GCA | GTT | ATT | ATT | GCC | CAT | CAG | GCT | GAT | GCC | AGT | CTT | 3767 |
| Leu | Val | Ile | Asp | Ala | Val | Ile | Ile | Ala | His | Gln | Ala | Asp | Ala | Ser | Leu | |
| | | | 160 | | | | | 165 | | | | | 170 | | | |
| TTG | GTT | ACA | GAA | GCT | GGG | AAA | ATT | AAA | CGT | CGT | TTC | GTA | ACT | AAG | GCC | 3815 |
| Leu | Val | Thr | Glu | Ala | Gly | Lys | Ile | Lys | Arg | Arg | Phe | Val | Thr | Lys | Ala | |
| | | 175 | | | | | 180 | | | | | 185 | | | | |
| GTT | GAA | CAA | TTG | GTA | GAA | AGT | GGT | TCT | CAG | TTC | TTA | GGG | GTC | GTC | CTT | 3863 |
| Val | Glu | Gln | Leu | Val | Glu | Ser | Gly | Ser | Gln | Phe | Leu | Gly | Val | Val | Leu | |
| 190 | | | | | 195 | | | | | 200 | | | | | 205 | |

```
AAT AAA GTT GAC ATG ACA GTT GAT AAA TAT GGA TTT TAT GGT TCT TAC                    3911
Asn Lys Val Asp Met Thr Val Asp Lys Tyr Gly Phe Tyr Gly Ser Tyr
            210             215             220

GGA TCA TAT GGC GAG TAT GGA AAA AAA TCT GAC CAA AAA GAA GGT CAT                    3959
Gly Ser Tyr Gly Glu Tyr Gly Lys Lys Ser Asp Gln Lys Glu Gly His
        225             230             235

TCA AGA GCA CAT CGT CGT AGA AAA GTC GGT TGG AAT TAACGCGTTA                         4005
Ser Arg Ala His Arg Arg Arg Lys Val Gly Trp Asn
        240             245

GTGTGTTTTA AGATGTCGTT GGGAACGACA AGTGGAGGGA ATGAG ATG TCA CAA                      4059
                                             Met Ser Gln
                                              1

GCT AAA GAG GAA ATT TCA GAT GTT ATG ACT TAT TCA GAG CTA ACA AGT                    4107
Ala Lys Glu Glu Ile Ser Asp Val Met Thr Tyr Ser Glu Leu Thr Ser
      5             10              15

CAT AAG CCC AAA ATT ATT TAT AGC TTG ATT AAG CGG ATT GGT GAT ATT                    4155
His Lys Pro Lys Ile Ile Tyr Ser Leu Ile Lys Arg Ile Gly Asp Ile
 20              25              30              35

TTG GTT AGT TCT ATT GGT TTA ATT ATT TTG ATA CCG CTA TTT TTG ATA                    4203
Leu Val Ser Ser Ile Gly Leu Ile Ile Leu Ile Pro Leu Phe Leu Ile
              40              45              50

GTT GCT TTG ATC ATG AAA TGC TCT GAA CCA ACA GCA CCT ATA TTT TTC                    4251
Val Ala Leu Ile Met Lys Cys Ser Glu Pro Thr Ala Pro Ile Phe Phe
              55              60              65

TCA CAT ATT AGA AAT GGT AAA AAT GGC AAA AAG TTC AAA ATG TAT AAA                    4299
Ser His Ile Arg Asn Gly Lys Asn Gly Lys Lys Phe Lys Met Tyr Lys
 70              75              80

TTT AGA ACC ATG TGT CAG GAC GCA GAA TCG ATT TTG ATG AAA GAT ACG                    4347
Phe Arg Thr Met Cys Gln Asp Ala Glu Ser Ile Leu Met Lys Asp Thr
 85              90              95

GAA CTT TTT GCA AAA TTT AAG GCA AAT GGT TAT AAA CTT GAA ACG CAT                    4395
Glu Leu Phe Ala Lys Phe Lys Ala Asn Gly Tyr Lys Leu Glu Thr His
100             105             110             115

GAA GAT CCT AGA ATT ACA AAA ATC GGT GGC ATA TTA AGG AAA ACA AGT                    4443
Glu Asp Pro Arg Ile Thr Lys Ile Gly Gly Ile Leu Arg Lys Thr Ser
              120             125             130

ATT GAT GAA TTG CCA CAA CTG ATT AAT GTT TTT TTA GGA CAA ATG TCA                    4491
Ile Asp Glu Leu Pro Gln Leu Ile Asn Val Phe Leu Gly Gln Met Ser
              135             140             145

TTA GTG GGT CCA CGT CCA CTA CCA GAT AGA GAA ATC ATT GAA TAC GGT                    4539
Leu Val Gly Pro Arg Pro Leu Pro Asp Arg Glu Ile Ile Glu Tyr Gly
              150             155             160

GAT AAC CAA GAA AAA TTT TTA AGC GTT AAA CCA GGC ATG ACA GGA TGG                    4587
Asp Asn Gln Glu Lys Phe Leu Ser Val Lys Pro Gly Met Thr Gly Trp
 165             170             175

TGG CAA GTT TCA GGG AGA AGT ACT ATT GGG TAT CCT GAG CGG TGT CAT                    4635
Trp Gln Val Ser Gly Arg Ser Thr Ile Gly Tyr Pro Glu Arg Cys His
180             185             190             195

CTT GAG CTT TAT TAT GTA GAA AAG TGT TGT TTT ACT TTC GAT GTT CTT                    4683
Leu Glu Leu Tyr Tyr Val Glu Lys Cys Cys Phe Thr Phe Asp Val Leu
              200             205             210

ATA TTA CTT AAG ACA ATT GGG ATT GTT TTG AAG AGA GTT GGA GCG CGT                    4731
Ile Leu Leu Lys Thr Ile Gly Ile Val Leu Lys Arg Val Gly Ala Arg
              215             220             225

TAGTACTGAT GAAACAAAAA TTATTATTGA TAATAGAAGC GATGAGTGGT GGAGCCGGTC                  4791

GTCATGTACA AGACTTGATT AGTCATCTAC CTCAAGAAAA ATTTGATATT TATGTGATTT                  4851

ATTCAAATCA TAGAACAAAT CCTGTTTTTT GGAAAAAATA GTAACG ATG AAT GAG                     4906
                                                 Met Asn Glu
                                                  1
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| CAA | GTA | ACT | TTT | ATT | TTA | TGT | GAT | TTT | CTC | GTA | AGA | GAA | ATT | AAA | CCG | 4954 |
| Gln | Val | Thr | Phe | Ile | Leu | Cys | Asp | Phe | Leu | Val | Arg | Glu | Ile | Lys | Pro |      |
|     | 5   |     |     |     | 10  |     |     |     |     | 15  |     |     |     |     |     |      |
| AAA | TAT | GAT | TTG | CTT | GCT | TAT | CAA | TTT | ATT | TCT | AAA | AAG | ATT | AAA | GAA | 5002 |
| Lys | Tyr | Asp | Leu | Leu | Ala | Tyr | Gln | Phe | Ile | Ser | Lys | Lys | Ile | Lys | Glu |      |
| 20  |     |     |     |     | 25  |     |     |     |     | 30  |     |     |     |     | 35  |      |
| ATC | AAA | CCA | GAT | ATT | GTA | CAT | TGT | CAC | AGT | TCA | AAA | GCT | GGT | GTT | ATT | 5050 |
| Ile | Lys | Pro | Asp | Ile | Val | His | Cys | His | Ser | Ser | Lys | Ala | Gly | Val | Ile |      |
|     |     |     |     | 40  |     |     |     |     | 45  |     |     |     |     | 50  |     |      |
| GGT | CGT | TTA | GCT | GCC | AAA | AGA | CGA | GGT | GTT | AAA | AAA | ATA | TTT | TAT | ACG | 5098 |
| Gly | Arg | Leu | Ala | Ala | Lys | Arg | Arg | Gly | Val | Lys | Lys | Ile | Phe | Tyr | Thr |      |
|     |     |     | 55  |     |     |     |     | 60  |     |     |     |     | 65  |     |     |      |
| CCA | CAT | GCT | TAT | TCG | TTT | TTG | GCA | CCT | GAA | TTT | AGT | GGG | AAG | AAA | AAG | 5146 |
| Pro | His | Ala | Tyr | Ser | Phe | Leu | Ala | Pro | Glu | Phe | Ser | Gly | Lys | Lys | Lys |      |
|     |     | 70  |     |     |     |     | 75  |     |     |     |     | 80  |     |     |     |      |
| TTT | CTA | TTT | GTT | CAA | ATT | GAA | AAG | TTT | TTA | AGC | CGA | TTT | GCG | ACA | ACT | 5194 |
| Phe | Leu | Phe | Val | Gln | Ile | Glu | Lys | Phe | Leu | Ser | Arg | Phe | Ala | Thr | Thr |      |
|     | 85  |     |     |     |     | 90  |     |     |     |     | 95  |     |     |     |     |      |
| AAG | ATA | TTT | TGT | GTG | TCA | ATA | GCG | GAA | ATG | CAA | GCT | GCT | CTT | GAA | GTA | 5242 |
| Lys | Ile | Phe | Cys | Val | Ser | Ile | Ala | Glu | Met | Gln | Ala | Ala | Leu | Glu | Val |      |
| 100 |     |     |     |     | 105 |     |     |     |     | 110 |     |     |     |     | 115 |      |
| AAT | CTA | GAT | AAA | ACC | GAT | AAG | TTT | CAG | GTA | ATT | TAT | AAT | GGT | TTG | CCA | 5290 |
| Asn | Leu | Asp | Lys | Thr | Asp | Lys | Phe | Gln | Val | Ile | Tyr | Asn | Gly | Leu | Pro |      |
|     |     |     |     | 120 |     |     |     |     | 125 |     |     |     |     | 130 |     |      |
| GAA | ATT | GAT | TTA | CCA | AGC | AAA | GAA | ACG | ATT | CGG | GCG | CAA | TTA | GGA | CTG | 5338 |
| Glu | Ile | Asp | Leu | Pro | Ser | Lys | Glu | Thr | Ile | Arg | Ala | Gln | Leu | Gly | Leu |      |
|     |     |     | 135 |     |     |     |     | 140 |     |     |     |     | 145 |     |     |      |
| GAA | AAG | GCA | GCA | GTT | GTT | ATA | GGC | AAT | AAT | GCA | AAA | ATG | TCG | GAA | CAG | 5386 |
| Glu | Lys | Ala | Ala | Val | Val | Ile | Gly | Asn | Asn | Ala | Lys | Met | Ser | Glu | Gln |      |
|     |     | 150 |     |     |     |     | 155 |     |     |     |     | 160 |     |     |     |      |
| AAA | AAT | CCT | ATG | TTT | TTT | ATG | GAA | ATT | GCC | CGA | AAA | ATG | ATT | AGA | CAA | 5434 |
| Lys | Asn | Pro | Met | Phe | Phe | Met | Glu | Ile | Ala | Arg | Lys | Met | Ile | Arg | Gln |      |
| 165 |     |     |     |     | 170 |     |     |     |     | 175 |     |     |     |     |     |      |
| AAC | GCA | AAT | TGG | CAT | TTT | GTG | TGG | GTA | GGT | GAT | GGT | CAG | CTG | ATG | CCA | 5482 |
| Asn | Ala | Asn | Trp | His | Phe | Val | Trp | Val | Gly | Asp | Gly | Gln | Leu | Met | Pro |      |
| 180 |     |     |     |     | 185 |     |     |     |     | 190 |     |     |     |     | 195 |      |
| CTT | TTT | CAA | TCA | TTT | ATT | AAG | CAA | AAT | GGA | CTA | GAG | GGA | AAT | ATC | CAT | 5530 |
| Leu | Phe | Gln | Ser | Phe | Ile | Lys | Gln | Asn | Gly | Leu | Glu | Gly | Asn | Ile | His |      |
|     |     |     |     | 200 |     |     |     |     | 205 |     |     |     |     | 210 |     |      |
| TTG | CTT | GGC | GAG | CGT | CCT | GAT | AGT | GAA | ATA | GTT | GTG | ACA | GCC | TAT | GAC | 5578 |
| Leu | Leu | Gly | Glu | Arg | Pro | Asp | Ser | Glu | Ile | Val | Val | Thr | Ala | Tyr | Asp |      |
|     |     |     | 215 |     |     |     |     | 220 |     |     |     |     | 225 |     |     |      |
| ATC | TTC | TTG | ACG | ACT | TCC | CAA | TAT | GAA | GGT | TTA | CCT | TAT | GCA | CCA | ATT | 5626 |
| Ile | Phe | Leu | Thr | Thr | Ser | Gln | Tyr | Glu | Gly | Leu | Pro | Tyr | Ala | Pro | Ile |      |
|     |     | 230 |     |     |     |     | 235 |     |     |     |     | 240 |     |     |     |      |
| GAA | GCG | ATG | CGA | GCT | GGT | GTC | CCG | ATT | CTT | GCG | ACA | AAA | GTT | GTT | GGC | 5674 |
| Glu | Ala | Met | Arg | Ala | Gly | Val | Pro | Ile | Leu | Ala | Thr | Lys | Val | Val | Gly |      |
|     | 245 |     |     |     |     | 250 |     |     |     |     | 255 |     |     |     |     |      |
| AAT | AGT | GAG | CTT | GTG | ATA | GAG | GGC | AAA | AAT | GGT | TAT | TTG | ATT | GAC | TTA | 5722 |
| Asn | Ser | Glu | Leu | Val | Ile | Glu | Gly | Lys | Asn | Gly | Tyr | Leu | Ile | Asp | Leu |      |
| 260 |     |     |     |     | 265 |     |     |     |     | 270 |     |     |     |     | 275 |      |
| GAG | TGG | TCA | AAA | TCT | GTC | GAA | GAA | AAA | TTA | TAT | AAG | GCA | GCG | AAA | ATA | 5770 |
| Glu | Trp | Ser | Lys | Ser | Val | Glu | Glu | Lys | Leu | Tyr | Lys | Ala | Ala | Lys | Ile |      |
|     |     |     |     | 280 |     |     |     |     | 285 |     |     |     |     | 290 |     |      |
| GAT | GCA | CAA | ATG | ATT | AAA | GCA | GAT | TTT | AGG | CAA | AGG | TTT | GCG | ATT | GAT | 5818 |
| Asp | Ala | Gln | Met | Ile | Lys | Ala | Asp | Phe | Arg | Gln | Arg | Phe | Ala | Ile | Asp |      |
|     |     |     | 295 |     |     |     |     | 300 |     |     |     |     | 305 |     |     |      |
| CAG | ATA | TTA | AAG | CAA | ATT | GAA | ACA | ATT | TAT | TTA | GCT | TGAATGAAGA |   |   |   | 5864 |
| Gln | Ile | Leu | Lys | Gln | Ile | Glu | Thr | Ile | Tyr | Leu | Ala |     |     |     |     |      |
|     |     | 310 |     |     |     |     | 315 |     |     |     |     |     |     |     |     |      |

-continued

| | |
|---|---|
| ATGAGGAGGC ATAAATGCTG ATTTTGAAAT TAAAATTTCA TCTTAATTGG TACACAAACG | 5924 |
| AAAACCATTA TTACACGTGA GTATTCGAAG ACCTGGAAAC GAGGCGATGA GCCGTATTAT | 5984 |
| CCAGTGAACA ATGATCGTAA CAACAAACTC TATACTGCCT ATAAGCGTCT TGCCGAGCAA | 6044 |
| CAAGAGAATG TCATTTTCGG TGGACGTCTA GGTCACTACC GTTACTACGA TATGCACCAG | 6104 |
| GTAATTGGAG CTGCCTTGCA GTGTGTCAGA AATGAAGTGA AGTAAATCTT GATGAAGTTG | 6164 |
| AATAACTTTA AGTAATTTTA TACTTAATCC AATTGATGAA AATATTTTG TATCGATTTA | 6224 |
| TCTTCTGTAA GAAGAGTCCT AATCGTTTAA AAAATGTACA ATTGAGTTTT TATATTTTA | 6284 |
| AATAAAGTTA CTTTTAAGTC GTGTTATAGA ATATACATGA ATAGGTGTAT TAGAAAATTT | 6344 |
| ATTAATCTAA TCCTCGAAAA TAACTGACTG TAAGGAATCA AGTTGTGGAG TGTAAGTTGT | 6404 |
| CAAATGGAGA GGAAAATAAT ATG AAA AAA ATT TCA ATT TTA CAC TTT TCC | 6454 |
|                                     Met Lys Lys Ile Ser Ile Leu His Phe Ser<br>                                     1            5                        10 | |
| CAA GTA TCA GGC GGG GGA GTT GAA AAG TAC ATA AAA TTA TTT TTA AAG<br>Gln Val Ser Gly Gly Gly Val Glu Lys Tyr Ile Lys Leu Phe Leu Lys<br>              15                 20                 25 | 6502 |
| TAT TCT GAT GTG ACA AAA TTT AAT AAT TAT TTA GTT GCA CCT AAT CTT<br>Tyr Ser Asp Val Thr Lys Phe Asn Asn Tyr Leu Val Ala Pro Asn Leu<br>          30                       35                 40 | 6550 |
| GAA AAT TAT GAC GAA TTT AAT GGA TAT TTA AAG ATG TCT GTC AAT TTT<br>Glu Asn Tyr Asp Glu Phe Asn Gly Tyr Leu Lys Met Ser Val Asn Phe<br>        45                         50                 55 | 6598 |
| AAT ATG GAA CAA ACT TTT TCT CCG CTA AAA ATA TTC AAA AAT GTC TTT<br>Asn Met Glu Gln Thr Phe Ser Pro Leu Lys Ile Phe Lys Asn Val Phe<br>    60                       65                 70 | 6646 |
| TTT ATT CGT AGT GTA CTC AAA AAA ATA AAC CCA GAT ATA GTA TAC CTA<br>Phe Ile Arg Ser Val Leu Lys Lys Ile Asn Pro Asp Ile Val Tyr Leu<br>75                     80                       85                 90 | 6694 |
| CAT AGT ACA TTT GCA GGT GTC GTA GGT CGT ATT GCT TCA ATA GGT TTG<br>His Ser Thr Phe Ala Gly Val Val Gly Arg Ile Ala Ser Ile Gly Leu<br>              95                      100                    105 | 6742 |
| CCA ACA AAA GTA GTA TAC AAT CCT CAC GGA TGG TCC TTC AAA ATG GAC<br>Pro Thr Lys Val Val Tyr Asn Pro His Gly Trp Ser Phe Lys Met Asp<br>          110                       115                    120 | 6790 |
| AAC AGC TAT TTG AAA AAG CTT ATT TTT AAA TTA ATC GAA TTT TCT TTA<br>Asn Ser Tyr Leu Lys Lys Leu Ile Phe Lys Leu Ile Glu Phe Ser Leu<br>             125                  130                    135 | 6838 |
| TCT TTT TTA ACT GAT AAG TTT ATT TTA ATT TCG GAA TCT GAG TAT ATT<br>Ser Phe Leu Thr Asp Lys Phe Ile Leu Ile Ser Glu Ser Glu Tyr Ile<br>    140                      145                    150 | 6886 |
| TTG GCT AAC CAT ATT TCA TTT AAT AAA AGC AAG TTT TCA CTA ATT AAT<br>Leu Ala Asn His Ile Ser Phe Asn Lys Ser Lys Phe Ser Leu Ile Asn<br>155                     160                       165                    170 | 6934 |
| AAT GGT GTT GAA GTG ATT ACA GGG GAT TCA AGA AAT GAG ATA GAA GAG<br>Asn Gly Val Glu Val Ile Thr Gly Asp Ser Arg Asn Glu Ile Glu Glu<br>                175                       180                    185 | 6982 |
| ATA TTT CCA AAT GAG GAT TTT ATA ATT GGC ATG GTT GGC AGA CTA AGC<br>Ile Phe Pro Asn Glu Asp Phe Ile Ile Gly Met Val Gly Arg Leu Ser<br>          190                       195                    200 | 7030 |
| CCA CCC AAA GAG TTT TTC TTT TTT ATT GAT TTT GCA AAA AAA ATA TTA<br>Pro Pro Lys Glu Phe Phe Phe Phe Ile Asp Phe Ala Lys Lys Ile Leu<br>       205                      210                    215 | 7078 |
| CAA ATT CGA AAC GAT ACC AAT TTT ATT ATC GTG GGT GAT GGA GAG TTA<br>Gln Ile Arg Asn Asp Thr Asn Phe Ile Ile Val Gly Asp Gly Glu Leu<br>    220                       225                    230 | 7126 |
| CGA AGT GAA ATA GAA AGA ATG ATA CTA GAT AAT GGG TTA GGA GAT AAA<br>Arg Ser Glu Ile Glu Arg Met Ile Leu Asp Asn Gly Leu Gly Asp Lys | 7174 |

-continued

| | | | | | | | | | | | | | | | | |
|---|---|---|---|---|---|---|---|---|---|---|---|---|---|---|---|---|
| 235 | | | | | 240 | | | | | 245 | | | | | 250 | |
| ATC | TAT | ATT | ACT | GGG | TGG | GTT | GAT | AAT | CCG | AGA | AAC | TAT | ATA | GAG | AAG | 7222 |
| Ile | Tyr | Ile | Thr | Gly | Trp | Val | Asp | Asn | Pro | Arg | Asn | Tyr | Ile | Glu | Lys | |
| | | | | 255 | | | | | 260 | | | | | 265 | | |
| TTT | GAT | CAA | GCT | ATT | CTG | TTT | TCT | AGA | TGG | GAG | GGT | CTT | AGC | CTA | ACG | 7270 |
| Phe | Asp | Gln | Ala | Ile | Leu | Phe | Ser | Arg | Trp | Glu | Gly | Leu | Ser | Leu | Thr | |
| | | | 270 | | | | | 275 | | | | | 280 | | | |
| ATT | GCG | GAA | TAT | ATG | TCT | CAG | AAG | AAA | ACA | ATT | TTA | GCA | ACA | AAT | ATT | 7318 |
| Ile | Ala | Glu | Tyr | Met | Ser | Gln | Lys | Lys | Thr | Ile | Leu | Ala | Thr | Asn | Ile | |
| | | 285 | | | | | 290 | | | | | 295 | | | | |
| GGT | GGC | ATT | AAT | GAT | TTA | ATC | ACT | GAT | GGT | GAA | ACA | GGA | ATG | CTG | ATT | 7366 |
| Gly | Gly | Ile | Asn | Asp | Leu | Ile | Thr | Asp | Gly | Glu | Thr | Gly | Met | Leu | Ile | |
| | 300 | | | | | 305 | | | | | 310 | | | | | |
| GAA | GTT | GGA | GAC | TTG | AAT | TCA | GCA | GTA | TCT | AAA | TCT | TTC | GAG | CTA | AGA | 7414 |
| Glu | Val | Gly | Asp | Leu | Asn | Ser | Ala | Val | Ser | Lys | Ser | Phe | Glu | Leu | Arg | |
| 315 | | | | | 320 | | | | | 325 | | | | | 330 | |
| AAT | AAT | AAA | GAG | GTT | TCG | AAT | CAA | TTA | GCG | AAT | AAC | GCT | TAT | AAT | AAA | 7462 |
| Asn | Asn | Lys | Glu | Val | Ser | Asn | Gln | Leu | Ala | Asn | Asn | Ala | Tyr | Asn | Lys | |
| | | | | 335 | | | | | 340 | | | | | 345 | | |
| GTT | GTT | GAA | CAG | TTT | TCG | ATT | GAA | AAA | CAG | ATG | GCT | GAG | ATA | GAA | AGT | 7510 |
| Val | Val | Glu | Gln | Phe | Ser | Ile | Glu | Lys | Gln | Met | Ala | Glu | Ile | Glu | Ser | |
| | | | 350 | | | | | 355 | | | | | 360 | | | |
| TTA | TTT | ATA | GAG | ATG | TGT | AAC | AAT | GAG | AAA | TAGAGACTTA | | | | AAGAAAATAC | | 7560 |
| Leu | Phe | Ile | Glu | Met | Cys | Asn | Asn | Glu | Lys | | | | | | | |
| | | 365 | | | | | 370 | | | | | | | | | |
| AGGTTATTTG | | ATTGACTTAG | | AGTGGTCAAA | | ATCTGTCGAA | | GAAAAATTAT | | ATAAGGCAGC | | | | | | 7620 |
| GAAATGGAT | | GCACAAATGA | | TTAAAGCAGA | | TTTAGGCAA | | AGGTTTGCGA | | TTGATCAGAT | | | | | | 7680 |
| GTTAAAGCAA | | ATTAAAACAA | | TTTATTTAGC | | TTGAATGAAG | | AAAGAGGAGG | | CATAA ATG | | | | | | 7738 |
| | | | | | | | | | | | | | | | Met | |
| | | | | | | | | | | | | | | | 1 | |
| CTG | ATT | TTG | AAA | TTA | AAA | TTT | CAT | CTT | AAA | TCG | TTA | TTC | CTT | AAA | TGG | 7786 |
| Leu | Ile | Leu | Lys | Leu | Lys | Phe | His | Leu | Lys | Ser | Leu | Phe | Leu | Lys | Trp | |
| | | | 5 | | | | | 10 | | | | | 15 | | | |
| ATT | TAT | CGA | TTA | CTT | TAT | CTA | AAA | AAG | TTT | CAG | TTT | GGT | GCA | CGC | TTG | 7834 |
| Ile | Tyr | Arg | Leu | Leu | Tyr | Leu | Lys | Lys | Phe | Gln | Phe | Gly | Ala | Arg | Leu | |
| | | 20 | | | | | 25 | | | | | 30 | | | | |
| ACG | TTT | CGA | GAT | GGG | TTT | CAT | TTG | TTA | ATT | GAA | AAA | TCT | GGG | AAA | GTT | 7882 |
| Thr | Phe | Arg | Asp | Gly | Phe | His | Leu | Leu | Ile | Glu | Lys | Ser | Gly | Lys | Val | |
| | 35 | | | | | 40 | | | | | 45 | | | | | |
| ATC | ATC | GGG | AAT | CAT | GTT | TTT | TTT | AAT | AAC | TTT | TGT | TCA | ATT | AAT | GCC | 7930 |
| Ile | Ile | Gly | Asn | His | Val | Phe | Phe | Asn | Asn | Phe | Cys | Ser | Ile | Asn | Ala | |
| 50 | | | | | 55 | | | | | 60 | | | | | 65 | |
| ATG | TTA | TCA | GTA | ACG | ATT | GGT | GAT | GAC | TGT | ATT | TTT | GGT | GAA | AAC | GTT | 7978 |
| Met | Leu | Ser | Val | Thr | Ile | Gly | Asp | Asp | Cys | Ile | Phe | Gly | Glu | Asn | Val | |
| | | | | 70 | | | | | 75 | | | | | 80 | | |
| AAA | ATT | TAT | GAT | CAC | AAT | CAT | TGT | TAT | CAA | AAT | AAA | AGT | CAA | CCT | ATT | 8026 |
| Lys | Ile | Tyr | Asp | His | Asn | His | Cys | Tyr | Gln | Asn | Lys | Ser | Gln | Pro | Ile | |
| | | | 85 | | | | | 90 | | | | | 95 | | | |
| TCA | AAA | CAA | GGT | TTT | TCA | ACT | GCT | GCT | ATC | CAG | ATT | GGT | CGT | AAC | TGT | 8074 |
| Ser | Lys | Gln | Gly | Phe | Ser | Thr | Ala | Ala | Ile | Gln | Ile | Gly | Arg | Asn | Cys | |
| | | 100 | | | | | 105 | | | | | 110 | | | | |
| TGG | ATA | GGT | AGT | CAA | GTG | ACG | ATT | TTA | AAA | GGT | GTA | ACC | ATA | GGT | GAT | 8122 |
| Trp | Ile | Gly | Ser | Gln | Val | Thr | Ile | Leu | Lys | Gly | Val | Thr | Ile | Gly | Asp | |
| | 115 | | | | | 120 | | | | | 125 | | | | | |
| AAT | AGT | ATC | ATT | GGT | GCT | GGT | GTG | GTA | GTT | TAT | CAA | GAT | GTG | CCA | GAA | 8170 |
| Asn | Ser | Ile | Ile | Gly | Ala | Gly | Val | Val | Val | Tyr | Gln | Asp | Val | Pro | Glu | |
| 130 | | | | 135 | | | | | 140 | | | | | 145 | | |
| AAT | TCG | ATT | GTT | TTA | TCT | AAT | GGA | GAA | ATT | AGA | AAG | CGT | GGC | | | 8212 |
| Asn | Ser | Ile | Val | Leu | Ser | Asn | Gly | Glu | Ile | Arg | Lys | Arg | Gly | | | |

-continued

```
                                        150                           155
TAATTAAA ATG TAT CTT AAA AGT CTA ATC TCT ATT GTT ATT CCA GTA TAT                  8262
        Met Tyr Leu Lys Ser Leu Ile Ser Ile Val Ile Pro Val Tyr
          1               5                      10

AAT GTA GAG AAA TAT TTA GAA AAA TGT TTG CAA TCT GTT CAA AAT CAG                   8310
Asn Val Glu Lys Tyr Leu Glu Lys Cys Leu Gln Ser Val Gln Asn Gln
 15              20                  25                  30

ACT TAC AAT AAT TTT GAA GTG ATT TTA GTG AAT GAT GGC TCA ACC GAT                   8358
Thr Tyr Asn Asn Phe Glu Val Ile Leu Val Asn Asp Gly Ser Thr Asp
                 35                  40                  45

TCA TCA CTT TCA ATA TGC GAA AAA TTT GTT AAT CAG GAT AAA AGA TTT                   8406
Ser Ser Leu Ser Ile Cys Glu Lys Phe Val Asn Gln Asp Lys Arg Phe
         50                  55                  60

TCT GTT TTT TCT AAA GAA AAT GGT GGT ATG TCA TCT GCA CGA AAT TTT                   8454
Ser Val Phe Ser Lys Glu Asn Gly Gly Met Ser Ser Ala Arg Asn Phe
         65                  70                  75

GGA ATT AAA AAG GCT AAA GGA TCG TTT ATC ACA TTT GTA GAT AGT GAT                   8502
Gly Ile Lys Lys Ala Lys Gly Ser Phe Ile Thr Phe Val Asp Ser Asp
     80                  85                  90

GAC TAC ATA GTA AAA GAT TAT CTT TCT CAT TTG GTA GCT GGG ATA AAA                   8550
Asp Tyr Ile Val Lys Asp Tyr Leu Ser His Leu Val Ala Gly Ile Lys
 95              100                 105                 110

AGT GAG ACC TCT ATA GTT TGT TCA AAG TTT TTT CTT GTA GAT GAA AAA                   8598
Ser Glu Thr Ser Ile Val Cys Ser Lys Phe Phe Leu Val Asp Glu Lys
                 115                 120                 125

GGA AGT TTA TTG ACT AAA AAA GAG GCA CCT AAA AAG AAA TCA GAA GTC                   8646
Gly Ser Leu Leu Thr Lys Lys Glu Ala Pro Lys Lys Lys Ser Glu Val
             130                 135                 140

GTT TCA ATT GAG GAA AGT ATT AAA ATT CTT CTG TTG CAA CAA AAT GGC                   8694
Val Ser Ile Glu Glu Ser Ile Lys Ile Leu Leu Leu Gln Gln Asn Gly
         145                 150                 155

TAT GAT CTC GCT GTC TGG GGA AAA TTA TAC CCC GTT TCT TTC TTT GAA                   8742
Tyr Asp Leu Ala Val Trp Gly Lys Leu Tyr Pro Val Ser Phe Phe Glu
     160                 165                 170

ACA ATT TCT TTC CCA GAA GGA AAA CTT TAC GAA GAT ATG GGA ACA ACT                   8790
Thr Ile Ser Phe Pro Glu Gly Lys Leu Tyr Glu Asp Met Gly Thr Thr
175                 180                 185                 190

TAC AAA TTA CTA AAA TTG GCA AGT GAA GTG GTC TTC TTG GAT GCG TAT                   8838
Tyr Lys Leu Leu Lys Leu Ala Ser Glu Val Val Phe Leu Asp Ala Tyr
                 195                 200                 205

GAT TAT GCC TAC GTA CAG CGA CCT AAT AGT ATC ATG AAT AGT TCT TTT                   8886
Asp Tyr Ala Tyr Val Gln Arg Pro Asn Ser Ile Met Asn Ser Ser Phe
             210                 215                 220

AAT TTG AAA AAG TTG GAT ATA ATA GAA ATG GTT CAT GAA ATG GAA AAC                   8934
Asn Leu Lys Lys Leu Asp Ile Ile Glu Met Val His Glu Met Glu Asn
         225                 230                 235

GAT ATA TTA GCA CAG TTT CCA AAT TTA GCA TTA TAT GTT AAG AAT CGA                   8982
Asp Ile Leu Ala Gln Phe Pro Asn Leu Ala Leu Tyr Val Lys Asn Arg
     240                 245                 250

GCA TTT GCC GCG GAA GTG AAA ATC TTT TTA GAG ATT CCA AAA GAA AAA                   9030
Ala Phe Ala Ala Glu Val Lys Ile Phe Leu Glu Ile Pro Lys Glu Lys
255                 260                 265                 270

GAA TTT GAG CAA GCG CAA AAG CAA CTT TGG CAT GAT ATC AAA AAG AAT                   9078
Glu Phe Glu Gln Ala Gln Lys Gln Leu Trp His Asp Ile Lys Lys Asn
                 275                 280                 285

AGA AAA GCA CCA TTT ATG ACA AAA GGT GCT AGA TTG AAG AAT AGG CTC                   9126
Arg Lys Ala Pro Phe Met Thr Lys Gly Ala Arg Leu Lys Asn Arg Leu
             290                 295                 300

GGA GCT AGT CTG TCG TTT TTA GGT AAA TCT TTA TTT TTG ACT ATT GGG                   9174
Gly Ala Ser Leu Ser Phe Leu Gly Lys Ser Leu Phe Leu Thr Ile Gly
```

|  |  |  |  |  |  |  | 305 |  |  |  |  | 310 |  |  |  |  | 315 |  |  |  |
|---|---|---|---|---|---|---|---|---|---|---|---|---|---|---|---|---|---|---|---|---|

```
AAG CAG TTA GTA GAT AGA TAATGATATT GAAAGCGATA CGATACAATC                                9222
Lys Gln Leu Val Asp Arg
            320

GTAAACTTCT TTTGGTGTTG ACTAGGAGTT AGCTTGAAAT TTGAATATAA AGGAAGCAAC                       9282

AC ATG GTA ATT TAT TTT TTA CTT TTC CCG ATG ATC GCA ATG ATT TAT                          9329
   Met Val Ile Tyr Phe Leu Leu Phe Pro Met Ile Ala Met Ile Tyr
    1               5                  10                  15

TTA ATG ACA TTG CTC TTA CGG CAA AAA GCA CAA ATC CAA AAA ACG ATT                         9377
Leu Met Thr Leu Leu Leu Arg Gln Lys Ala Gln Ile Gln Lys Thr Ile
                20                  25                  30

TTT TGT GTT CTT ACG TTT GGT ACA CTA GGC TTT ATT TCA GCA AGT CGT                         9425
Phe Cys Val Leu Thr Phe Gly Thr Leu Gly Phe Ile Ser Ala Ser Arg
                35                  40                  45

GCA TCA AGT GTT GGG ACG GAC GTT ACT TTA TAC GAA AAT ATT TTT AAA                         9473
Ala Ser Ser Val Gly Thr Asp Val Thr Leu Tyr Glu Asn Ile Phe Lys
                50                  55                  60

TCT ATA AAT TAC GGG ATA AGT GCT GAG AAT AAT TGG GGA TAC GTC ATC                         9521
Ser Ile Asn Tyr Gly Ile Ser Ala Glu Asn Asn Trp Gly Tyr Val Ile
            65                  70                  75

TAT AAC AAG CTG ATT GGT AGT GTA TTT GGC TAT ACA GGA CAT GAA ATC                         9569
Tyr Asn Lys Leu Ile Gly Ser Val Phe Gly Tyr Thr Gly His Glu Ile
 80                  85                  90                  95

ACG GCC GCT AAT TCA GTT TTG ATT ACA ATA CTT ATT GGT ATT TTT ATT                         9617
Thr Ala Ala Asn Ser Val Leu Ile Thr Ile Leu Ile Gly Ile Phe Ile
                100                 105                 110

TGG AAA GTA GCG GAA CAT TAT TTT GTT GCG ACG TTT TTA TAC ATT AGC                         9665
Trp Lys Val Ala Glu His Tyr Phe Val Ala Thr Phe Leu Tyr Ile Ser
                115                 120                 125

TTG TTT TAT TAT GCT ACA AGT TTT AAT ATT TCA AGA CAA TTT ATT GCC                         9713
Leu Phe Tyr Tyr Ala Thr Ser Phe Asn Ile Ser Arg Gln Phe Ile Ala
            130                 135                 140

ATG GGG CTT GTA TTG GTA GCA ATT TCT TTT GCT TTA GAT AAA AAG GTT                         9761
Met Gly Leu Val Leu Val Ala Ile Ser Phe Ala Leu Asp Lys Lys Val
145                 150                 155

ATG CCT TGG TTT ATC TTG ACA GTT TTG GCT ACC TTA TTT CAT GCG ACA                         9809
Met Pro Trp Phe Ile Leu Thr Val Leu Ala Thr Leu Phe His Ala Thr
160                 165                 170                 175

GCA ATC GTT GCT TTT CCT GTC TAT TGG CTT ACA AAA GTA CAT TGG GAT                         9857
Ala Ile Val Ala Phe Pro Val Tyr Trp Leu Thr Lys Val His Trp Asp
                180                 185                 190

GTG AAA AAG ACA TTA AGT ATT TTT CCA ATC ACG ATT TTT GCA AGT TTT                         9905
Val Lys Lys Thr Leu Ser Ile Phe Pro Ile Thr Ile Phe Ala Ser Phe
                195                 200                 205

ATT TTT GAT GCT ATT TTA AAC ATT TTT GTA CGT TTT TTC CCA CAT TAT                         9953
Ile Phe Asp Ala Ile Leu Asn Ile Phe Val Arg Phe Phe Pro His Tyr
                210                 215                 220

GAG ATG TAT ATC ACT GGA ACA CAA TTT AAT ATT TCA GAT CAG GGG CAG                         10001
Glu Met Tyr Ile Thr Gly Thr Gln Phe Asn Ile Ser Asp Gln Gly Gln
                225                 230                 235

GGA CGT GTG GTT TTG GTC AAA ATA TTT ATC TTG CTC ATT TTG TTT ACT                         10049
Gly Arg Val Val Leu Val Lys Ile Phe Ile Leu Leu Ile Leu Phe Thr
240                 245                 250                 255

TTA TTC TTG TTT TAT AAA AAA AGC TAT GCT TTG ATT TCT GAA TGT CAT                         10097
Leu Phe Leu Phe Tyr Lys Lys Ser Tyr Ala Leu Ile Ser Glu Cys His
                260                 265                 270

CAA AGT TTG ATA GCT TTG ACA ACC GTT GGA TTA AGT ATC GGT ATT GTA                         10145
Gln Ser Leu Ile Ala Leu Thr Thr Val Gly Leu Ser Ile Gly Ile Val
                275                 280                 285
```

-continued

| | | | | | | | | | | | | | | | | |
|---|---|---|---|---|---|---|---|---|---|---|---|---|---|---|---|---|
| TTT | TAT | AAT | AAT | ATT | TTA | CTC | AAT | AGA | ATA | GAA | ATG | TTT | TAT | TCA | ATT | 10193 |
| Phe | Tyr | Asn | Asn | Ile | Leu | Leu | Asn | Arg | Ile | Glu | Met | Phe | Tyr | Ser | Ile | |
| | | 290 | | | | 295 | | | | | 300 | | | | | |
| TTA | AGC | ATC | GTA | TTT | ATT | CCA | ATT | GCT | ATA | GAT | TAC | ATT | AGT | TTG | AAA | 10241 |
| Leu | Ser | Ile | Val | Phe | Ile | Pro | Ile | Ala | Ile | Asp | Tyr | Ile | Ser | Leu | Lys | |
| | 305 | | | | 310 | | | | | 315 | | | | | | |
| TTT | AAA | CAA | AAA | GAT | GCT | GTG | CGA | CTA | ATG | CTG | ACG | ATA | GGT | ATT | TTG | 10289 |
| Phe | Lys | Gln | Lys | Asp | Ala | Val | Arg | Leu | Met | Leu | Thr | Ile | Gly | Ile | Leu | |
| 320 | | | | 325 | | | | | 330 | | | | | 335 | | |
| TTA | ATT | ACA | CTT | GTG | CCT | TAC | TAT | ATA | CAG | GTT | AGC | GGT | AAT | TAT | TCA | 10337 |
| Leu | Ile | Thr | Leu | Val | Pro | Tyr | Tyr | Ile | Gln | Val | Ser | Gly | Asn | Tyr | Ser | |
| | | | 340 | | | | | 345 | | | | | 350 | | | |
| GGA | ATA | TTG | CCT | TAT | GTT | ATT | CAA | CAA | TAAAAAATAA | | AGTTTAGAGA | | | | | 10384 |
| Gly | Ile | Leu | Pro | Tyr | Val | Ile | Gln | Gln | | | | | | | | |
| | | 355 | | | | | 360 | | | | | | | | | |
| GGAAATA | ATG | GAG | GAT | AGA | AAG | AAA | CAA | GTA | ATT | TTG | ATA | CTA | TCC | CAC | | 10433 |
| | Met | Glu | Asp | Arg | Lys | Lys | Gln | Val | Ile | Leu | Ile | Leu | Ser | His | | |
| | 1 | | | | 5 | | | | | 10 | | | | | | |
| AGA | AAT | ACT | CTC | GCT | CTA | AAA | TCA | ACA | ATA | GAG | CTT | TTG | GAT | TCT | CAA | 10481 |
| Arg | Asn | Thr | Leu | Ala | Leu | Lys | Ser | Thr | Ile | Glu | Leu | Leu | Asp | Ser | Gln | |
| 15 | | | | 20 | | | | | 25 | | | | | 30 | | |
| TAC | TTT | GAT | TTC | TTT | CTT | CAT | ATA | GAT | AAA | AAA | AGT | AGA | ATT | CAA | GAT | 10529 |
| Tyr | Phe | Asp | Phe | Phe | Leu | His | Ile | Asp | Lys | Lys | Ser | Arg | Ile | Gln | Asp | |
| | | | | 35 | | | | 40 | | | | | 45 | | | |
| TTT | TTT | TAT | TTA | AAA | AAA | ATT | ACA | AAA | TTC | TCC | ACT | ATT | CAT | TTT | TCA | 10577 |
| Phe | Phe | Tyr | Leu | Lys | Lys | Ile | Thr | Lys | Phe | Ser | Thr | Ile | His | Phe | Ser | |
| | | | 50 | | | | 55 | | | | | 60 | | | | |
| GAA | AGA | AAA | AAT | GTA | CAT | TGG | GGA | GGT | TTT | TCT | ATG | GTA | GAA | GCA | ATG | 10625 |
| Glu | Arg | Lys | Asn | Val | His | Trp | Gly | Gly | Phe | Ser | Met | Val | Glu | Ala | Met | |
| | 65 | | | | 70 | | | | | 75 | | | | | | |
| TTT | GCG | CTA | TTA | GAA | TGT | GCA | CGT | GAT | ACA | GGA | GAA | TAT | TCT | TAT | TTT | 10673 |
| Phe | Ala | Leu | Leu | Glu | Cys | Ala | Arg | Asp | Thr | Gly | Glu | Tyr | Ser | Tyr | Phe | |
| 80 | | | | | 85 | | | | | 90 | | | | | | |
| CAT | TTT | TTA | TCT | GGA | GAT | GAT | ATG | CCA | ATC | AAA | GAT | AAT | GAA | ATA | GTA | 10721 |
| His | Phe | Leu | Ser | Gly | Asp | Asp | Met | Pro | Ile | Lys | Asp | Asn | Glu | Ile | Val | |
| 95 | | | | | 100 | | | | | 105 | | | | | 110 | |
| TTT | AAT | TTT | TTT | GAA | AAT | AGT | TAT | CCT | AAA | AAT | TTT | ATT | GAT | ATT | CTA | 10769 |
| Phe | Asn | Phe | Phe | Glu | Asn | Ser | Tyr | Pro | Lys | Asn | Phe | Ile | Asp | Ile | Leu | |
| | | | | 115 | | | | | 120 | | | | | 125 | | |
| GAT | TTT | GAA | AAT | GTC | AAT | AAA | AAT | TCA | TAT | TTC | TAC | GAA | CCC | CCT | GAG | 10817 |
| Asp | Phe | Glu | Asn | Val | Asn | Lys | Asn | Ser | Tyr | Phe | Tyr | Glu | Pro | Pro | Glu | |
| | | | 130 | | | | | 135 | | | | | 140 | | | |
| ATG | ATA | GAG | GAG | AGA | GTG | AAG | TAC | TAC | TAT | CCT | CAT | ATG | GAT | ATT | CTA | 10865 |
| Met | Ile | Glu | Glu | Arg | Val | Lys | Tyr | Tyr | Tyr | Pro | His | Met | Asp | Ile | Leu | |
| | | 145 | | | | | 150 | | | | | 155 | | | | |
| AAC | AGA | AAA | GGA | ACA | AAT | TTC | ATA | GGG | AAA | AAA | CTA | ATT | TAT | CTA | CAA | 10913 |
| Asn | Arg | Lys | Gly | Thr | Asn | Phe | Ile | Gly | Lys | Lys | Leu | Ile | Tyr | Leu | Gln | |
| | 160 | | | | | 165 | | | | | 170 | | | | | |
| AAA | TTG | TTG | AAA | GTT | AAT | CGC | TTG | AAA | AAT | AGA | GAG | ATA | GAA | ATT | TTC | 10961 |
| Lys | Leu | Leu | Lys | Val | Asn | Arg | Leu | Lys | Asn | Arg | Glu | Ile | Glu | Ile | Phe | |
| 175 | | | | | 180 | | | | | 185 | | | | | 190 | |
| AAG | GGT | CAT | CAA | TGG | TGT | AGT | TTG | ACA | AAT | CAA | TTT | GTA | GAT | ATT | TTA | 11009 |
| Lys | Gly | His | Gln | Trp | Cys | Ser | Leu | Thr | Asn | Gln | Phe | Val | Asp | Ile | Leu | |
| | | | | 195 | | | | | 200 | | | | | 205 | | |
| TTG | GAT | AAA | GAG | GAA | AGA | AGA | GTA | GGT | AAG | TCT | TAT | TTT | TCA | TCT | AGT | 11057 |
| Leu | Asp | Lys | Glu | Glu | Arg | Arg | Val | Gly | Lys | Ser | Tyr | Phe | Ser | Ser | Ser | |
| | | | 210 | | | | | 215 | | | | | 220 | | | |
| TTA | ATA | CCA | GAT | GAA | TGT | TAT | TTT | CAA | ACG | TTT | GCT | ATG | ATA | AAA | AAA | 11105 |
| Leu | Ile | Pro | Asp | Glu | Cys | Tyr | Phe | Gln | Thr | Phe | Ala | Met | Ile | Lys | Lys | |
| | | 225 | | | | | 230 | | | | | 235 | | | | |

| | | | | | | | | | | | | | | | | |
|---|---|---|---|---|---|---|---|---|---|---|---|---|---|---|---|---|
| GTT | GAA | ATT | TAT | CAA | CAG | AAA | AAT | ATG | TCA | GCA | CGC | TTA | ATT | GAT | TGG | 11153 |
| Val | Glu | Ile | Tyr | Gln | Gln | Lys | Asn | Met | Ser | Ala | Arg | Leu | Ile | Asp | Trp | |
| 240 | | | | | 245 | | | | | 250 | | | | | | |
| ACA | AGA | GGG | AAA | CCA | TAT | ATT | TGG | CGA | CAG | GAT | GAT | TTT | TTT | GAA | ATT | 11201 |
| Thr | Arg | Gly | Lys | Pro | Tyr | Ile | Trp | Arg | Gln | Asp | Asp | Phe | Phe | Glu | Ile | |
| 255 | | | | | 260 | | | | | 265 | | | | | 270 | |
| ATG | AAT | GAT | AAA | GAT | TCA | ATG | TTT | TCT | AGG | AAG | TTT | GAT | GAA | AAT | GTA | 11249 |
| Met | Asn | Asp | Lys | Asp | Ser | Met | Phe | Ser | Arg | Lys | Phe | Asp | Glu | Asn | Val | |
| | | | | 275 | | | | | 280 | | | | | 285 | | |
| GAT | CGT | AAA | ATA | ATT | GAA | GAA | ATT | TAT | ATA | AAA | ATA | AGA | GGA | AGA | AGT | 11297 |
| Asp | Arg | Lys | Ile | Ile | Glu | Glu | Ile | Tyr | Ile | Lys | Ile | Arg | Gly | Arg | Ser | |
| | | | 290 | | | | | 295 | | | | | 300 | | | |
| ACT | GAT | GAA | GCA | AAT | AAA | ATC | AAA | GAT | AAG | AGA | TTT | ACA | AAA | | | 11339 |
| Thr | Asp | Glu | Ala | Asn | Lys | Ile | Lys | Asp | Lys | Arg | Phe | Thr | Lys | | | |
| | | 305 | | | | | 310 | | | | | 315 | | | | |

TAATTTTACC TATGTTTTG GAAAGAAAAC TTTTCTTGGA AGGGGAGAAG CGATTATCAT 11399
AGATGAACCT GAGCATGGAA ATTGGGAGA TCAAGCAATT GCTTTTGCAG AAAATCAATT 11459
TTTAGTAAAT CATGTATCAG TACGAGATGT AGAACATCTT ATAGAAAGCA AAACTATTTC 11519
AGAAATAAAA TCTATAAAAA AAATATTGG AAAAAAGAA TTAGTTTTTT TTCATGGGGG 11579
AGGAAATTTC GGGACACTTT ATCTAAAGTA TGAGCGCATT AGAAGATTGG CAGTATCAAA 11639
GCTTCCCTTT AATAAAATGA TTCTATTTCC TCAGTCAATT TCATTTGAAG ATAGTAGGTT 11699
TGGTCAGAAG CAGCTGAATA AAAGTAAAAA AATATACAGT CAAAATACAA ATTTTATTTT 11759
GACTGCAAGA GAACCAAAAT CTTATGGTTT AATGAAGAAA TGTTTTCCAT ATAACAAAGT 11819
AATCTTGACA CCGGATATCG TGCTCTCATT TAAATTTGAA GTCACCATTT CTGATACGCA 11879
TATTGGGAAA GAAAAGGATA GTGTTATAAC TTATGAAAAT CGTCAACACT ATCTTGAGAT 11939
AAAGTGGGAT GAAATTGCGC AGCATGAGGT CGCCTTAACT GATAGATTAC ATGGTATGAT 11999
TTTTTCATAT ATCACAGGCA CACCATGTGT TGTTTGGCT AATAATAATC ATAAAATTGA 12059
AGGAACATAC AAACATTGGT TGAATGAAGT CAACTATATT CGTTTTATTG AAAATCCGAC 12119
TGTTGAAAAT ATTTTAGATG CAATCAATGA CTTAAAGCAA ATCGAACCTC ACTATATTGA 12179
TTTATCTGAT AAATTTCAAC CACTAATTGA TGCGATAAAA GGGTAAAGGT TTA ATG 12235
                                                          Met
                                                           1

| | | | | | | | | | | | | | | | | |
|---|---|---|---|---|---|---|---|---|---|---|---|---|---|---|---|---|
| AAT | AAA | TAT | AAA | AAA | CTA | CTA | TCC | AAC | TCT | CTT | GTT | TTC | ACG | ATA | GGA | 12283 |
| Asn | Lys | Tyr | Lys | Lys | Leu | Leu | Ser | Asn | Ser | Leu | Val | Phe | Thr | Ile | Gly | |
| | | | 5 | | | | | 10 | | | | | 15 | | | |
| AAC | TTA | GGC | AGC | AAA | CTG | TTA | GTC | TTT | TTA | CTC | GTA | CCG | CTC | TAC | ACC | 12331 |
| Asn | Leu | Gly | Ser | Lys | Leu | Leu | Val | Phe | Leu | Leu | Val | Pro | Leu | Tyr | Thr | |
| | | 20 | | | | | 25 | | | | | 30 | | | | |
| TAT | GCG | ATG | ACA | CCG | CAA | GAG | TAT | GGT | ATG | GCA | GAC | TTA | TAT | CAA | ACA | 12379 |
| Tyr | Ala | Met | Thr | Pro | Gln | Glu | Tyr | Gly | Met | Ala | Asp | Leu | Tyr | Gln | Thr | |
| | 35 | | | | | 40 | | | | | 45 | | | | | |
| ACA | GCA | AAT | CTA | CTT | TTG | CCA | TTA | ATT | ACA | ATG | AAT | GTA | TTT | GAT | GCA | 12427 |
| Thr | Ala | Asn | Leu | Leu | Leu | Pro | Leu | Ile | Thr | Met | Asn | Val | Phe | Asp | Ala | |
| 50 | | | | | 55 | | | | | 60 | | | | | 65 | |
| ACT | TTA | CGT | TTT | GCT | ATG | GAA | AAG | TCA | ATG | ACA | AAA | GAG | AGT | GTG | TTA | 12475 |
| Thr | Leu | Arg | Phe | Ala | Met | Glu | Lys | Ser | Met | Thr | Lys | Glu | Ser | Val | Leu | |
| | | | 70 | | | | | 75 | | | | | 80 | | | |
| ACA | AAT | TCT | CTT | GTG | GTT | TGG | TGT | TTT | AGC | GCG | GTG | TTC | ACT | TGT | TTG | 12523 |
| Thr | Asn | Ser | Leu | Val | Val | Trp | Cys | Phe | Ser | Ala | Val | Phe | Thr | Cys | Leu | |
| | | 85 | | | | | 90 | | | | | 95 | | | | |
| GGC | GCT | TGT | ATT | ATC | TAT | GCG | TTG | AAC | TTG | AGT | AAT | AAA | TGG | TAT | TTA | 12571 |
| Gly | Ala | Cys | Ile | Ile | Tyr | Ala | Leu | Asn | Leu | Ser | Asn | Lys | Trp | Tyr | Leu | |
| | 100 | | | | | 105 | | | | | 110 | | | | | |

```
GCT TTA CTT TTA ACC TTC AAC TTA TTT CAA GGT GGA CAA AGT ATA TTA      12619
Ala Leu Leu Leu Thr Phe Asn Leu Phe Gln Gly Gly Gln Ser Ile Leu
    115                 120                 125

AGC CAG TAT GCT AGA GGT ATA GGA AAG TCG AAA ATA TTT GCA GCT GGC      12667
Ser Gln Tyr Ala Arg Gly Ile Gly Lys Ser Lys Ile Phe Ala Ala Gly
130                 135                 140                 145

GGA GTT ATT TTA ACC TTT TTG ACA GGC GCT TTA AAT ATT CTT TTT TTG      12715
Gly Val Ile Leu Thr Phe Leu Thr Gly Ala Leu Asn Ile Leu Phe Leu
                150                 155                 160

GTA TAT TTA CCG CTT GGG ATT ACG GGC TAT TTA ATG TCC CTG GTT TTA      12763
Val Tyr Leu Pro Leu Gly Ile Thr Gly Tyr Leu Met Ser Leu Val Leu
                165                 170                 175

GCG AAT GTA GGT ACG ATT CTA TTT TTT GCT GGC ACA CTT TCC ATT TGG      12811
Ala Asn Val Gly Thr Ile Leu Phe Phe Ala Gly Thr Leu Ser Ile Trp
        180                 185                 190

AAG GAA ATT AGT TTT AAA ATA ATT GAT AAA AAA CTG ATT TGG CAA ATG      12859
Lys Glu Ile Ser Phe Lys Ile Ile Asp Lys Lys Leu Ile Trp Gln Met
        195                 200                 205

CTC TAT TAT GCC TTA CCT TTG ATT CCT AGT TCC ATC CTG TGG TGG TTA      12907
Leu Tyr Tyr Ala Leu Pro Leu Ile Pro Ser Ser Ile Leu Trp Trp Leu
210                 215                 220                 225

CTG AAT GCT TCT AGT CGC TAT TTC GTT TTA TTC TTT TTA GGA GCA GGT      12955
Leu Asn Ala Ser Ser Arg Tyr Phe Val Leu Phe Phe Leu Gly Ala Gly
                230                 235                 240

GCT AAT GGT CTT TTG GCG GTC GCT ACC AAA ATT CCA AGT ATT ATT TCC      13003
Ala Asn Gly Leu Leu Ala Val Ala Thr Lys Ile Pro Ser Ile Ile Ser
                245                 250                 255

ATT TTT AAT ACG ATT TTT ACA CAG GCG TGG CAA ATT TCA GCC ATA GAA      13051
Ile Phe Asn Thr Ile Phe Thr Gln Ala Trp Gln Ile Ser Ala Ile Glu
        260                 265                 270

GAA TAT GAT TCT CAT CAA AAA TCA AAA TAT TAT TCG GAT GTT TTT CAC      13099
Glu Tyr Asp Ser His Gln Lys Ser Lys Tyr Tyr Ser Asp Val Phe His
275                 280                 285

TAC TTA GCA ACT TTT CTA TTG TTA GGG ACA TCA GCT TTT ATG ATT GTG      13147
Tyr Leu Ala Thr Phe Leu Leu Leu Gly Thr Ser Ala Phe Met Ile Val
290                 295                 300                 305

CTT AAA CCA ATT GTC GAA AAA GTC GTT TCA AGT GAC TAT GCA AGT TCA      13195
Leu Lys Pro Ile Val Glu Lys Val Val Ser Ser Asp Tyr Ala Ser Ser
                310                 315                 320

TGG CAA TAT GTT CCT TTC TTT ATG TTG TCG ATG CTA TTT TCC TCG TTT      13243
Trp Gln Tyr Val Pro Phe Phe Met Leu Ser Met Leu Phe Ser Ser Phe
                325                 330                 335

TCT GAT TTT TTT GGG ACT AAT TAT ATT GCG GCT AAA CAA ACA AAA GGC      13291
Ser Asp Phe Phe Gly Thr Asn Tyr Ile Ala Ala Lys Gln Thr Lys Gly
        340                 345                 350

GTA TTT ATG ACA TCT ATC TAT GGT ACC ATT GTT TGT GTC TTA CTC CAA      13339
Val Phe Met Thr Ser Ile Tyr Gly Thr Ile Val Cys Val Leu Leu Gln
        355                 360                 365

GTG GTG CTG CTA CCC ATC ATC GGC TTG GAT GGC GCA GGT TTA TCA GCC      13387
Val Val Leu Leu Pro Ile Ile Gly Leu Asp Gly Ala Gly Leu Ser Ala
370                 375                 380                 385

ATG CTT GGA TTT TTA ACA ACG TTT TTA TTG CGT GTC AAA GAT ACG CAA      13435
Met Leu Gly Phe Leu Thr Thr Phe Leu Leu Arg Val Lys Asp Thr Gln
                390                 395                 400

AAA TTT GTG GTG ATT CAG ATT AAG TGG CGG ATT TTT ATC AGT AAT TTA      13483
Lys Phe Val Val Ile Gln Ile Lys Trp Arg Ile Phe Ile Ser Asn Leu
                405                 410                 415

TTG ATC GTT TTG GCA CAA ATT TTA TGT TTG TTT TAT CTA CCG AGT GAA      13531
Leu Ile Val Leu Ala Gln Ile Leu Cys Leu Phe Tyr Leu Pro Ser Glu
                420                 425                 430
```

```
TTT  TTG  TAT  TTT  GGT  CTT  GCC  CTA  TTA  TTT  TGT  GGC  ATG  TTA  GTG  GTT      13579
Phe  Leu  Tyr  Phe  Gly  Leu  Ala  Leu  Leu  Phe  Cys  Gly  Met  Leu  Val  Val
     435                      440                     445

AAT  CAG  CGT  ACA  ATT  TTA  TAC  ATT  ATC  ATG  GCG  CTA  AAA  ATA  AAA  AAT      13627
Asn  Gln  Arg  Thr  Ile  Leu  Tyr  Ile  Ile  Met  Ala  Leu  Lys  Ile  Lys  Asn
450                      455                     460                      465

AAG  ACA  TTT  GGA  ATG  AAA  TCC  TCA  TAAAAATAGA  CAGGAGGTGT  ATCTCGAATG           13681
Lys  Thr  Phe  Gly  Met  Lys  Ser  Ser
               470

GTATCGAGAT  ATATCTCCTG  TCTATTTTTA  TGATACTTTT  GTGTTAGCTC  AACTCAACCG              13741
CCTTTTAATC  TCCCAACAAC  AATAATACCC  AATCAAACAA  CCCAAAAAAT  TCAAGATAAT              13801
ATCACTAATG  GCAAATGTGC  CCAAATAAAA  GATAAATTGA  ATGGTTTCAA  TTACTAAAAG              13861
AGTGACCAAA  CTGACAATGA  CAAACTGTTT  GAAATCAGTA  TTGATACAGT  AAAGGCCACC              13921
TAAAGGAATG  AAGTAGATAA  TATTTAGCAC  AGCCTCTTGA  ATCGTTCTGG  GATCCGCTTT              13981
TATAAAGTCA  AAAGGATTCA  GTGACATCGC  CTGAAAATCC  GTTATTTTAG  TAAAAAGTAC              14041
CATGAATAAC  AGTAATAAAT  ACACACTGAA  AGCAAGATAG  AGATAAATAA  CTGAAAAATA              14101
TTTGAGGTGA  TACTGGATAC  CAAACAACCA  GATAATCAGC  GTTAATAAGA  GTATTAAAGT              14161
CAATGTGGTA  TAGTCAAAGT  GGTTAATCAA  CTTAGCCAGG  CTTTGATAGC  GAGTGAGAAC              14221
GGGCATAATC  AGCCAAGTAA  TCGTCGCATA  ACTCAGGATA  AATGTGATCA  ATAAACTGCT              14281
GAGGTAGATC  ATATATTTTC  GCAACTGTTT  CTAACTCCTT  TTCTTGATGA  GATTAACCCT              14341
ATTTTAACAT  ATTTTAAAAC  TGTCATGTTT  TTATGAATTT  AAAATAAATG  TTAAAGAAAA              14401
TAAAAATTCA  CCAGTTGGTT  CTGTTGCAAA  GTTTTCCAAA  AAATCTATTT  TAGTGTAAAA              14461
TTGAGAAAAA  AGACAGAGAG  GACAGAGTAA  TGAATTATTT  TAAAGGCAAA  CAATTCAAAA              14521
AAGACGTCAT  TATTGTCTCT  GTTGGTTACT  ACCTGCGTTA  CAATCTAAGC  TATCGTTAAG              14581
TTCAGGAATT  GTTATATGAT  C                                                           14602
```

( 2 ) INFORMATION FOR SEQ ID NO:2:

( i ) SEQUENCE CHARACTERISTICS:
        ( A ) LENGTH: 484 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Ser  Ser  Arg  Thr  Asn  Arg  Lys  Gln  Lys  His  Thr  Ser  Asn  Gly  Ser
 1             5                    10                       15

Trp  Gly  Met  Val  Asn  Val  Gly  Leu  Thr  Ile  Leu  Tyr  Ala  Ile  Leu  Ala
               20                       25                       30

Leu  Val  Leu  Leu  Phe  Thr  Met  Phe  Asn  Tyr  Asn  Phe  Leu  Ser  Phe  Arg
          35                       40                       45

Phe  Leu  Asn  Ile  Ile  Ile  Thr  Ile  Gly  Leu  Leu  Val  Val  Leu  Ala  Ile
     50                       55                       60

Ser  Ile  Phe  Leu  Gln  Lys  Thr  Lys  Lys  Leu  Pro  Leu  Val  Thr  Thr  Val
65                       70                       75                       80

Val  Leu  Val  Ile  Phe  Ser  Leu  Val  Ser  Leu  Val  Gly  Ile  Phe  Gly  Phe
                    85                       90                       95

Lys  Gln  Met  Ile  Asp  Ile  Thr  Asn  Arg  Met  Asn  Gln  Thr  Ala  Ala  Phe
               100                      105                      110

Ser  Glu  Val  Glu  Met  Ser  Ile  Val  Val  Pro  Lys  Glu  Ser  Asp  Ile  Lys
          115                      120                      125
```

Asp Val Ser Gln Leu Thr Ser Val Gln Ala Pro Thr Lys Val Asp Lys
    130                     135                 140

Asn Asn Ile Glu Ile Leu Met Ser Ala Leu Lys Lys Asp Lys Lys Val
145             150                 155                 160

Asp Val Lys Val Asp Val Ala Ser Tyr Gln Glu Ala Tyr Asp Asn
                165             170                 175

Leu Lys Ser Gly Lys Ser Lys Ala Met Val Leu Ser Gly Ser Tyr Ala
            180              185                190

Ser Leu Leu Glu Ser Val Asp Ser Asn Tyr Ala Ser Asn Leu Lys Thr
        195                 200             205

Ile Tyr Thr Tyr Lys Ile Lys Lys Asn Ser Asn Ser Ala Asn Gln
    210             215             220

Val Asp Ser Arg Val Phe Asn Ile Tyr Ile Ser Gly Ile Asp Thr Tyr
225             230                 235                 240

Gly Pro Ile Ser Thr Val Ser Arg Ser Asp Val Asn Ile Ile Met Thr
            245                 250                 255

Val Asn Met Asn Thr His Lys Ile Leu Leu Thr Thr Thr Pro Arg Asp
            260             265                 270

Ala Tyr Val Lys Ile Pro Gly Gly Gly Ala Asp Gln Tyr Asp Lys Leu
    275                 280                 285

Thr His Ala Gly Ile Tyr Gly Val Glu Thr Ser Glu Gln Thr Leu Glu
    290             295                 300

Asp Leu Tyr Gly Ile Lys Leu Asp Tyr Tyr Ala Arg Ile Asn Phe Thr
305             310                 315                 320

Ser Phe Leu Lys Leu Ile Asp Gln Leu Gly Gly Val Thr Val His Asn
            325                 330                 335

Asp Gln Ala Phe Thr Gln Glu Lys Phe Asp Phe Pro Val Gly Asp Ile
            340                 345                 350

Gln Met Asn Ser Glu Gln Ala Leu Gly Phe Val Arg Glu Arg Tyr Asn
        355                 360                 365

Leu Asp Gly Gly Asp Asn Asp Arg Gly Lys Asn Gln Glu Lys Val Ile
    370                 375                 380

Ser Ala Ile Leu Asn Lys Leu Ala Ser Leu Lys Ser Val Ser Asn Phe
385             390                 395                 400

Thr Ser Ile Val Asn Asn Leu Gln Asp Ser Val Gln Thr Asn Met Ser
                405                 410                 415

Leu Asn Thr Ile Asn Ala Leu Ala Asn Thr Gln Leu Glu Ser Gly Ser
                420                 425             430

Lys Phe Thr Val Thr Ser Gln Ala Val Thr Gly Thr Gly Ser Thr Gly
        435                 440                 445

Gln Leu Ile Ser Tyr Ala Met Pro Asn Ser Ser Leu Tyr Met Met Lys
    450                 455                 460

Leu Asp Asn Ser Ser Val Glu Ser Ala Ser Gln Ala Ile Lys Lys Leu
465                 470                 475                 480

Met Glu Glu Lys (2) INFORMATION FOR SEQ ID NO:3:

(i) SEQUENCE CHARACTERISTICS:
        (A) LENGTH: 243 amino acids
        (B) TYPE: amino acid
        (D) TOPOLOGY: linear (ii) MOLECULE TYPE: protein (xi) SEQUENCE DESCRIPTION: SEQ ID NO:3:

| Val | Ile | Asp | Val | His | Ser | His | Ile | Val | Phe | Asp | Val | Asp | Gly | Pro |
| 1 | | | | 5 | | | | | 10 | | | | | 15 |

| Glu | Thr | Leu | Glu | Glu | Ser | Leu | Asp | Leu | Ile | Gly | Glu | Ser | Tyr | Ala | Gln |
| | | | 20 | | | | | 25 | | | | | 30 | | |

| Gly | Val | Arg | Lys | Ile | Val | Ser | Thr | Ser | His | Arg | Arg | Lys | Gly | Met | Phe |
| | | 35 | | | | | 40 | | | | | 45 | | | |

| Glu | Thr | Pro | Glu | Asp | Lys | Ile | Phe | Ala | Asn | Phe | Lys | Lys | Val | Lys | Ala |
| | 50 | | | | | 55 | | | | | 60 | | | | |

| Glu | Ala | Glu | Ala | Leu | Tyr | Pro | Asp | Leu | Thr | Ile | Tyr | Tyr | Gly | Gly | Glu |
| 65 | | | | | 70 | | | | | 75 | | | | | 80 |

| Leu | Tyr | Tyr | Thr | Ser | Asp | Ile | Val | Glu | Lys | Leu | Glu | Lys | Asn | Leu | Ile |
| | | | | 85 | | | | | 90 | | | | | | 95 |

| Pro | Arg | Met | His | Asn | Thr | Gln | Phe | Ala | Leu | Ile | Glu | Phe | Ser | Ala | Arg |
| | | | 100 | | | | | | 105 | | | | | 110 | |

| Thr | Ser | Trp | Lys | Glu | Ile | His | Ser | Gly | Leu | Ser | Asn | Val | Leu | Arg | Ala |
| | | | 115 | | | | | 120 | | | | | 125 | | |

| Gly | Val | Thr | Pro | Ile | Val | Ala | His | Ile | Glu | Arg | Tyr | Asp | Ala | Leu | Glu |
| | | 130 | | | | | 135 | | | | | 140 | | | |

| Glu | Asn | Ala | Asp | Arg | Val | Arg | Glu | Ile | Ile | Asn | Met | Gly | Cys | Tyr | Thr |
| 145 | | | | | 150 | | | | | 155 | | | | | 160 |

| Gln | Val | Asn | Ser | Ser | His | Val | Leu | Lys | Pro | Lys | Leu | Phe | Gly | Asp | Lys |
| | | | | 165 | | | | | 170 | | | | | 175 | |

| Asp | Lys | Val | Arg | Lys | Lys | Arg | Val | Arg | Phe | Phe | Leu | Glu | Lys | Asn | Leu |
| | | | | 180 | | | | | 185 | | | | | 190 | |

| Val | His | Met | Val | Ala | Ser | Asp | Met | His | Asn | Leu | Gly | Pro | Arg | Pro | Pro |
| | | | 195 | | | | | 200 | | | | | 205 | | |

| Phe | Met | Lys | Asp | Ala | Tyr | Glu | Ile | Val | Lys | Lys | Asn | Tyr | Gly | Ser | Lys |
| | | 210 | | | | | 215 | | | | | 220 | | | |

| Arg | Ala | Lys | Asn | Leu | Phe | Ile | Glu | Asn | Pro | Lys | Thr | Leu | Leu | Glu | Asn |
| 225 | | | | | 230 | | | | | 235 | | | | | 240 |

| Gln | Tyr | Leu |

(2) INFORMATION FOR SEQ ID NO:4:

(i) SEQUENCE CHARACTERISTICS:
    (A) LENGTH: 230 amino acids
    (B) TYPE: amino acid
    (D) TOPOLOGY: linear (ii) MOLECULE TYPE: protein (xi) SEQUENCE DESCRIPTION: SEQ ID NO:4:

| Met | Asn | Gln | Asp | Asn | Thr | Lys | Ser | Asp | Glu | Ile | Asp | Val | Leu | Ala | Leu |
| 1 | | | | 5 | | | | | 10 | | | | | 15 | |

| Leu | His | Lys | Leu | Trp | Thr | Lys | Lys | Leu | Leu | Ile | Leu | Phe | Thr | Ala | Phe |
| | | | | 20 | | | | | 25 | | | | | 30 | |

| Tyr | Phe | Ala | Val | Phe | Ser | Phe | Leu | Gly | Thr | Tyr | Phe | Phe | Ile | Gln | Pro |
| | | 35 | | | | | 40 | | | | | 45 | | | |

| Thr | Tyr | Thr | Ser | Thr | Thr | Arg | Ile | Tyr | Val | Val | Asn | Gln | Ala | Thr | Asp |
| | 50 | | | | | 55 | | | | | 60 | | | | |

| Asn | Lys | Asn | Leu | Ser | Ala | Gln | Asp | Leu | Gln | Ala | Gly | Thr | Tyr | Leu | Ala |
| 65 | | | | | 70 | | | | | 75 | | | | | 80 |

| Asn | Asp | Tyr | Lys | Glu | Ile | Ile | Ala | Ser | Asn | Asp | Val | Leu | Ser | Glu | Val |
| | | | | 85 | | | | | 90 | | | | | 95 | |

| Ile | Lys | Asp | Glu | Lys | Leu | Asn | Leu | Ser | Glu | Ala | Glu | Leu | Ser | Lys | Met |
| | | | 100 | | | | | 105 | | | | | 110 | | |

| Val | Ser | Val | Asn | Ile | Pro | Thr | Asp | Thr | Arg | Leu | Ile | Ser | Ile | Ser | Val |
|---|---|---|---|---|---|---|---|---|---|---|---|---|---|---|---|
| | | 115 | | | | 120 | | | | | 125 | | | | |
| Asn | Ala | Lys | Thr | Gly | Gln | Asp | Ala | Gln | Thr | Leu | Ala | Asn | Lys | Val | Arg |
| 130 | | | | | 135 | | | | | 140 | | | | | |
| Glu | Val | Ala | Ser | Lys | Lys | Ile | Lys | Lys | Val | Thr | Lys | Val | Glu | Asp | Val |
| 145 | | | | | 150 | | | | | 155 | | | | | 160 |
| Thr | Thr | Leu | Glu | Glu | Ala | Lys | Leu | Pro | Glu | Ser | Pro | Ser | Ser | Pro | Asn |
| | | | | 165 | | | | | 170 | | | | | 175 | |
| Ile | Lys | Leu | Asn | Val | Leu | Leu | Gly | Ala | Val | Leu | Gly | Gly | Phe | Leu | Ala |
| | | | 180 | | | | | 185 | | | | | 190 | | |
| Val | Val | Gly | Val | Leu | Val | Arg | Glu | Ile | Leu | Asp | Asp | Arg | Val | Arg | Arg |
| | | 195 | | | | | 200 | | | | | 205 | | | |
| Pro | Glu | Asp | Val | Glu | Asp | Ala | Leu | Gly | Met | Thr | Leu | Leu | Gly | Ile | Val |
| 210 | | | | | 215 | | | | | 220 | | | | | |
| Pro | Asp | Thr | Asp | Lys | Ile | | | | | | | | | | |
| 225 | | | | | 230 | | | | | | | | | | |

( 2 ) INFORMATION FOR SEQ ID NO:5:

( i ) SEQUENCE CHARACTERISTICS:
        ( A ) LENGTH: 249 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| Met | Pro | Leu | Leu | Lys | Leu | Val | Lys | Ser | Lys | Val | Asp | Phe | Ala | Lys | Lys |
|---|---|---|---|---|---|---|---|---|---|---|---|---|---|---|---|
| 1 | | | | 5 | | | | | 10 | | | | | 15 | |
| Thr | Glu | Glu | Tyr | Tyr | Asn | Ala | Ile | Arg | Thr | Asn | Ile | Gln | Phe | Ser | Gly |
| | | | 20 | | | | | 25 | | | | | 30 | | |
| Ala | Gln | Met | Lys | Val | Ile | Ala | Ile | Ser | Ser | Val | Glu | Ala | Gly | Glu | Gly |
| | | 35 | | | | | 40 | | | | | 45 | | | |
| Lys | Ser | Met | Ile | Ser | Val | Asn | Leu | Ala | Ile | Ser | Phe | Ala | Ser | Val | Gly |
| | | 50 | | | | 55 | | | | | 60 | | | | |
| Leu | Arg | Thr | Leu | Leu | Ile | Asp | Ala | Glu | Thr | Arg | Asn | Ser | Val | Leu | Ser |
| 65 | | | | | 70 | | | | | 75 | | | | | 80 |
| Gly | Thr | Phe | Lys | Ser | Asn | Glu | Pro | Tyr | Lys | Gly | Leu | Ser | Asn | Phe | Leu |
| | | | | 85 | | | | | 90 | | | | | 95 | |
| Ser | Gly | Asn | Ala | Asp | Leu | Asn | Glu | Thr | Ile | Cys | Gln | Thr | Asp | Ile | Ser |
| | | | 100 | | | | | 105 | | | | | 110 | | |
| Gly | Leu | Asp | Val | Ile | Ala | Ser | Gly | Pro | Val | Pro | Pro | Asn | Pro | Thr | Ser |
| | | 115 | | | | | 120 | | | | | 125 | | | |
| Leu | Leu | Gln | Asn | Asp | Asn | Phe | Arg | His | Leu | Met | Glu | Val | Ala | Arg | Ser |
| | 130 | | | | | 135 | | | | | 140 | | | | |
| Cys | Tyr | Asp | Tyr | Val | Ile | Ile | Asp | Thr | Pro | Pro | Val | Gly | Leu | Val | Ile |
| 145 | | | | | 150 | | | | | 155 | | | | | 160 |
| Asp | Ala | Val | Ile | Ile | Ala | His | Gln | Ala | Asp | Ala | Ser | Leu | Leu | Val | Thr |
| | | | | 165 | | | | | 170 | | | | | 175 | |
| Glu | Ala | Gly | Lys | Ile | Lys | Arg | Arg | Phe | Val | Thr | Lys | Ala | Val | Glu | Gln |
| | | | 180 | | | | | 185 | | | | | 190 | | |
| Leu | Val | Glu | Ser | Gly | Ser | Gln | Phe | Leu | Gly | Val | Val | Leu | Asn | Lys | Val |
| | | 195 | | | | | 200 | | | | | 205 | | | |
| Asp | Met | Thr | Val | Asp | Lys | Tyr | Gly | Phe | Tyr | Gly | Ser | Tyr | Gly | Ser | Tyr |
| | 210 | | | | | 215 | | | | | 220 | | | | |
| Gly | Glu | Tyr | Gly | Lys | Lys | Ser | Asp | Gln | Lys | Glu | Gly | His | Ser | Arg | Ala |
| 225 | | | | | 230 | | | | | 235 | | | | | 240 |

His Arg Arg Arg Lys Val Gly Trp Asn
                245

( 2 ) INFORMATION FOR SEQ ID NO:6:

( i ) SEQUENCE CHARACTERISTICS:
        ( A ) LENGTH: 227 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

Met Ser Gln Ala Lys Glu Glu Ile Ser Asp Val Met Thr Tyr Ser Glu
 1               5                  10                  15

Leu Thr Ser His Lys Pro Lys Ile Ile Tyr Ser Leu Ile Lys Arg Ile
                20                  25                  30

Gly Asp Ile Leu Val Ser Ser Ile Gly Leu Ile Ile Leu Ile Pro Leu
             35                  40                  45

Phe Leu Ile Val Ala Leu Ile Met Lys Cys Ser Glu Pro Thr Ala Pro
     50                  55                  60

Ile Phe Phe Ser His Ile Arg Asn Gly Lys Asn Gly Lys Lys Phe Lys
 65                  70                  75                  80

Met Tyr Lys Phe Arg Thr Met Cys Gln Asp Ala Glu Ser Ile Leu Met
                85                  90                  95

Lys Asp Thr Glu Leu Phe Ala Lys Phe Lys Ala Asn Gly Tyr Lys Leu
                100                 105                 110

Glu Thr His Glu Asp Pro Arg Ile Thr Lys Ile Gly Gly Ile Leu Arg
            115                 120                 125

Lys Thr Ser Ile Asp Glu Leu Pro Gln Leu Ile Asn Val Phe Leu Gly
    130                 135                 140

Gln Met Ser Leu Val Gly Pro Arg Pro Leu Pro Asp Arg Glu Ile Ile
145                 150                 155                 160

Glu Tyr Gly Asp Asn Gln Glu Lys Phe Leu Ser Val Lys Pro Gly Met
                165                 170                 175

Thr Gly Trp Trp Gln Val Ser Gly Arg Ser Thr Ile Gly Tyr Pro Glu
            180                 185                 190

Arg Cys His Leu Glu Leu Tyr Tyr Val Glu Lys Cys Cys Phe Thr Phe
        195                 200                 205

Asp Val Leu Ile Leu Leu Lys Thr Ile Gly Ile Val Leu Lys Arg Val
    210                 215                 220

Gly Ala Arg
225

( 2 ) INFORMATION FOR SEQ ID NO:7:

( i ) SEQUENCE CHARACTERISTICS:
        ( A ) LENGTH: 319 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

Met Asn Glu Gln Val Thr Phe Ile Leu Cys Asp Phe Leu Val Arg Glu
 1               5                  10                  15

Ile Lys Pro Lys Tyr Asp Leu Leu Ala Tyr Gln Phe Ile Ser Lys Lys
                20                  25                  30

Ile Lys Glu Ile Lys Pro Asp Ile Val His Cys His Ser Ser Lys Ala

```
                    35                      40                         45
Gly  Val  Ile  Gly  Arg  Leu  Ala  Ala  Lys  Arg  Arg  Gly  Val  Lys  Lys  Ile
          50                        55                    60

Phe  Tyr  Thr  Pro  His  Ala  Tyr  Ser  Phe  Leu  Ala  Pro  Glu  Phe  Ser  Gly
65                        70                        75                        80

Lys  Lys  Lys  Phe  Leu  Phe  Val  Gln  Ile  Glu  Lys  Phe  Leu  Ser  Arg  Phe
                    85                        90                        95

Ala  Thr  Thr  Lys  Ile  Phe  Cys  Val  Ser  Ile  Ala  Glu  Met  Gln  Ala  Ala
                    100                      105                     110

Leu  Glu  Val  Asn  Leu  Asp  Lys  Thr  Asp  Lys  Phe  Gln  Val  Ile  Tyr  Asn
          115                      120                      125

Gly  Leu  Pro  Glu  Ile  Asp  Leu  Pro  Ser  Lys  Glu  Thr  Ile  Arg  Ala  Gln
     130                      135                      140

Leu  Gly  Leu  Glu  Lys  Ala  Ala  Val  Val  Ile  Gly  Asn  Asn  Ala  Lys  Met
145                      150                      155                      160

Ser  Glu  Gln  Lys  Asn  Pro  Met  Phe  Phe  Met  Glu  Ile  Ala  Arg  Lys  Met
               165                      170                      175

Ile  Arg  Gln  Asn  Ala  Asn  Trp  His  Phe  Val  Trp  Val  Gly  Asp  Gly  Gln
               180                      185                      190

Leu  Met  Pro  Leu  Phe  Gln  Ser  Phe  Ile  Lys  Gln  Asn  Gly  Leu  Glu  Gly
          195                      200                      205

Asn  Ile  His  Leu  Leu  Gly  Glu  Arg  Pro  Asp  Ser  Glu  Ile  Val  Val  Thr
          210                      215                      220

Ala  Tyr  Asp  Ile  Phe  Leu  Thr  Thr  Ser  Gln  Tyr  Glu  Gly  Leu  Pro  Tyr
225                      230                      235                      240

Ala  Pro  Ile  Glu  Ala  Met  Arg  Ala  Gly  Val  Pro  Ile  Leu  Ala  Thr  Lys
               245                      250                      255

Val  Val  Gly  Asn  Ser  Glu  Leu  Val  Ile  Glu  Gly  Lys  Asn  Gly  Tyr  Leu
               260                      265                      270

Ile  Asp  Leu  Glu  Trp  Ser  Lys  Ser  Val  Glu  Glu  Lys  Leu  Tyr  Lys  Ala
          275                      280                      285

Ala  Lys  Ile  Asp  Ala  Gln  Met  Ile  Lys  Ala  Asp  Phe  Arg  Gln  Arg  Phe
     290                      295                      300

Ala  Ile  Asp  Gln  Ile  Leu  Lys  Gln  Ile  Glu  Thr  Ile  Tyr  Leu  Ala
305                      310                      315
```

( 2 ) INFORMATION FOR SEQ ID NO:8:

( i ) SEQUENCE CHARACTERISTICS:
        ( A ) LENGTH: 372 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met  Lys  Lys  Ile  Ser  Ile  Leu  His  Phe  Ser  Gln  Val  Ser  Gly  Gly  Gly
1              5                        10                       15

Val  Glu  Lys  Tyr  Ile  Lys  Leu  Phe  Leu  Lys  Tyr  Ser  Asp  Val  Thr  Lys
               20                       25                       30

Phe  Asn  Asn  Tyr  Leu  Val  Ala  Pro  Asn  Leu  Glu  Asn  Tyr  Asp  Glu  Phe
          35                       40                       45

Asn  Gly  Tyr  Leu  Lys  Met  Ser  Val  Asn  Phe  Asn  Met  Glu  Gln  Thr  Phe
     50                       55                       60

Ser  Pro  Leu  Lys  Ile  Phe  Lys  Asn  Val  Phe  Phe  Ile  Arg  Ser  Val  Leu
65                       70                       75                       80
```

-continued

| | | | | | | | | | | | | | | |
|---|---|---|---|---|---|---|---|---|---|---|---|---|---|---|
| Lys | Lys | Ile | Asn | Pro<br>85 | Asp | Ile | Val | Tyr | Leu<br>90 | His | Ser | Thr | Phe | Ala<br>95 | Gly |
| Val | Val | Gly | Arg<br>100 | Ile | Ala | Ser | Ile | Gly<br>105 | Leu | Pro | Thr | Lys | Val<br>110 | Val | Tyr |
| Asn | Pro | His<br>115 | Gly | Trp | Ser | Phe | Lys<br>120 | Met | Asp | Asn | Ser | Tyr<br>125 | Leu | Lys | Lys |
| Leu | Ile<br>130 | Phe | Lys | Leu | Ile | Glu<br>135 | Phe | Ser | Leu | Ser | Phe<br>140 | Leu | Thr | Asp | Lys |
| Phe<br>145 | Ile | Leu | Ile | Ser | Glu<br>150 | Ser | Glu | Tyr | Ile | Leu<br>155 | Ala | Asn | His | Ile | Ser<br>160 |
| Phe | Asn | Lys | Ser | Lys<br>165 | Phe | Ser | Leu | Ile | Asn<br>170 | Asn | Gly | Val | Glu | Val<br>175 | Ile |
| Thr | Gly | Asp | Ser<br>180 | Arg | Asn | Glu | Ile | Glu<br>185 | Glu | Ile | Phe | Pro | Asn<br>190 | Glu | Asp |
| Phe | Ile | Ile<br>195 | Gly | Met | Val | Gly<br>200 | Arg | Leu | Ser | Pro | Pro<br>205 | Lys | Glu | Phe | Phe |
| Phe | Phe<br>210 | Ile | Asp | Phe | Ala | Lys<br>215 | Lys | Ile | Leu | Gln | Ile<br>220 | Arg | Asn | Asp | Thr |
| Asn<br>225 | Phe | Ile | Ile | Val | Gly<br>230 | Asp | Gly | Glu | Leu | Arg<br>235 | Ser | Glu | Ile | Glu | Arg<br>240 |
| Met | Ile | Leu | Asp | Asn<br>245 | Gly | Leu | Gly | Asp | Lys<br>250 | Ile | Tyr | Ile | Thr | Gly<br>255 | Trp |
| Val | Asp | Asn | Pro<br>260 | Arg | Asn | Tyr | Ile | Glu<br>265 | Lys | Phe | Asp | Gln | Ala<br>270 | Ile | Leu |
| Phe | Ser | Arg<br>275 | Trp | Glu | Gly | Leu | Ser<br>280 | Leu | Thr | Ile | Ala | Glu<br>285 | Tyr | Met | Ser |
| Gln | Lys<br>290 | Lys | Thr | Ile | Leu | Ala<br>295 | Thr | Asn | Ile | Gly | Gly<br>300 | Ile | Asn | Asp | Leu |
| Ile<br>305 | Thr | Asp | Gly | Glu | Thr<br>310 | Gly | Met | Leu | Ile | Glu<br>315 | Val | Gly | Asp | Leu | Asn<br>320 |
| Ser | Ala | Val | Ser | Lys<br>325 | Ser | Phe | Glu | Leu | Arg<br>330 | Asn | Asn | Lys | Glu | Val<br>335 | Ser |
| Asn | Gln | Leu | Ala<br>340 | Asn | Asn | Ala | Tyr | Asn<br>345 | Lys | Val | Val | Glu | Gln<br>350 | Phe | Ser |
| Ile | Glu | Lys<br>355 | Gln | Met | Ala | Glu | Ile<br>360 | Glu | Ser | Leu | Phe | Ile<br>365 | Glu | Met | Cys |
| Asn | Asn | Glu | Lys<br>370 | | | | | | | | | | | | |

( 2 ) INFORMATION FOR SEQ ID NO:9:

( i ) SEQUENCE CHARACTERISTICS:
        ( A ) LENGTH: 159 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

| | | | | | | | | | | | | | | |
|---|---|---|---|---|---|---|---|---|---|---|---|---|---|---|
| Met<br>1 | Leu | Ile | Leu | Lys<br>5 | Leu | Lys | Phe | His | Leu<br>10 | Lys | Ser | Leu | Phe | Leu<br>15 | Lys |
| Trp | Ile | Tyr | Arg<br>20 | Leu | Leu | Tyr | Leu | Lys<br>25 | Lys | Phe | Gln | Phe | Gly<br>30 | Ala | Arg |
| Leu | Thr | Phe<br>35 | Arg | Asp | Gly | Phe | His<br>40 | Leu | Leu | Ile | Glu | Lys<br>45 | Ser | Gly | Lys |
| Val | Ile<br>50 | Ile | Gly | Asn | His | Val<br>55 | Phe | Phe | Asn | Asn | Phe<br>60 | Cys | Ser | Ile | Asn |

```
Ala Met Leu Ser Val Thr Ile Gly Asp Asp Cys Ile Phe Gly Glu Asn
 65              70                  75                  80

Val Lys Ile Tyr Asp His Asn His Cys Tyr Gln Asn Lys Ser Gln Pro
                 85                  90                  95

Ile Ser Lys Gln Gly Phe Ser Thr Ala Ala Ile Gln Ile Gly Arg Asn
                100                 105                 110

Cys Trp Ile Gly Ser Gln Val Thr Ile Leu Lys Gly Val Thr Ile Gly
            115                 120                 125

Asp Asn Ser Ile Ile Gly Ala Gly Val Val Val Tyr Gln Asp Val Pro
            130                 135                 140

Glu Asn Ser Ile Val Leu Ser Asn Gly Glu Ile Arg Lys Arg Gly
145                 150                 155
```

( 2 ) INFORMATION FOR SEQ ID NO:10:

( i ) SEQUENCE CHARACTERISTICS:
      ( A ) LENGTH: 324 amino acids
      ( B ) TYPE: amino acid
      ( D ) TOPOLOGY: linear ( i i ) MOLECULE TYPE: protein ( x i ) SEQUENCE DESCRIPTION: SEQ ID NO:10:

```
Met Tyr Leu Lys Ser Leu Ile Ser Ile Val Ile Pro Val Tyr Asn Val
 1               5                  10                  15

Glu Lys Tyr Leu Glu Lys Cys Leu Gln Ser Val Gln Asn Gln Thr Tyr
                 20                  25                  30

Asn Asn Phe Glu Val Ile Leu Val Asn Asp Gly Ser Thr Asp Ser Ser
             35                  40                  45

Leu Ser Ile Cys Glu Lys Phe Val Asn Gln Asp Lys Arg Phe Ser Val
         50                  55                  60

Phe Ser Lys Glu Asn Gly Gly Met Ser Ser Ala Arg Asn Phe Gly Ile
 65              70                  75                  80

Lys Lys Ala Lys Gly Ser Phe Ile Thr Phe Val Asp Ser Asp Asp Tyr
                 85                  90                  95

Ile Val Lys Asp Tyr Leu Ser His Leu Val Ala Gly Ile Lys Ser Glu
                100                 105                 110

Thr Ser Ile Val Cys Ser Lys Phe Phe Leu Val Asp Glu Lys Gly Ser
            115                 120                 125

Leu Leu Thr Lys Lys Glu Ala Pro Lys Lys Lys Ser Glu Val Val Ser
            130                 135                 140

Ile Glu Glu Ser Ile Lys Ile Leu Leu Leu Gln Gln Asn Gly Tyr Asp
145                 150                 155                 160

Leu Ala Val Trp Gly Lys Leu Tyr Pro Val Ser Phe Phe Glu Thr Ile
                165                 170                 175

Ser Phe Pro Glu Gly Lys Leu Tyr Glu Asp Met Gly Thr Thr Tyr Lys
                180                 185                 190

Leu Leu Lys Leu Ala Ser Glu Val Val Phe Leu Asp Ala Tyr Asp Tyr
            195                 200                 205

Ala Tyr Val Gln Arg Pro Asn Ser Ile Met Asn Ser Ser Phe Asn Leu
210                 215                 220

Lys Lys Leu Asp Ile Ile Glu Met Val His Glu Met Glu Asn Asp Ile
225                 230                 235                 240

Leu Ala Gln Phe Pro Asn Leu Ala Leu Tyr Val Lys Asn Arg Ala Phe
                245                 250                 255

Ala Ala Glu Val Lys Ile Phe Leu Glu Ile Pro Lys Glu Lys Glu Phe
```

|       |       |       |       | 260   |       |       |       |       | 265   |       |       |       |       | 270   |
|-------|-------|-------|-------|-------|-------|-------|-------|-------|-------|-------|-------|-------|-------|-------|
| Glu   | Gln   | Ala   | Gln   | Lys   | Gln   | Leu   | Trp   | His   | Asp   | Ile   | Lys   | Lys   | Asn   | Arg   | Lys
|       |       |       | 275   |       |       |       | 280   |       |       |       |       | 285   |

Ala Pro Phe Met Thr Lys Gly Ala Arg Leu Lys Asn Arg Leu Gly Ala
    290             295                 300

Ser Leu Ser Phe Leu Gly Lys Ser Leu Phe Leu Thr Ile Gly Lys Gln
305             310                 315                     320

Leu Val Asp Arg (2) INFORMATION FOR SEQ ID NO:11:

(i) SEQUENCE CHARACTERISTICS:
       (A) LENGTH: 360 amino acids
       (B) TYPE: amino acid
       (D) TOPOLOGY: linear (ii) MOLECULE TYPE: protein (xi) SEQUENCE DESCRIPTION: SEQ ID NO:11:

Met Val Ile Tyr Phe Leu Leu Phe Pro Met Ile Ala Met Ile Tyr Leu
 1               5                  10                  15

Met Thr Leu Leu Leu Arg Gln Lys Ala Gln Ile Gln Lys Thr Ile Phe
                20                  25                  30

Cys Val Leu Thr Phe Gly Thr Leu Gly Phe Ile Ser Ala Ser Arg Ala
            35                  40                  45

Ser Ser Val Gly Thr Asp Val Thr Leu Tyr Glu Asn Ile Phe Lys Ser
        50                  55                  60

Ile Asn Tyr Gly Ile Ser Ala Glu Asn Asn Trp Gly Tyr Val Ile Tyr
65                  70                  75                  80

Asn Lys Leu Ile Gly Ser Val Phe Gly Tyr Thr Gly His Glu Ile Thr
                85                  90                  95

Ala Ala Asn Ser Val Leu Ile Thr Ile Leu Ile Gly Ile Phe Ile Trp
            100                 105                 110

Lys Val Ala Glu His Tyr Phe Val Ala Thr Phe Leu Tyr Ile Ser Leu
        115                 120                 125

Phe Tyr Tyr Ala Thr Ser Phe Asn Ile Ser Arg Gln Phe Ile Ala Met
    130                 135                 140

Gly Leu Val Leu Val Ala Ile Ser Phe Ala Leu Asp Lys Lys Val Met
145                 150                 155                 160

Pro Trp Phe Ile Leu Thr Val Leu Ala Thr Leu Phe His Ala Thr Ala
                165                 170                 175

Ile Val Ala Phe Pro Val Tyr Trp Leu Thr Lys Val His Trp Asp Val
            180                 185                 190

Lys Lys Thr Leu Ser Ile Phe Pro Ile Thr Ile Phe Ala Ser Phe Ile
        195                 200                 205

Phe Asp Ala Ile Leu Asn Ile Phe Val Arg Phe Phe Pro His Tyr Glu
    210                 215                 220

Met Tyr Ile Thr Gly Thr Gln Phe Asn Ile Ser Asp Gln Gly Gln Gly
225                 230                 235                 240

Arg Val Val Leu Val Lys Ile Phe Ile Leu Leu Ile Leu Phe Thr Leu
                245                 250                 255

Phe Leu Phe Tyr Lys Lys Ser Tyr Ala Leu Ile Ser Glu Cys His Gln
            260                 265                 270

Ser Leu Ile Ala Leu Thr Thr Val Gly Leu Ser Ile Gly Ile Val Phe
        275                 280                 285

Tyr Asn Asn Ile Leu Leu Asn Arg Ile Glu Met Phe Tyr Ser Ile Leu

|     |     |     |     |     | 290 |     |     |     | 295 |     |     |     |     | 300 |     |
|-----|-----|-----|-----|-----|-----|-----|-----|-----|-----|-----|-----|-----|-----|-----|-----|
| Ser | Ile | Val | Phe | Ile | Pro | Ile | Ala | Ile | Asp | Tyr | Ile | Ser | Leu | Lys | Phe |
| 305 |     |     |     |     | 310 |     |     |     | 315 |     |     |     |     |     | 320 |
| Lys | Gln | Lys | Asp | Ala | Val | Arg | Leu | Met | Leu | Thr | Ile | Gly | Ile | Leu | Leu |
|     |     |     |     | 325 |     |     |     |     | 330 |     |     |     |     | 335 |     |
| Ile | Thr | Leu | Val | Pro | Tyr | Tyr | Ile | Gln | Val | Ser | Gly | Asn | Tyr | Ser | Gly |
|     |     |     | 340 |     |     |     |     | 345 |     |     |     |     | 350 |     |     |
| Ile | Leu | Pro | Tyr | Val | Ile | Gln | Gln |     |     |     |     |     |     |     |     |
|     |     | 355 |     |     |     |     | 360 |     |     |     |     |     |     |     |     |

( 2 ) INFORMATION FOR SEQ ID NO:12:

( i ) SEQUENCE CHARACTERISTICS:
        ( A ) LENGTH: 316 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

|     |     |     |     |     |     |     |     |     |     |     |     |     |     |     |     |
|-----|-----|-----|-----|-----|-----|-----|-----|-----|-----|-----|-----|-----|-----|-----|-----|
| Met | Glu | Asp | Arg | Lys | Lys | Gln | Val | Ile | Leu | Ile | Leu | Ser | His | Arg | Asn |
| 1   |     |     |     | 5   |     |     |     |     | 10  |     |     |     |     | 15  |     |
| Thr | Leu | Ala | Leu | Lys | Ser | Thr | Ile | Glu | Leu | Leu | Asp | Ser | Gln | Tyr | Phe |
|     |     |     | 20  |     |     |     |     | 25  |     |     |     |     | 30  |     |     |
| Asp | Phe | Phe | Leu | His | Ile | Asp | Lys | Lys | Ser | Arg | Ile | Gln | Asp | Phe | Phe |
|     |     |     | 35  |     |     |     | 40  |     |     |     |     | 45  |     |     |     |
| Tyr | Leu | Lys | Lys | Ile | Thr | Lys | Phe | Ser | Thr | Ile | His | Phe | Ser | Glu | Arg |
|     | 50  |     |     |     |     | 55  |     |     |     |     | 60  |     |     |     |     |
| Lys | Asn | Val | His | Trp | Gly | Gly | Phe | Ser | Met | Val | Glu | Ala | Met | Phe | Ala |
| 65  |     |     |     |     | 70  |     |     |     |     | 75  |     |     |     |     | 80  |
| Leu | Leu | Glu | Cys | Ala | Arg | Asp | Thr | Gly | Glu | Tyr | Ser | Tyr | Phe | His | Phe |
|     |     |     |     | 85  |     |     |     |     | 90  |     |     |     |     | 95  |     |
| Leu | Ser | Gly | Asp | Asp | Met | Pro | Ile | Lys | Asp | Asn | Glu | Ile | Val | Phe | Asn |
|     |     |     | 100 |     |     |     |     | 105 |     |     |     |     | 110 |     |     |
| Phe | Phe | Glu | Asn | Ser | Tyr | Pro | Lys | Asn | Phe | Ile | Asp | Ile | Leu | Asp | Phe |
|     |     | 115 |     |     |     |     | 120 |     |     |     |     | 125 |     |     |     |
| Glu | Asn | Val | Asn | Lys | Asn | Ser | Tyr | Phe | Tyr | Glu | Pro | Pro | Glu | Met | Ile |
|     | 130 |     |     |     |     | 135 |     |     |     |     | 140 |     |     |     |     |
| Glu | Glu | Arg | Val | Lys | Tyr | Tyr | Pro | His | Met | Asp | Ile | Leu | Asn | Arg |     |
| 145 |     |     |     |     | 150 |     |     |     |     | 155 |     |     |     | 160 |     |
| Lys | Gly | Thr | Asn | Phe | Ile | Gly | Lys | Lys | Leu | Ile | Tyr | Leu | Gln | Lys | Leu |
|     |     |     |     | 165 |     |     |     |     | 170 |     |     |     |     | 175 |     |
| Leu | Lys | Val | Asn | Arg | Leu | Lys | Asn | Arg | Glu | Ile | Glu | Ile | Phe | Lys | Gly |
|     |     |     | 180 |     |     |     |     | 185 |     |     |     |     | 190 |     |     |
| His | Gln | Trp | Cys | Ser | Leu | Thr | Asn | Gln | Phe | Val | Asp | Ile | Leu | Leu | Asp |
|     |     | 195 |     |     |     |     | 200 |     |     |     |     | 205 |     |     |     |
| Lys | Glu | Glu | Arg | Arg | Val | Gly | Lys | Ser | Tyr | Phe | Ser | Ser | Ser | Leu | Ile |
|     | 210 |     |     |     |     | 215 |     |     |     |     | 220 |     |     |     |     |
| Pro | Asp | Glu | Cys | Tyr | Phe | Gln | Thr | Phe | Ala | Met | Ile | Lys | Lys | Val | Glu |
| 225 |     |     |     |     | 230 |     |     |     |     | 235 |     |     |     |     | 240 |
| Ile | Tyr | Gln | Gln | Lys | Asn | Met | Ser | Ala | Arg | Leu | Ile | Asp | Trp | Thr | Arg |
|     |     |     |     | 245 |     |     |     |     | 250 |     |     |     |     | 255 |     |
| Gly | Lys | Pro | Tyr | Ile | Trp | Arg | Gln | Asp | Phe | Phe | Glu | Ile | Met | Asn |     |
|     |     |     | 260 |     |     |     |     | 265 |     |     |     |     | 270 |     |     |
| Asp | Lys | Asp | Ser | Met | Phe | Ser | Arg | Lys | Phe | Asp | Glu | Asn | Val | Asp | Arg |
|     |     | 275 |     |     |     |     | 280 |     |     |     |     | 285 |     |     |     |

```
Lys  Ile  Ile  Glu  Glu  Ile  Tyr  Ile  Lys  Ile  Arg  Gly  Arg  Ser  Thr  Asp
     290                 295                 300

Glu  Ala  Asn  Lys  Ile  Lys  Asp  Lys  Arg  Phe  Thr  Lys
305                 310                 315
```

( 2 ) INFORMATION FOR SEQ ID NO:13:

( i ) SEQUENCE CHARACTERISTICS:
        ( A ) LENGTH: 473 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

```
Met  Asn  Lys  Tyr  Lys  Lys  Leu  Leu  Ser  Asn  Ser  Leu  Val  Phe  Thr  Ile
 1                   5                  10                  15

Gly  Asn  Leu  Gly  Ser  Lys  Leu  Leu  Val  Phe  Leu  Leu  Val  Pro  Leu  Tyr
                20                  25                  30

Thr  Tyr  Ala  Met  Thr  Pro  Gln  Glu  Tyr  Gly  Met  Ala  Asp  Leu  Tyr  Gln
           35                  40                  45

Thr  Thr  Ala  Asn  Leu  Leu  Leu  Pro  Leu  Ile  Thr  Met  Asn  Val  Phe  Asp
      50                  55                  60

Ala  Thr  Leu  Arg  Phe  Ala  Met  Glu  Lys  Ser  Met  Thr  Lys  Glu  Ser  Val
 65                 70                  75                           80

Leu  Thr  Asn  Ser  Leu  Val  Val  Trp  Cys  Phe  Ser  Ala  Val  Phe  Thr  Cys
                85                  90                       95

Leu  Gly  Ala  Cys  Ile  Ile  Tyr  Ala  Leu  Asn  Leu  Ser  Asn  Lys  Trp  Tyr
               100                 105                 110

Leu  Ala  Leu  Leu  Leu  Thr  Phe  Asn  Leu  Phe  Gln  Gly  Gly  Gln  Ser  Ile
          115                 120                 125

Leu  Ser  Gln  Tyr  Ala  Arg  Gly  Ile  Gly  Lys  Ser  Lys  Ile  Phe  Ala  Ala
     130                 135                 140

Gly  Gly  Val  Ile  Leu  Thr  Phe  Leu  Thr  Gly  Ala  Leu  Asn  Ile  Leu  Phe
145                 150                 155                      160

Leu  Val  Tyr  Leu  Pro  Leu  Gly  Ile  Thr  Gly  Tyr  Leu  Met  Ser  Leu  Val
               165                 170                 175

Leu  Ala  Asn  Val  Gly  Thr  Ile  Leu  Phe  Phe  Ala  Gly  Thr  Leu  Ser  Ile
          180                 185                 190

Trp  Lys  Glu  Ile  Ser  Phe  Lys  Ile  Ile  Asp  Lys  Lys  Leu  Ile  Trp  Gln
     195                 200                 205

Met  Leu  Tyr  Tyr  Ala  Leu  Pro  Leu  Ile  Pro  Ser  Ser  Ile  Leu  Trp  Trp
210                 215                 220

Leu  Leu  Asn  Ala  Ser  Ser  Arg  Tyr  Phe  Val  Leu  Phe  Leu  Gly  Ala
225                 230                 235                      240

Gly  Ala  Asn  Gly  Leu  Leu  Ala  Val  Ala  Thr  Lys  Ile  Pro  Ser  Ile  Ile
               245                 250                 255

Ser  Ile  Phe  Asn  Thr  Ile  Phe  Thr  Gln  Ala  Trp  Gln  Ile  Ser  Ala  Ile
          260                 265                 270

Glu  Glu  Tyr  Asp  Ser  His  Gln  Lys  Ser  Lys  Tyr  Tyr  Ser  Asp  Val  Phe
     275                 280                 285

His  Tyr  Leu  Ala  Thr  Phe  Leu  Leu  Leu  Gly  Thr  Ser  Ala  Phe  Met  Ile
     290                 295                 300

Val  Leu  Lys  Pro  Ile  Val  Glu  Lys  Val  Val  Ser  Ser  Asp  Tyr  Ala  Ser
305                 310                 315                      320

Ser  Trp  Gln  Tyr  Val  Pro  Phe  Phe  Met  Leu  Ser  Met  Leu  Phe  Ser  Ser
               325                 330                 335
```

| | | | | | | | | | | | | | | |
|---|---|---|---|---|---|---|---|---|---|---|---|---|---|---|
|Phe|Ser|Asp|Phe 340|Phe|Gly|Thr|Asn|Tyr 345|Ile|Ala|Ala|Lys|Gln 350|Thr|Lys|
|Gly|Val|Phe 355|Met|Thr|Ser|Ile|Tyr 360|Gly|Thr|Ile|Val|Cys 365|Val|Leu|Leu|
|Gln|Val 370|Val|Leu|Leu|Pro|Ile 375|Ile|Gly|Leu|Asp|Gly 380|Ala|Gly|Leu|Ser|
|Ala 385|Met|Leu|Gly|Phe|Leu 390|Thr|Thr|Phe|Leu|Leu 395|Arg|Val|Lys|Asp|Thr 400|
|Gln|Lys|Phe|Val|Val 405|Ile|Gln|Ile|Lys|Trp 410|Arg|Ile|Phe|Ile|Ser 415|Asn|
|Leu|Leu|Ile|Val 420|Leu|Ala|Gln|Ile|Leu 425|Cys|Leu|Phe|Tyr|Leu 430|Pro|Ser|
|Glu|Phe|Leu 435|Tyr|Phe|Gly|Leu|Ala 440|Leu|Leu|Phe|Cys|Gly 445|Met|Leu|Val|
|Val|Asn 450|Gln|Arg|Thr|Ile|Leu 455|Tyr|Ile|Ile|Met|Ala 460|Leu|Lys|Ile|Lys|
|Asn 465|Lys|Thr|Phe|Gly|Met 470|Lys|Ser|Ser| | | | | | | |

( 2 ) INFORMATION FOR SEQ ID NO:14:

( i ) SEQUENCE CHARACTERISTICS:
        ( A ) LENGTH: 307 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

| | | | | | | | | | | | | | | |
|---|---|---|---|---|---|---|---|---|---|---|---|---|---|---|
|Met 1|Lys|Gln|Ile|Lys 5|Ser|Lys|Ile|Arg|Asp 10|Leu|Gln|Asn|Asn|Phe 15|Thr|
|Tyr|Val|Phe|Gly 20|Lys|Lys|Thr|Phe|Leu 25|Gly|Arg|Gly|Glu|Ala 30|Ile|Ile|
|Ile|Asp|Glu 35|Pro|Glu|His|Gly|Asn 40|Leu|Gly|Asp|Gln|Ala 45|Ile|Ala|Phe|
|Ala|Glu 50|Asn|Gln|Phe|Leu|Val 55|Asn|His|Val|Ser|Val 60|Arg|Asp|Val|Glu|
|His 65|Leu|Ile|Glu|Ser|Lys 70|Thr|Ile|Ser|Glu|Ile 75|Lys|Ser|Ile|Lys|Lys 80|
|Asn|Ile|Gly|Lys|Lys 85|Glu|Leu|Val|Phe|Phe 90|His|Gly|Gly|Gly|Asn 95|Phe|
|Gly|Thr|Leu|Tyr 100|Leu|Lys|Tyr|Glu|Arg 105|Ile|Arg|Arg|Leu|Ala 110|Val|Ser|
|Lys|Leu|Pro 115|Phe|Asn|Lys|Met|Ile 120|Leu|Phe|Pro|Gln|Ser 125|Ile|Ser|Phe|
|Glu|Asp 130|Ser|Arg|Phe|Gly|Gln 135|Lys|Gln|Leu|Asn|Lys 140|Ser|Lys|Lys|Ile|
|Tyr|Ser 145|Gln|Asn|Thr|Asn 150|Phe|Ile|Leu|Thr|Ala 155|Arg|Glu|Pro|Lys|Ser 160|
|Tyr|Gly|Leu|Met|Lys 165|Lys|Cys|Phe|Pro|Tyr 170|Asn|Lys|Val|Ile|Leu 175|Thr|
|Pro|Asp|Ile|Val 180|Leu|Ser|Phe|Lys|Phe 185|Glu|Val|Thr|Ile|Ser 190|Asp|Thr|
|His|Ile|Gly 195|Lys|Glu|Lys|Asp|Ser 200|Val|Ile|Thr|Tyr|Glu 205|Asn|Arg|Gln|

```
His  Tyr  Leu  Glu  Ile  Lys  Trp  Asp  Glu  Ile  Ala  Gln  His  Glu  Val  Ala
     210                213                220

Leu  Thr  Asp  Arg  Leu  His  Gly  Met  Ile  Phe  Ser  Tyr  Ile  Thr  Gly  Thr
225                     230                235                          240

Pro  Cys  Val  Val  Leu  Ala  Asn  Asn  Asn  His  Lys  Ile  Glu  Gly  Thr  Tyr
               245                     250                          255

Lys  His  Trp  Leu  Asn  Glu  Val  Asn  Tyr  Ile  Arg  Phe  Ile  Glu  Asn  Pro
               260                     265                     270

Thr  Val  Glu  Asn  Ile  Leu  Asp  Ala  Ile  Asn  Asp  Leu  Lys  Gln  Ile  Glu
          275                     280                     285

Pro  His  Tyr  Ile  Asp  Leu  Ser  Asp  Lys  Phe  Gln  Pro  Leu  Ile  Asp  Ala
     290                     295                     300

Ile  Lys  Gly
305
```

( 2 ) INFORMATION FOR SEQ ID NO:15:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="oligonuceotide"

( x i ) SEQUENCE DESCRIPTION: SEQ ID NO:15:

GTTGCGGCCG CGATAAAGTG TGATAAGTCC AG        32

( 2 ) INFORMATION FOR SEQ ID NO:16:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="oligonucleotide"

( x i ) SEQUENCE DESCRIPTION: SEQ ID NO:16:

ATAGCGGCCG CTTAGCTCAT GTTGATGCGG        30

( 2 ) INFORMATION FOR SEQ ID NO:17:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="oligonucleotide"

( x i ) SEQUENCE DESCRIPTION: SEQ ID NO:17:

CCTGCGGCCG CGCTTCCTAA TTCTGTAATC G        31

( 2 ) INFORMATION FOR SEQ ID NO:18:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="oligonucleotide"

(x i) SEQUENCE DESCRIPTION: SEQ ID NO:18:

```
CTGGCGGCCG CTACTTCACG TTTCTTTGCA T                      31
```

(2) INFORMATION FOR SEQ ID NO:19:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc ="oligonucleotide"

(x i) SEQUENCE DESCRIPTION: SEQ ID NO:19:

```
TACGCGGCCG CACATAGAAT AAGGCTTTAC G                      31
```

LACTIC BACTERIA PRODUCING EXOPOLYSACCHARIDES

TECHNICAL FIELD

The present invention relates to the use of chromosomal DNA fragments of lactic bacteria coding for at least one enzyme involved in the biosynthesis of exopolysaccharides, as well as to enzymes encoded by these fragments.

PRIOR ART

Lactic bacteria are known to be capable of producing two classes of polysaccharides in their culture medium, namely homopolysaccharides such as dextrans or levans which consist of the repeated assembly of a single sugar, and heteropolysaccharides commonly called exopolysaccharides or EPSs (EPS is short for the term "exopolysaccharide") consisting of the assembly of several different sugars forming a repeating unit (Cerning J., Bactéries lactiques, [Lactic bacteria], Vol I, by Rossart H and Luquet F. M., Lorica, 309–329, 1994).

A lactic bacterium producing an EPS can impart a ropy character and/or a smooth and creamy texture to an acidified milk (Cerning et al., FEMS Microbiol., 87, 113–130, 19/90). EPSs can also display biological activities which are especially advantageous for human or animal health, such as antitumour or probiotic activities, for example (Oda M. et al., Agric. Biol. Chem., 47, 1623–1625, 1983; EP94870139.6).

Moreover, the industry is confronted by a genetic instability of the biosynthesis of EPSs in lactic bacteria. This generally manifests itself during a fermentation by the loss of EPS production by all or part of the lactic bacteria (see "Cerning J." above). Industrial fermented products are thus subject to variations in their EPS content, which is not always acceptable. To remedy these problems, the industry resorts at the present time to the isolation and periodic characterization of its bacteria so as to separate the ones which have lost their original character.

EPS biosynthesis in mesophilic lactic bacteria, that is to say lactic bacteria having optimal growth at 28°–37° C., involves at least one enzyme which effects the linking of the sugars. No chromosomal or plasmid gene of mesophilic lactic bacteria coding for such an enzyme has yet been identified and sequenced, although plasmids involved in EPS biosynthesis are known.

Thus, WO 92/02142 discloses the existence of the plasmid pHV67 which produces in *Lactococcus lactis* subsp. *lactis* (mesophile) a substance capable of increasing the viscosity of a fermented milk. U.S. Pat. No. 5,066,588 describes two plasmids originating from a strain of *Streptococcus cremoris* (mesophile) capable of imparting a thickening character on a *Streptococcus lactis*. Similarly, Vescovo et al. have demonstrated a plasmid from a *Lactobacillus casei* subsp. *casei* strain (mesophile) coding for a Muc+ phenotype, that is to say for functions linked to the production of exocellular thickeners (Vescovo et al., Biotechnology Letters, Vol II, 709–712, 1989).

Lastly, Van den Berg et al., are seeking to isolate from a *Lactobacillus sake* (mesophile) a group of chromosomal genes involved in the biosynthesis of an EPS (Van den Berg D. J. C. et al., First International Conference on Polysaccharide Engineering, Trondheim, Norway, Jun. 6–8, 1994). However, no gene has yet been identified and/or sequenced.

Furthermore, EPS biosynthesis in thermophilic lactic bacteria, that is to say lactic bacteria having optimal growth at 37°–45° C., is not yet well known. It is known, however, not to be associated with a plasmid. Thus, Vescovo et al. showed that the Muc+ phenotype of *Lactobacillus delbrueckii* subsp. *Bulgaricus* strain 2o1 (thermophile) is linked to chromosomal functions (Vescoso et al., Biotechnology Letters, Vol II, 709–712, 1989).

Thus, to date, no chromosomal or plasmid gene or group of genes coding for an EPS of mesophilic or thermophilic lactic bacteria has been identified and/or sequenced.

Hence it would be very advantageous to have means for restoring or stabilizing the original EPS production in lactic bacteria. Furthermore, it would also be advantageous to have means for modifying the structure of an EPS, and thereby creating new EPSs capable of having advantageous properties.

SUMMARY OF THE INVENTION

The objective of the invention is to provide new means for controlling, modifying and/or restoring EPS synthesis in vivo and in vitro.

To this end, the present invention relates to any lactic bacterial DNA of chromosomal origin coding for at least one enzyme involved in the biosynthesis of the EPS possessing the repeat structure

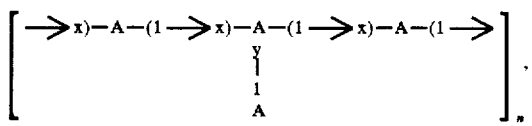

where n>1; A is chosen from the group composed of β-D-Galp, β-D-Glcp and their acetyl and phosphatyl derivatives; and x and y=2, 3, 4, 5 or 6, given that x≠y.

Another subject of the present invention relates to recombinant vectors comprising a DNA fragment according to the present invention.

Another subject of the present invention relates to a protein capable of being involved in the biosynthesis of the EPS having the repeat structure

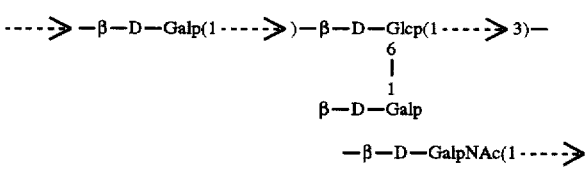

the said protein having the amino acid sequence chosen from the group composed of the sequences SEQ ID NO: 2, 3, 4, 5, 6, 7, 8, 9, 10, 11, 12, 13, 14 and the homologous sequences (sequences presented in the sequence listing below).

Another subject of the present invention relates to a lactic bacterium comprising, integrated in its chromosome or with the aid of a replicable plasmid, a DNA fragment according to the invention.

Another subject of the present invention relates to a method for the production of an EPS, in which (1) a DNA fragment coding for the enzymes according to the invention is cloned into a vector, the said vector comprising, in addition, a sequence permitting autonomous replication in a host cell or integration into the latter, (2) a host cell is transformed with the said vector, and (3) the transformed host cell is then cultured under suitable conditions for the production of an EPS.

The invention also relates to another method for the production of a new EPS, in which (1) a DNA fragment coding for at least one enzyme involved in the biosynthesis of an EPS is cloned into a vector, (2) a lactic bacterium is transformed with the said vector, and (3) the transformed lactic bacterium is then cultured under suitable conditions for the production of a new EPS.

Hence the present invention opens up the possibility of using DNA fragments according to the invention to restore or modify EPS production in a lactic bacterium. Thus it is possible to envisage expressing or overexpressing the DNAs according to the invention in a lactic bacterium, to produce EPSs intended for thickening, and making creamy, drinks or food such as liquid desserts, yoghurts, soups, dairy icecreams, coffee creams, sauces or mayonnaises, for example.

The present invention also makes it possible to have new means for identifying chromosomal genes of lactic bacteria involved in EPS biosynthesis.

Lastly, the present invention also provides new enzymes involved in the biosynthesis of the EPS which is described above. These enzymes may thus be advantageously used to synthesize or modify in vitro a polysaccharide such as an oligosaccharide or an EPS, for example (Ichikawa Y. et al., American Chemical Society, 114, 9283–9289, 1992).

BRIEF DESCRIPTION OF THE FIGURES

FIG. 1.B. representation of the chromosomal inserts of the strain CNCM I-1590, present in the 11 pFS vectors. P1, P2 and P3 indicate the position of the probes which are used during screening.

FIG. 1.C. representation of the genomic insert pFS101 comprising the whole of the eps operon from the SacI restriction site to BamHI, which is cloned into pJIM2279.

DETAILED DESCRIPTION OF THE INVENTION

Figure 1:
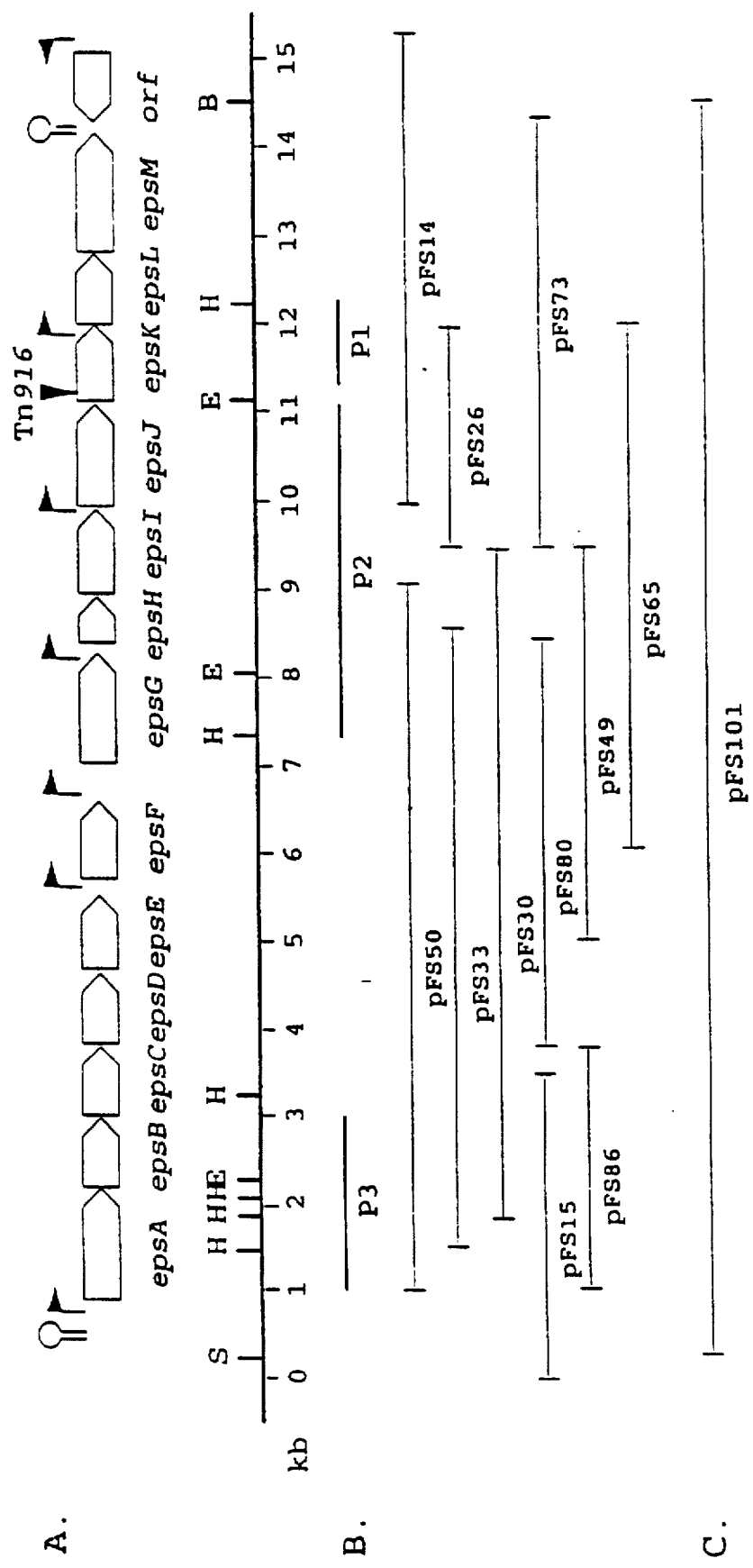
FIG. 1.A. is a physical map of the operon involved in the synthesis of the EPS of the *S. thermophilus* strain CNCM I-1590. The promoters and terminators are represented, respectively, by flags and hairpins. The vertical arrow indicates the position of the insertion site of the transposon Tn916. The horizontal arrows indicate the presence of potential open reading frames (ORFs). The names of the genes corresponding to the ORFs appear below the arrows. The restriction enzymes are shown in abbreviated form (S=SacI; H=HindIII; E=EcoRI; B=BamHI).

In the description which follows, the term "EPS" denotes an exopolysaccharide produced by a lactic bacterium which consists of the assembly of several different sugars forming a repeating unit.

The terms acetyl and phosphatyl derivatives are used to denote galactose or glucose comprising at least one acetyl and phosphatyl radical at positions $C_2$ to $C_6$ on the sugar ring.

For the purposes of the present invention, "homologous sequence" is understood to mean any nucleic acid or amino acid sequence having an identical function, differing from the sequences according to the invention only in the substitution, deletion or addition of a small number of nucleic acid or amino acid bases, for example 1 to 500 base pairs (bp) or 1 to 150 amino acids.

In this context, two DNA sequences which, as a result of the degeneracy of the genetic code, code for the same polypeptide will be considered, in particular, to be homologous. Similarly, two functional proteins which are recognized by the same antibody, the ratio of the values for intensity of recognition of the two proteins by the antibody not exceeding 1000, and preferably 100, for example, will be considered to be homologous.

A sequence will also be considered to be homologous if it displays more than 70% homology with the sequences according to the invention, especially more than 80% or 90%. In the latter case, the homology is determined by the ratio of the number of bases or of amino acids of a homologous sequence which are identical to those of a sequence according to the invention, to the total number of bases or of amino acids of the said sequence according to the invention.

For the purposes of the present invention, "fragment which hybridizes" is understood to mean any fragment capable of hybridizing with the fragments according to the invention by the Southern blotting method (Sambrook et al., Molecular Cloning, A Laboratory Manual, Cold Spring Harbor Laboratory Press, U.S.A., 1989., chapters 9.31 to 9.58). Preferably, the hybridization is conducted under stringent conditions so as to avoid nonspecific or unstable hybridizations.

Lastly, the term "fragment" or "DNA fragment" should be understood to be a double-stranded DNA of chromosomal origin, which may be synthesized, reproduced in vitro, for example, by the known method called the "polymerase chain reaction", or reproduced in vivo in a bacterium of the *Escherichia coli*, *Lactococcus lactis* or *Streptococcus thermophilus* type, for example.

To select a DNA fragment according to the present invention, it is possible to build a library of large DNA fragments from a lactic bacterium producing an EPS in a lactic bacterium not producing any EPS, and then to select the clone or clones producing an EPS. To this end, the genomic DNA of a lactic bacterium producing an EPS is digested with a restriction enzyme which is specific for a relatively rare restriction site (BamHI, SalI, PstI) or by a partial digestion with Sau3A, for example. The digestion product is cloned into an expression or integration plasmid which accepts large fragments (plasmid pSA3 described in Example II), the recombinant plasmids are introduced into the same species of lactic bacterium not producing any EPS, at least one transformed clone producing an EPS is selected and the DNA fragment responsible for EPS production is then identified, isolated and sequenced in a traditional manner.

In view of the fact that the DNA fragments according to the present invention are capable of being large-sized, since they can contain a group of genes involved in EPS biosynthesis, it may be preferable to introduce the recombinant plasmids into the same strain of lactic bacterium from which the fragments originate, apart from the fact that this strain has lost the capacity to produce EPSs following a mutagenic treatment (UV or chemical treatment or treatment with a transposon).

An alternative to the method described above can also consist in building a plasmid library of DNA fragments from a strain of lactic bacterium producing an EPS, in transforming the same strain of lactic bacterium with the plasmids incapable of replicating therein, in selecting the transformants which have integrated a plasmid into their genome by homologous recombination (selection by a resistance to an antibiotic, for example), in selecting the transformants no longer producing any EPS and then in isolating and sequencing the chromosomal DNA fragments of the selected transformants which are adjacent to the integrated plasmid. To this end, it is possible to digest the chromosome of the transformants, to ligate it and then to perform a reverse PCR using probes specific for the integrated plasmid or to introduce the ligation product into a strain in which the recircularized plasmid is capable of replicating, for example.

Another alternative to the selection method described above can also consist in transforming lactic bacteria producing an EPS with a plasmid comprising a transposon, in subjecting the bacteria to conditions under which the transposon is excised from the vector and integrates at random into the genome, in selecting the clones of bacteria which have lost the capacity to produce EPSs, and in isolating the genomic DNA fragments from the said clones into which a transposon has integrated. This method is described in greater detail in Example I presented below.

It should be pointed out that the selection methods described briefly above may be applied to all known lactic bacteria, in particular to mesophilic lactic bacteria such as, for example, *Streptococcus cremoris*, *Streptococcus lactis*, *Lactobacillus casei* subsp. *casei* and *Lactobacillus sake*, and thermophilic lactic bacteria such as, for example, *Streptococcus thermophilus*, *Lactobacillus delbruecki* subsp. *bulgaricus* and *Lactobacillus helvetitus*. To this end, a person skilled in the art has transformation techniques at his disposal for each species of lactic bacterium, and especially for *Lactobacillus delbruecki* subsp. *bulgaricus* (Sasaki Y. et al., FEMS Microbiology Reviews, 12, Fourth Symposium on Lactic Acid Bacteria, Noodwijkerhout, The Netherlands, September 1993).

Furthermore, the selection methods described above make it possible, more often than not, to isolate only a portion of a gene or of a group of genes involved in the biosynthesis of an EPS. Nevertheless, a person skilled in the art may readily identify the remaining portion of the gene or group of genes by selecting in a chromosomal library, using nucleic acid probes based on an isolated fragment, one or more clones containing the remaining portion, for example (see Example I.6).

It was thus possible to characterize a DNA sequence of 15.2 kb of the Streptococcus thermophilus strain deposited on 7th Jun. 1995 with the Collection Nationals de Culture de Microorganisms (C.N.C.M.) [National Collection of Microorganism Cultures] (CNCM), Pasteur Institute, 28 rue du Dr Roux, 75724 Paris cedex 15, France, where it received the deposit No. CNCM I-1590. Moreover, this Gram-positive strain in displays under the microscope an appearance of non-flagellated cocci forming small chains. This strain does not make spores and is a facultative anaerobe.

This sequence of 15.2 kb comprises genes coding for new enzymes involved in the biosynthesis of an EPS having the repeat structure

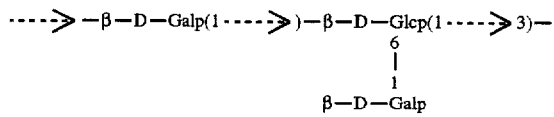

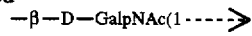

Nucleotides 648 to 15250 of this sequence of 15.2 kb are shown in the sequence SEQ ID NO: 1 given in the sequence listing below. 13 complete genes are delimited in the nucleic acid sequence SEQ ID NO:1 by nucleotides 352-1803, 1807-2535, 2547-3239, 3249-3995, 4051-4731, 4898-5854, 6425-7540, 7736-8212, 8221-9192, 9285-10364, 10392-11339, 11302-12222 and 12233-13651.

It was possible to show that all or part of the sequence SEQ ID NO: 1 makes it possible, following a transformation, to restore an EPS biosynthesis in a host cell such as a mesophilic or thermophilic lactic bacterium which was initially not producing any EPS, in particular in a Streptococcus or a Lactococcus. As an example, the DNA sequence according to the invention may thus be used to restore EPS production in a mutant of the *S. thermophilus* strain CNCM I-1590 no longer producing any EPS (natural mutant or one originating from a mutagenesis).

To restore the biosynthesis of an EPS, all or part of the sequence SEQ ID NO:1 comprising at least one of the abovementioned genes may be integrated into a host cell by means of the method described in EP 564,966, the said method being incorporated by reference in the teaching of the present invention. Briefly, this method makes it possible to be able (1) to transform the host cell with a donor plasmid which does not replicate therein, the said plasmid comprising the said fragment functionally integrated (the reading frame is preserved) into a portion of an operon originating from the host cell; (2) to identify the transformants comprising the whole of the plasmid, integrated; (3) to select transformants comprising only, integrated into the chromosome, the fragment according to the invention, the other sequences of the plasmid having been excised from the chromosome; and (4) to culture the selected transformants under suitable conditions for the production of an EPS.

It may be noted that this method makes it possible not to use functional promoter and translation activator sequences. Furthermore, the culture conditions suitable for EPS production are within the capacity of a person skilled in the art, who can use standard culture media and choose the pH, temperature and agitation of the optimum medium according to the strain used.

It is also possible to choose to clone all or part of the sequence SEQ ID NO:1 comprising at least one of the abovementioned genes into a self-replicating expression plasmid downstream of functional promoter and translation activator sequences and, where appropriate, upstream of a terminator, and then to transform a host cell with the recombinant plasmid.

Moreover, it may be observed that the EPS produced by a host cell transformed with the sequence SEQ ID NO:1, for example a *Lactococcus lactis* not initially producing an EPS, may be different from the EPS which should normally be synthesized by the recombinant enzymes, in this instance the EPS produced by the strain CNCM I-1590. The use of all or part of the sequence of 5.2 kb can hence permit the creation of variants of the EPS described above.

Similarly, it could be shown that all or part of the sequence SEQ ID NO:I can also make it possible, following a transformation, to modify the repeat structure of an EPS initially produced by a host cell, for example by a mesophilic or thermophilic lactic bacterium, in particular a Streptococcus or a Lactococcus.

These observations thus open up the possibility of producing a novel method of production of a new EPS, in which (1) a DNA fragment coding partially or totally for at least one enzyme involved in the biosynthesis of an EPS is cloned into a vector; (2) lactic bacteria are transformed with the recombinant vector; (3) where appropriate, a lactic bacterium producing a new EPS is selected; and (4) the transformed lactic bacterium is then cultured under suitable conditions for the production of a new EPS. Preferably, the vector codes for the proteins according to the invention. Furthermore, the lactic bacterium can produce an EPS other than the one synthesized by the proteins encoded by the said vector.

In particular, a DNA fragment coding partially for at least one enzyme involved in the biosynthesis of a first EPS is cloned into an integration vector, the recombinant vector is introduced into mesophilic or thermophilic lactic bacteria capable, where appropriate, of producing a second EPS via one or more chromosomal or plasmid genes, the bacteria which have integrated the integration vector into their chromosome are isolated, and those which produce a new EPS are then selected on account of the inactivation of one or more genes involved in the biosynthesis of the second EPS. Preferably, the first and the second EPS are identical, and a DNA fragment coding partially (at least 15 base pairs) for at least one enzyme involved in the addition of a sugar to the side chain of the repeating unit or in the modification of a sugar, such as a sulpho-, phospho- or acetyltransferase, for example, is chosen.

Similarly, a DNA fragment coding totally for at least one enzyme involved in the biosynthesis of a first EPS may be cloned into a replicative expression vector, the recombinant vector may be introduced into mesophilic or thermophilic lactic bacteria capable, where appropriate, of producing a second EPS via one or more chromosomal or plasmid genes, the bacteria containing the replicative vector may be isolated, and those which produce a new EPS may then be selected on account of the expression of one or more genes involved in the biosynthesis of the first EPS. Preferably, DNA fragments coding for enzymes involved in the modification of a sugar, such as a sulpho-, phospho- or acetyltransferase, for example, or in the addition of the repeating unit of a sugar such as a glucosyl- or a galactosyltransferase, for example, are chosen.

Preferably, at least one of genes carried by the sequence SEQ ID NO:1 is used totally or partially. At least one plasmid gene of mesophilic lactic bacteria involved in the biosynthesis of an EPS (gene which may be sequenced from known plasmids) may also be used.

Lastly, the recombinant vector can be any linear or circular, single- or double-stranded expression or integration DNA fragment comprising a DNA sequence according to the invention, in particular all or part of the sequence SEQ ID NO:1. In the event of the method described in EP 564,966 not being used, care should be taken that the vector can express the DNA according to the invention through appropriate nucleic acid sequences (promoter; ribosome binding site; preferred codon) and, where appropriate, that it comprises one or more origins of replication from various bacteria, in particular from Escherichia coli and/or from a Streptococcus, for example.

The invention also relates to new enzymes encoded by the genes of the sequence SEQ ID NO:1, in particular the sequences which are homologous with them. Their use to modify or synthesize in vitro an oligosaccharide or a polysaccharide such as an EPS, for example, may thus be envisaged. For this purpose, it is preferable to purify at least one of these enzymes, by overexpressing their gene in a traditional manner in a bacterium and isolating them in a traditional manner, by precipitation and/or chromatography of the cultural medium, for example.

Another subject of the present invention relates to a lactic bacterium comprising, integrated in its chromosome or with the aid of a replicable plasmid, a DNA sequence according to the invention. Preferably, the sequence comprises at least one of the genes of the sequence SEQ ID NO:1.

The invention also relates to any use of fragments of the sequence SEQ ID NO:1, or of fragments of the strand complementary to this sequence, of at least 15 base pairs, as primer for carrying out a PCR or as probe for detecting in vitro or inactivating in vivo genes of lactic bacteria involved in the biosynthesis of an EPS. This lower limit is set arbitrarily on account of the fact that small fragments which hybridize specifically are generally 15–25 bp in length.

EXAMPLES

The present invention is described in greater detail below by means of the additional description which follows, which relates to examples of obtaining DNA fragments, recombinant plasmids and transformed bacteria according to the invention. These examples are preceded by a description of the culture media. It is self-evident, however, that these examples are given by way of illustration of the subject-matter of the invention, of which they in no way constitute a limitation. DNA manipulation and the cloning and transformation of bacterial cells are, unless otherwise specified, performed according to the protocols described in the work by Sambrook et al. cited above. Percentages are given by weight except where otherwise stated.

Media: (add 1.5% of bacto-agar for a solid medium)

M17 (Difco, U.S.A.): tryprone 0.5%, soytone 0.5%, hydrolysed meat 0.5%, yeast extract 0.25%, ascorbic acid 0.05%, magnesium sulphate 0.025%, disodiumbeta-glycero-phosphate 1.9% and water.

LM17: M17 medium comprising 1% of lactose.

GM17: M17 medium comprising 1% of glucose.

MSK: skimmed milk (10% reconstituted powder) comprising 0.1% of yeast extract.

MAM: skimmed milk (10% reconstituted powder) comprising 10% of a mixture of amino acids (495 mg/l Ala, 343 mg/l Arg, 682 mg/l Asp, 59 mg/l Cys, 1229 mg/l Glu, 759 mg/l Gly, 153 mg/l His, 215 mg/l Iso, 470 mg/l Leu, 565 mg/l Lys, 122 mg/l Met, 255 mg/l Phe, 436 mg/l Pro, 68 mg/l Ser, 170 mg/l Thr, 61 mg/l Try, 304 mg/l Val adjusted to pH 5).

HJL: tryprone 3%, beef extract 0.2%, yeast extract 1%, lactose 1% and $KH_2PO_4$ pH 6.5 0.5%.

Ruthenium red: 0.5% yeast extract, skimmed milk powder 10%, sucrose 1%, agar 1.5% and 0.08 g/l of ruthenium red (see FR2,632,968).

Example I cloning of a DNA fragment of S. thermophilus strain Sfi6

I.1. Selection of an S. thermophilus strain producing EPS: the strains of lactic bacteria from the Nestlé collection are cultured in HJL liquid medium, and dilutions thereof are plated out on ruthenium red solid medium. Strains producing EPS remain white since the EPSs prevent the dye from staining their cell wall. In contrast, non-producing strains stain red on account of the affinity of the dye for the peptidoglycan of their cell wall.

In this way, S. thermophilus strain Sfi6, which received the deposit number CNCM I-1590 and which will be designated in the examples which follow by the expression "strain Sfi6", was selected from the lactic bacteria producing EPS.

I.2. Repeat structure of the EPS: the structure of the EPS produced by the strain Sfi6 has been published by Doco et al. (Carbohyd. Res., 198, 313–321, 1995). This EPS possesses the composition Glc:Gal:GalNac=1:2:1, and the tetrasaccharide repeat unit

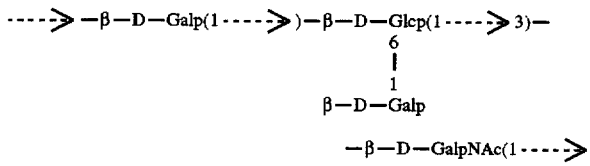

I.3. Mutagenesis with the transposon Tn916: the strain Sfi6 is rendered resistant to streptomycin by culturing it by repeated transfers in HJL medium supplemented with contents increasing from 20 to 2000 µg/ml of streptomycin, and by then selecting the strains which become naturally resistant.

The streptomycin-resistant strain Sfi6 and *Enterococcus faecalis* strain JH2-2, which possesses a plasmid pAM180 carrying the transposon Tn916 (Tn916 is known to carry a tetracycline resistant gene; Gawron et al., Nature, 300, 281–283, 1982) are conjugated. For this purpose, 1 ml of an overnight culture in M17 medium at 37° C. of *E. faecalis* strain JH2-2 is mixed with 10 ml of an overnight culture in HJL medium at 42° C. of the strain Sfi6, the cells are centrifuged and resuspended in tubes comprising 100 µl of HJL medium, the suspension is applied to LM17 solid medium which is incubated at 37° C. for 20 h, the cells are recovered by scraping and resuspended in tubes of 10 ml of HJL liquid medium, the tubes are incubated at 42° C. for 4 h, shaking them from time to time, and dilutions of the cultures are then plated out on solid LM17 medium supplemented with 2.5 µg/ml of tetracycline and 2000 µg/ml of streptomycin.

By carrying out 20 conjugations in parallel (independent mutations), it was possible in this way to select $2 \times 10^4$ tetracycline- and streptomycin-resistant transconjugents.

I.4. Selection of mutants of the strain Sfi6 no longer producing EPS [EPS(−)phenotype]: the resistant transconjugants are transferred onto ruthenium red solid medium supplemented with 2.5 µg/ml of tetracycline and 2000 µg/ml of streptomycin. Approximately 10% of the transconjugents form EPS(−) red colonies. Approximately 800 red colonies are then selected and cultured overnight in microtitration plates comprising 200 µl of HJL medium supplemented with 2.5 µg/ml of tetracycline. 100 µl of the HJL culture are then cultured in i ml of MSK milk. Approximately 25% of the red colonies tested display a stable EPS(−) phenotype in the milk (the milk is not thick and ropy, and analysis of the culture supernatant does not disclose any EPS). The other red colonies display an EPS(+) phenotype or recover the EPS(+) phenotype after several subcultures in the milk.

In conclusion, the EPS(−) stable mutants have lost their capacity to produce EPSs as a result of the integration of the transposon Tn916 into a chromosomal gene involved in the biosynthesis of EPSs. In effect, the EPS(−) stable mutants can recover an EPS(+) phenotype when they are cultured in a growth medium lacking tetracycline (excision and loss of the transposon).

I.5 Characterization of EPS(−) stable mutants: approximately 100 stable mutants are analysed by the Southern blotting of a chromosomal DNA preparation from the mutants, digested with HindIII, and hybridization of the Southern blot filter with the radioactive term gene (encodes a tetracycline resistance) originating from the plasmid pIC182 (Hill et al., Applied and Env. Micro., 54, 1230–1236, 1988). Approximately 85% of the mutants analysed display an identical preponderant band corresponding to a locus called "locus A". For some of the other mutants, two further preponderant bands (locus B and C), corresponding to known loci involved in the biosynthesis of the cell wall (publication in preparation), may be noted.

I.6 Characterization of the locus A: the chromosomal regions close to the integrated transposon Tn916 may be isolated by reverse PCR. For this purpose, 1 µg of a chromosomal DNA preparation from an arbitrarily chosen mutant (mutant No.1) is digested in a traditional manner with HindIII for 4 h, the DNA is extracted with phenol/ chloroform and diluted in 720 µl of water, the diluted DNA is heated to 56° C. for 5 minutes, the DNA is cooled on ice, 80 µl of a 10-fold concentrated ligation buffer and 5 units of a T4 ligase (Boehringer-Mannheim) are added to it, and it is incubated at 12° C. for 16 h, heated to 70° C. for 15 min to inactivate the ligase and then concentrated in a volume of 100 µl by several successive extractions in butanol. 10 µl of the ligation mixture, 100 pmol of primers, 15 mM dNTPs, 10 µl of buffer and 0.2 unit of Super-Taq polymerase (Stehlin GmbH) are then added into a PCR device. The nucleic acid primers are chosen on the basis of the known sequence of the transposon Tn916.

Using the primers having the sequence SEQ ID NO:15 and SEQ ID NO:16, a 1-kb fragment could be isolated by PCR. Furthermore, using the primers SEQ ID NO:17 and SEQ ID NO:18, a 4-kb fragment could be isolated (see the sequence listing below).

A third, 0.8-kb fragment may also be isolated from the mutant No.1, by carrying out a second reverse PCR from its chromosomal DNA digested with RsaI and using the primers having the sequences SEQ ID NO:18 and SEQ ID NO:19 (see the sequence listing below).

The 1-kb and 0.8-kb fragments were cloned into the linearized plasmid pGEMT (Promega, U.S.A.). Sequencing of these fragments by the dideoxynucleotide method (f-mol® DNA Sequencing System kit, Promega) shows two sequences which, on being matched up, cover three open reading frames (ORFs) corresponding to nucleotides 9933 to 11643 of the sequence SEQ ID NO:1.

The 1-kb and 4-kb fragments were also used to screen a λ-ZAP Express (Stratagene, U.S.A.) library containing DNA fragments of the strain Sfi6. For this purpose, according to the supplier's recommendations, a DNA preparation from the said mutant is partially digested with Sau3A, the fragments are separated by agarose gel electrophoresis, the bands corresponding to 5- to 12-kb fragments are cut from the gel, and the DNA is eluted and then ligated to the λ-ZAP Express vector previously digested with BamHI. The ligation product is encapsidated in vitro using the GigagoldIII system (Stratagene), the phages are then mixed with *Escherichia coli* XL1Blue (Stratagene) according to the supplier's recommendations and the mixture is then plated out on a Petri dish. The recombinant plaques are then analysed by hybridization of their DNA, transferred onto a Hybond N membrane (Amersham Life Sciences, UK), with the 1-kb and 4-kb fragments previously rendered radioactive (Random Primed DNA Labelling kit, Boehringer-Mannheim).

From 3000 recombinant plaques, approximately 20 positive plaques could be selected by hybridization, from which the A-ZAP Express vectors were then isolated, and the pCMV vectors containing a chromosomal insert were thereafter excised (see the recommendations of the supplier Stratagene). These recombinant vectors are called "pFS" in the examples which follow.

The chromosomal inserts of 11 pFS vectors were then sequenced (f-mol® DNA Sequencing System kit), these being the vectors pFS14, pFS15, pFS26, pFS30, pFS33, pFS49, pFS50, pFS65, pFS73, pFS80 and pFS86 (see FIG. 1.B) which comprise, respectively, fragments corresponding to the nucleotides of the sequence SEQ ID NO:1, 9314-14602, 1-3159, 7988-11253, 1702-7991, 1361-7229, 4400-8477, 648-7676, 5997-11253, 8474-13489, 3550-7229 and 648-1702.

By matching up the nucleic acid sequences of the different chromosomal inserts, it was possible in this way to characterize a sequence of 15.2 kb corresponding to the locus A of the strain Sfi6 (see FIG. 1.A). Nucleotides 648 to 15250 of this sequence of 15.2 kb are shown in the sequence SEQ ID NO:1.

I.7. Analysis of the sequence SEQ ID NO:1

The sequence SEQ ID NO:1 comprises the whole of the eps operon of the strain Sfi6. This sequence comprises 13 complete ORFs in the same orientation, which are called eps A, B, C, D, E, F, G, H, I, J, K, L and M, (see FIG. 1.A). This sequence comprises, in addition, one complete ORF at the 3' end of the sequence, which is encoded by the complementary strand. This ORF, called orfZ, probably marks the end of the operon on account of its reverse orientation relative to the other ORFs.

Comparison of the amino acid sequences encoded by the first 13 ORFs with those of the proteins present in the Swiss-Prot data bank, using the softwares FASTA, PEPPLOT and PILEUP from GCG-software, Wisconsin, U.S.A., enables the function of the 13 proteins encoded by the eps operon to be deduced. The results are presented below.

The epsA ORF (nucleotides 352-1803) codes for an EpsA protein (SEQ ID NO:2) having 26.4% identity with the LytR protein of *Bacillus subtilis* which is involved in the regulation of the autolysin N-acetylmuramoyl-L-alanine (Lazaveric et al., J. Gen. Microbiol., 138, 1949–1961, 1992). Hence EpsA is probably a regulator protein for the eps operon. Moreover, since a regulator ORF of an operon is generally found upstream of the other ORFs, the epsA gene is probably the first gene of the eps operon. This is confirmed by the fact that a terminator is found at nucleotides 230-252, a promoter at nucleotides 274-302 and a ribosome binding site at nucleotides 340-345 of the sequence SEQ ID NO:1.

The epsB gene (nucleotides 1807-2535) codes for an EpsB protein (SEQ ID NO:3) having 67.5% identity with the CpsA protein of *Streptococcus agalactiae* and 30% identity with the CapC protein of *Staphylococcus aureus* (Rubens et al., Mol. Microbiol., 8, 843–885, 1993; Linet al., J. Bacteriol., 176, 7005–7016, 1994). The precise function of these genes is still unknown, apart from the fact that they are essential for the synthesis of the capsule which consists of polysaccharides coupled to the phospholipids of the outer membrane of the bacteria.

The epsC gene (nucleotides 2547-3239) codes for an EpsC protein (SEQ ID NO:4) having 52% identity with the CpsB protein of *Streptococcus agalactiae* which is involved in the synthesis of the capsule (Rubens et al.). EpsC also has 23% identity, 49% similarity and a hydrophobicity profile comparable to that of the CLD proteins of *Salmonella typhimurium*, *Salmonella enterica* and *Escherichia coli* (Batchelor et al., J. Bacteriol., 174, 228–5236, 1992; Bastin et al., Mol. Microbiol., 7, 25–734, 1993). It should be pointed out that the CLD proteins are involved in the control of the length of the polysaccharide chains during their biosynthesis.

The epsD gene (nucleotides 3249-3995) codes for an EpsD protein (SEQ ID NO:5) having 60.5% identity with the Cpsc protein of *Streptococcus agalactiae*, having 34.5% identity with the CapA protein of *Staphylococcus aureus* and having 33% identity with the ExoP protein of *Rhizobium meliloti* (Rubens et al., Linet al.; Becker et al., Mol. Gen. Genet., 241, 367–379, 1993). The ExoP protein is a membrane protein which is involved in the translocation of EPS and/or of EPS precursors.

The epsE gene (nucleotides 4051-4731) codes for an EpsE protein (SEQ ID NO:6) displaying significant homologies with many proteins having galactosyltransferase activity (Rubens et al.). Hence this gene probably codes for a galactosyltransferase.

It may be noted that the epsB, C, D and E genes of *S. thermophilus* Sfi6 are similar to those of the operon of *S. agalactiae* comprising the cpsA, B, C and D genes (Rubens et al.). Furthermore, they are organized in the same way. Although the polysaccharides of the capsule and the EPS of the two strains are very different, this indicates that a chromosomal region has probably been transferred between these two species.

The epsF gene (nucleotides 4898-5854) codes for an EpsF protein (SEQ ID NO:7) having, respectively, 24.5% and 23% identity with the CapH and CapM proteins of *S. mutans* which are probably involved as glycosyltransferases in the biosynthesis of the capsule (Lin et al.).

The epsG gene (nucleotides 6425-7540) codes for an EpsG protein (SEQ ID NO:8) having 20.5% identity and 50% similarity with the N-acetylglucosaminetransferase of *Salmonella typhimurium* LT2 which is involved in the biosynthesis of the LPS polysaccharide of the outer membrane (MacLachlan et al., J. Bacteriol., 173, 7151–7163, 1991). Since an N-acetylglucosamine is not involved in the biosynthesis of the EPS of the strain Sfi6 (there is no acetylated glucose), the epsG gene probably codes for a glucosyltransferase, an N-acetylgalactosyltransferase or an N-acetylglucosyltransferase having N-acetylglucosamine epimerase activity.

The epsH gene (nucleotides 7736-8212) codes for an EpsH protein (SEQ ID NO:9) having strong homologies with NodL-LacA-CysE acetyltransferases (Downie et al., Mol. Microbiol. 3, 1649–1651, 1989). Accordingly, the EpsH protein could be an acetyltransferase involved in the biosynthesis of the N-acetylgalactosamine of the EPS.

The epsI gene (nucleotides 8221-9192) codes for an EpsI protein (SEQ ID NO:10) having 24% identity with a protein, encoded by the RfbV ORF of the rfb cluster of *Salmonella typhimurium*, which is probably a glycosyltransferass (Jiang et al.; Liu et al., J. Bacteriol., 177, 4084–4088, 1995).

The epsJ gene (nucleotides 9285-10364) codes for an Epsj protein (SEQ ID NO:11) having 20% identity and a hydrophobicity profile comparable to that of a protein of an ORF of the rfb cluster of *Salmonella enterica* which is itself similar to a polymerase of the O antigen of group B and C2 salmonellae (Lee et al., J. Gen. Microbiol., 138, 1843–1855, 1992; Morona et al., J. Bacteriol. 176, 733–747, 1994). The epsJ gene could hence encode an EPS polymerase which might polymerize the tetrasaccharide unit of the EPS.

The epsK gene (nucleotides 10392-11339) codes for an EpsK protein (SEQ ID NO: 12) having 18% identity and 42% similarity with the protein, encoded by the lipB gene of *Neisseria meningitidis*, which is involved in the biosynthesis of the capsule by coupling polysaccharides to the phospholipids of the outer membrane (Frosch et al., Mol. Microbiol., 8, 483–493, 1993). Given that the *S. thermophilus* bacteria do not have an outer membrane (Gram-positive), the epsK gene could hence encode an enzyme involved in the coupling of the EPSs to the phospholipids of the cell membrane which, in concert with an EPS transport molecule (probably EpsC and EpsD) and an enzyme which detaches EPSs, might participate in the transport of the EPS through the membrane (model in agreement with the one put forward by Frosch et al.).

Moreover, it may be pointed out that the transposon Tn916 is integrated into the epsK gene of the mutant No. 1 used to identify the eps operon (see point I.6 above), between nucleotides 10540-10541 of the sequence SEQ ID NO:1.

The epsL gene (nucleotides 11302-12222) codes for an EpsL protein (SEQ ID NO:14) which does not display any homology with known proteins. The first 38 nucleotides are covered by the 3' end of epsK, suggesting a coordinated expression of the two proteins and an activity of the EpsL protein in the membrane transport of the EPS.

The epsM gene (nucleotides 12233-13651) codes for an EpsM protein (SEQ ID NO:13) which does not display any homology with known proteins of the Swiss-Prot data bank. This gene is definitely involved in the biosynthesis of the EPS of the strain Sfi6, since there is not, upstream, a specific promoter for this gene.

The orfZ gene (13732-14305 on the complementary strand) is present in the reverse orientation relative to the remainder of the ORFs of the eps operon. Accordingly, it is probably not involved in the biosynthesis of the EPS of the strain Sfi6. Furthermore, it does not display any homology with known proteins of the Swiss-Prot data bank.

In conclusion, the chromosomal inserts isolated from the 11 pSF vectors (see point I.6 above) cover a chromosomal region of *S. thermophilus* strain Sfi6 which is manifestly involved in the biosynthesis of the EPS. 13 complete genes which comprise, upstream, a promoter delimiting the beginning of the eps operon could thus be identified.

Example II
inactivation of the epsJ gene

The epsJ gene of the eps operon is inactivated by homologous recombination in order to confirm its importance in the biosynthesis of the EPS.

For this purpose, a DraI-SalI fragment is isolated from plasmid pGEMT containing the 0.8-kb PCR fragment (see Example 1.6 above) and ligated into the temperature-sensitive plasmid pSA3 (Dao et al., Appl. Environ. Microbiol., 49, 115–119, 1985) previously digested with EcoRV and SalI, the *E. coli* strain XL1-blue is transformed with the ligation product, transformants are selected, a recombinant plasmid is isolated, and *S. thermophilus* strain Sfi6 is transformed by electropotation with the recombinant plasmid by means of a method adapted from the one described by Slos et al. (Appl. Environ. Microbiol., 57, 1333–1339, 1991). The cells subjected to a discharge of 2.1 kV, 25 µF and 400Ω are resuspended in i ml of HJL medium, which is incubated for 4 h at 37° C. (permissive temperature), the cells are plated out on LM17 solid medium supplemented with 2.5 µg/ml of erythromycin, which is incubated for 16 h at 37° C., and the transformed colonies which survive are then selected. The selected colonies are then incubated in 2 ml of HJL medium supplemented with 2.5 µg/ml of erythromycin until the optical density at 600 nm ($OD_{600}$) of the culture reaches 0.2, the culture is subjected to 45° C. until the $OD_{600}$ reaches 1.0 (the plasmid no longer replicates), and dilutions of the culture are then plated out on solid LM17 medium supplemented with 2.5 µg/ml of erythromycin, which is incubated for 12 h at 45° C.

The colonies which survive have integrated the recombinant pSA3 plasmid into the epsJ gene. This may be verified by Southern blotting of a chromosomal DNA preparation of the surviving colonies, digested with EcoRI (cuts only once in pSA3), and hybridization of the Southern blot filter with the abovementioned radioactive DraI-SalI fragment. Colonies which have integrated plasmid pSA3 display two bands on the Southern blot filter. Furthermore, colonies which have integrated the recombinant pSA3 plasmid into epsJ display an EPS(−) phenotype on ruthenium red solid medium, and have lost their ropy character in MSK milk (see Example I.4 above).

Example III
inactivation of the eps A, B, C, D, E, F, G, H, I, K, L and M genes It was shown in Examples I and II that inactivation of the epsK and epsJ genes, by insertion of a transposon or of an integrative plasmid, interrupts EPS biosynthesis in the strain Sfi6.

Similarly, the other genes of the eps operon of the strain Sfi6 may be inactivated by homologous recombination, and an interruption of EPS biosynthesis may thus be observed. For this purpose, a fragment of an ORF originating from one of the 11 pFS vectors described in Example 1.6 above is amplified by PCR. It is cloned into plasmid pSA3, then transformed and integrated into the strain Sfi6 under the same conditions as those described in the previous-example.

Example IV
restoration of EPS production pFS30 is cut with EcoRI, the fragments are separated, the 5.5-kb fragment is ligated to pFS14 previously digested with EcoRI, XL1-blue cells are transformed with the ligation product, transformed clones displaying a correct orientation of the inserts are selected, a plasmid called pFS30-14 is isolated, a central EcoRI fragment of pFS65 is ligated to pFS30-14 previously cut with EcoRI, XL1-blue cells are transformed with the ligation product, and transformed clones displaying a correct orientation of the inserts are then selected. The resultant recombinant plasmid, called pFS30-65-14, comprises nucleotides 1702 to 14602 of the sequence SEQ ID NO:1.

pFS30-65-14 is then cut with SalI and SmaI, the 2.9 kb fragment is separated and ligated to pSA3 previously cut with EcoRV and SalI, XL1-blue cells are transformed with the ligation product, transformed clones are selected and recombinant pSA3 plasmids are isolated.

The *S. thermophilus* strain CNCM I-1292, deposited on 29th Mar. 1993, is transformed by electropotation with the recombinant pSA3 plasmids. This Gram-positive strain displays under the microscope an appearance of non-flagellated cocci forming small chains, does not make spores, is a facultative anaerobe, does not produce any EPS and possesses in its genome 1000 bp corresponding to the 5' end of the eps operon. The recombinant pSA3 plasmid can hence integrate into the genome of the strain CNCM I-1292. Some of the transformed clones display an EPS(+) phenotype on ruthenium red solid medium, and a ropy character in MSK milk.

Example V
restoration of EPS production

The chromosome of the strain Sfi6 is digested with enzymes which do not cut in the sequence SEQ ID NO:1 (BamHI, SalI, NruI, StuI), the digestion product is separated on agarose gel, the 15–25-kb bands are eluted and ligated into pSA3 previously cut with a suitable restriction enzyme, the *S. thermophilus* strain CNCM I-1292 is transformed by electroporation, and transformants are then selected by transfer of the colonies onto a filter followed by hybridization of their DNA with the insert of pFS14 previously made radioactive. Some of the transformed clones display an EPS(+) phenotype on ruthenium red solid medium, and a ropy character in MSK milk.

Example VI modification of an EPS

The *S. thermophilus* strain CNCM I-1422, deposited on 18th May 1994, is transformed by electroporation with the recombinant pSA3 plasmid of Example V. This Gram-positive strain displays under the microscope an appearance of non-flagellated cocci forming small chains, does not make spores, is a facultative anaerobe and produces an EPS having the composition Glc:Gal=2:2.

Example VII modification of an EPS

The *S. thermophilus* strain CNCM I-1351, deposited on 5th Aug. 1993, is transformed by electropotation with the recombinant pSA3 plasmid of Example V. This Gram-positive strain displays under the microscope an appearance of non-flagellated cocci forming small chains, does not make spores, is a facultative anaerobe and produces an EPS having the composition Glc:Gal:Rha=1:3:2.

Example VIII modification of an EPS

The chromosomal DNA of the strain CNCM I-1590 is isolated by the method of Slos et al. (Appl. Environ. Microbiol., 57, 1333–1339, 1991). The DNA preparation is digested with SacI and BamHI, the DNA fragments are separated by electrophoresis on 0.7% agarose gel, the 12- to 16-kb fragments are eluted, and the DNA extracted is ligated to the vector pJIM2279 (obtained from P. Renault, INRA, Jouy-en-josas, Paris, France) previously digested with SacI and BamHI and then dephosphorylated. *Lactococcus lactis* strain MG1363 (a. Bacteriol., 154, 1–9, 1983), cultured on GM17 medium at 30° C., is transformed by the method of De Vos et al. (Gene, 85, 169–176, 1989). The transformed clones are selected by hybridization of the genomic DNA of the clones with one of the probes having the sequences SEQ ID NO: 15, 16, 17, 18 and 19. Among 400 transformants, 6 positive clones are selected, one of which comprises a plasmid called pFS101 shown in FIG. 1.C.

To determine whether plasmid pFS101 is capable of inducing the production of recombinant EPS, *L. lactis* MG1363 is retransformed with pFS101 and plated out directly on ruthenium red solid medium. For comparison, *L. lactis* MG1363 is transformed with the plasmid pJIM2279 and is then plated out directly on ruthenium red solid medium. The results show that all the colonies comprising pJIM2279 have a red phenotype (3000 EPS(−) colonies), while more than 99.5% of the colonies comprising pFS101 have a white phenotype (800 EPS(+) colonies, apart from 2 colonies). Hence *L. lactis* strain MG1363 transformed with pFS101 produces a recombinant EPS.

Production of the EPS of *L. lactis* strain MG1363 transformed with pFS101 is brought about by culturing the organism in MAM medium, at a pH of 5.5, at 30° C. with magnetic stirring at 60 rpm. The recombinant EPS is isolated by mixing the culture medium with 40% of trichloroacetic acid, centrifuging the mixture for 20 min it at 8000 g, mixing the precipitate with an equal volume of acetone, incubating the mixture at 4° C. for 12 h, precipitating the mixture at 10,000 g for 1 h, suspending the precipitate in water, adjusting the pH of the mixture to 7, dialysing it against water for 24 h, ultracentrifuging it at 100,000 g for 1 h, recovering the supernatant and then lyophilizing the supernatant. For comparison, *L. lactis* strain MG1363 transformed with pJIM2279 is cultured under the same conditions and the sugars are isolated in the same manner.

The total amount of neutral sugars is determined by the method of Dubois et al. (Anal. Chem., 28, 350–356, 1956). The results show that the strain transformed with pFS101 produces 10 mg/l of sugars, expressed as glucose equivalents, while the strain transformed with pJIM2279 produces traces of sugar (<1 mg/l).

Figure 2:
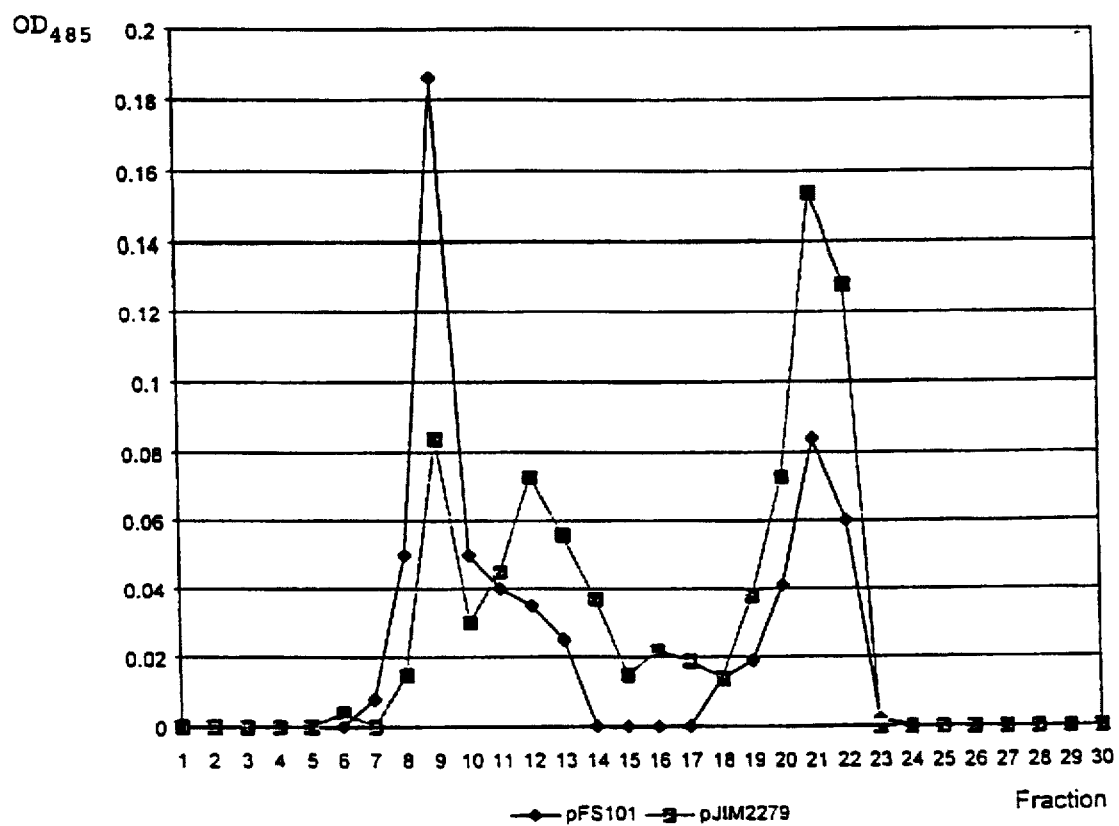
FIG. 2. representation of the optical density at 485 nm of the gel filtration chromatography fractions comprising the sugars produced by *Lactococcus lactis* strain MG1363 transformed with pFS101 or pJIM2279. Fraction 9: $2 \times 10^6$ daltons (Da); fractions 11–13: $5 \times 10^5$ Da; fractions 14–16: $7.2 \times 10^4$ Da; fractions 17–18: $4 \times 10^4$ Da; fraction 19 and above: $<5 \times 10^3$ Da.

The molecular weight of the recombinant EPS is estimated by chromatography on a Superose-6 (Pharmacia) gel filtration column which is connected to the FPLC system (Pharmacia) previously calibrated with commercial dextran (Sigma) of $2 \times 10^6$ to $5 \times 10^3$ daltons (Da). For this purpose, 0.25 to 1 ml of a sample comprising 250 μg of neutral sugars is applied to the column, which is eluted with a flow of 0.5 ml/min in 50 mM phosphate buffer pH 7.2. For comparison, the sugars produced by the strain transformed with pJIM2279 are separated in the same manner. The results presented in FIG. 2 show that the strain transformed with pJIM2279 produces a small amount of heterogeneous polysaccharides whose origin is definitely the cell wall ($2-0.5 \times 10^6$ Da; fractions 8–15) and a large amount of low molecular weight oligosaccharides (mono-and disaccharides; fractions 20–22). In contrast, the strain transformed with pFS101 manifestly displays a recombinant EPS with a high molecular weight of approximately $2 \times 10^6$ Da (fraction 9).

The sugar composition of the recombinant EPS is determined by gas chromatography by the method of Neeser et al. (Anal. Biochem., 142, 58–67, 1984). The results show that the culture medium of the strain transformed with pFS101 comprises, in terms of molarity, a 1:3 ratio of Glc:Gal. Traces of rhamnose originating from the cell wall may be detected. In contrast, no GalNac is detected.

Hence the composition of the EPS produced by *L. lactis* strain MG1363 transformed with pFS101 is different from that of the EPS produced by the *S. thermophilus* strain CNCM I-1590. It may reasonably be estimated that the structure of the recombinant EPS is the same as that of the EPS of the strain CNCM I-1590, except for the fact that GalNac is replaced by a galactose.

---

What is claimed is:

1. A polypeptide composition involved in the production of an exopolysaccharide possessing the repeat structure:

$$\cdots\!\!\gg\!-\beta\!-\!D\!-\!Galp(1\cdots\!\!\gg)\!-\!\beta\!-\!D\!-\!Glcp(1\cdots\!\!\gg 3)\!-$$
$$\underset{\underset{\beta-D-Galp}{|}}{\overset{6}{|}}$$
$$-\beta-D-GalpNAc(1\cdots\!\!\gg$$

comprising polypeptides having the amino acid sequences of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and SEQ ID NO:14, or fragments thereof wherein one or more of said polypeptides is recombinantly produced.

2. An isolated polypeptide which is involved in the biosynthesis of an exopolysaccharide possessing the repeat structure:

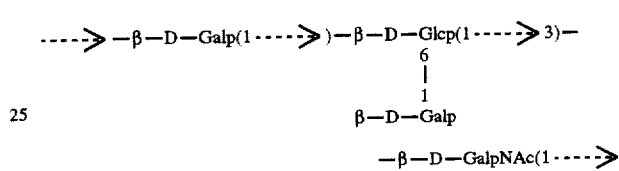

and which is encoded by a nucleic acid sequence that is more than 90% homologous to the nucleic acid sequence of at least one gene chosen from the group of genes delimited in the nucleic acid sequence SEQ ID NO:1 by nucleotides 352-1803, 1807-2535, 2547-3239, 3249-3995, 4051-4731, 4898-5854, 6425-7540, 7736-8212, 8221-9192, 9285-10364, 10392-11339, 11302-12222 and 12233-13651.

3. An isolated protein encoded by one of the open reading frames of the nucleic acid sequence of SEQ ID NO: 1.

\* \* \* \* \*

UNITED STATES PATENT AND TRADEMARK OFFICE
CERTIFICATE OF CORRECTION

Page 1 of 2

PATENT NO. : 5,733,765

DATED : March 31, 1998

INVENTORS : Mollet et al.

It is certified that error appears in the above-identified patent and that said Letters Patent is hereby corrected as shown below:

Column 2, lines 41-46: the repeat structure should read as follows:

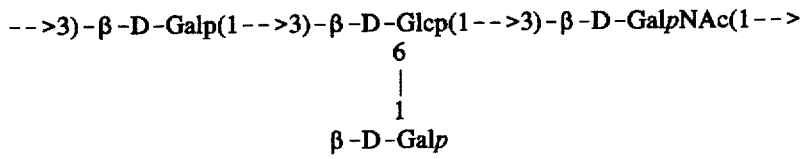

Column 5, lines 62-65 through column 6, lines 1-2: the repeat structure should read as follows:

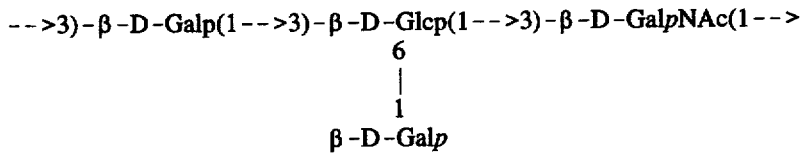

Column 9, lines 12-17: the repeat unit should read as follows:

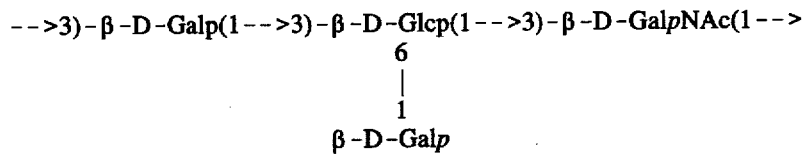

UNITED STATES PATENT AND TRADEMARK OFFICE
CERTIFICATE OF CORRECTION

Column 71, lines 25-30: the repeat structure should read as follows:

$$\rightarrow 3)\text{-}\beta\text{-D-Galp}(1\rightarrow 3)\text{-}\beta\text{-D-Glcp}(1\rightarrow 3)\text{-}\beta\text{-D-Gal}p\text{NAc}(1\rightarrow$$
$$\overset{6}{\underset{1}{|}}$$
$$\beta\text{-D-Gal}p$$

Column 72, lines 22-27: the repeat structure should read as follows:

$$\rightarrow 3)\text{-}\beta\text{-D-Galp}(1\rightarrow 3)\text{-}\beta\text{-D-Glcp}(1\rightarrow 3)\text{-}\beta\text{-D-Gal}p\text{NAc}(1\rightarrow$$
$$\overset{6}{\underset{1}{|}}$$
$$\beta\text{-D-Gal}p$$

Signed and Sealed this

Sixteenth Day of June, 1998

Attest:

BRUCE LEHMAN

*Attesting Officer*  *Commissioner of Patents and Trademarks*